United States Patent [19]
Hoover et al.

[11] Patent Number: 5,952,322
[45] Date of Patent: Sep. 14, 1999

[54] METHOD OF REDUCING TISSUE DAMAGE ASSOCIATED WITH NON-CARDIAC ISCHEMIA USING GLYCOGEN PHOSPHORYLASE INHIBITORS

[75] Inventors: Dennis J. Hoover, Stonington; William H. Martin, Essex; Judith L. Treadway, Gales Ferry; W. Ross Tracey, Niantic, all of Conn.

[73] Assignee: Pfizer Inc., New York, N.Y.

[21] Appl. No.: 08/978,384

[22] Filed: Nov. 25, 1997

Related U.S. Application Data

[60] Provisional application No. 60/031,584, Dec. 5, 1996.

[51] Int. Cl.$^6$ ................................................. A61K 31/395
[52] U.S. Cl. ........................ 514/210; 514/323; 514/414; 514/419
[58] Field of Search ................................. 574/414, 419, 574/323, 210

[56] References Cited

U.S. PATENT DOCUMENTS

| | | |
|---|---|---|
| 4,879,283 | 11/1989 | Belzer et al. . |
| 5,266,561 | 11/1993 | Cooper et al. . |
| 5,281,581 | 1/1994 | Cooper et al. . |
| 5,395,822 | 3/1995 | Izumi et al. . |
| 5,541,218 | 7/1996 | Ikeda et al. . |
| 5,635,527 | 6/1997 | Ono et al. ................................. 514/415 |
| 5,723,449 | 3/1998 | Sommadossi et al. .................... 514/50 |

FOREIGN PATENT DOCUMENTS

| | | |
|---|---|---|
| WO9402459 | 2/1994 | WIPO . |
| WO9524391 | 9/1995 | WIPO . |
| WO9639384 | 12/1996 | WIPO . |
| WO9639385 | 12/1996 | WIPO . |

OTHER PUBLICATIONS

T. Blundell et al., Structural biology and diabetes mellitus: molecular pathogenesis and rational drug design, *Diabetologia*, (1992) 35, Suppl 2, pp. S69–S76.

Peter J. Kasvinsky et al., The Regulation of Glycogen Phosphorylase α by Nucleotide Derivatives, *The Journal of Biological Chemistry* vol. 253, No. 9. Issue of May 10, 1978, pp. 3343–3351.

J. L. Martin et al., Glucose Analogue Inhibitors of Glycogen Phosphorylase: The Design of Potential Drugs for Diabetes, *Biochemistry*, 1991, vol. 30, No. 42, pp. 10101–10116.

Peter J. Kasvinsky et al., Synergistic Regulation of Phosphorylase α by Glucose and Caffeine*, *The Journal of Biological Chemistry*, vol. 253, No. 24, Issue of Dec. 25, 1978, pp. 9102–9106.

Christopher B. Newgard et al., Cloning, Sequence Analysis, Chromosomal Mapping, Tissue Expression, and Comparison with the Human Liver and Muscle Isozymes, *The Journal of Biological Chemistry*, vol. 263, No. 8, Mar. 15, 1988, pp. 3850–3857.

J. H. Weil, "Biochimie Generale", Masson and Cie ed., "II. Degradation du glycogene. (Glycogenolyse)", 1975, p. 175, p. 176, p. 181.

Raymond A. Swanson et al., Regional brain glycogen stores and metabolism during complete global ischaemia, *Neurological Research*, 1989, vol. 11, Mar., pp. 24–28.

Christine Marie, Fasting Prior to Transient Cerebral Ischemia Reduces Delayed Neuronal Necrosis, *Metabolic Brain Disease*, vol. 5 No. 2, 1990, pp. 66–75.

Wole, Christopher L. et al., Loss of Myocardial Protection Ater Preconditioning Correlates With the Time Course of Glycogen Recovery Within the Preconditioned Segment, *Circulation*, , vol. 87, No. 3, Mar. 1993, pp. 881–892.

Allard, M. F. et al., Preischemic glycogen reduction of glycolytic inhibition improves postischemic recovery of hypertrophied rate hearts, *American Physiological Society*, 1994, pp. H66–H74.

Primary Examiner—James H. Reamer
Attorney, Agent, or Firm—Peter C. Richardson; Gregg C. Benson; A. Dean Olson

[57] ABSTRACT

A method of preventing non-cardiac tissue damage resulting from ischemia and/or hypoxia, comprising administering to a patient in need of such treatment an effective amount of an glycogen phosphorylase inhibitor.

24 Claims, No Drawings

METHOD OF REDUCING TISSUE DAMAGE ASSOCIATED WITH NON-CARDIAC ISCHEMIA USING GLYCOGEN PHOSPHORYLASE INHIBITORS

This application claims the benefit of U.S. Provisional Application No. 60/031,584 filed on Dec. 5, 1996, the priority of which is hereby claimed.

BACKGROUND OF THE INVENTION

This invention relates to the use of glycogen phosphorylase inhibitors to reduce tissue damage resulting from non-cardiac ischemia in mammals, including human patients.

Glycogen phosphorylase inhibitors constitute a class of compounds which have use in the treatment of diabetes mellitus.

Commonly assigned PCT applications PCT/IB95/00443 and PCT/IB95/00442 disclose the use of certain glycogen phosphorylase inhibitors for the treatment of damage from perioperative myocardial ischemia.

Glycogenolysis in tissues is catalyzed by the enzyme glycogen phosphorylase (GP). In humans, three different isoforms of the enzyme glycogen phosphorylase have been identified to date: these are the human liver isoform (herein referred to as HLGP), the human muscle isoform (herein referred to as HMGP), and the human brain isoform (herein referred to as HBGP). These three isoforms of human glycogen phosphorylase represent the products of three distinct human genes and are closely related as evidenced by sharing 80–83% amino acid identity (C. B. Newgard, D. R. Littman, C. van Gendered, M. Smith, and R. J. Fletterick, *J. Biol. Chem.* 263:3850–3857, 1988). Note herein that the term glycogen phosphorylase or the abbreviation GP will be utilized to refer to any or all of the three known isoforms of the human glycogen phosphorylase enzyme, any additional human glycogen phosphorylase isoenzymes identified in the future, and to all isoforms of mammalian glycogen phosphorylase enzymes in general. GP enzymes cleave the glycogen macromolecule to release glucose-1-phosphate and a new shortened glycogen macromolecule. Two types of glycogen phosphorylase inhibitors have been reported to date: glucose and glucose analogs [for example, Martin, J. L. et al. Biochemistry 1991, 30, 10101] and caffeine and other purine analogs [for example, Kasvinsky, P. J. et al. *J. Biol. Chem.* 1978, 253, 3343–3351 and 9102–9106]. These compounds, and glycogen phosphorylase inhibitors in general, have been postulated to be of potential use for the treatment of NIDDM by decreasing hepatic glucose production and lowering glycemia. [Blundell, T. B. et al. Diabetologia 1992, 35, Suppl. 2,569–576 and Martin et al. Biochemistry 1991, 30, 10101].

SUMMARY OF THE INVENTION

This invention is directed to a method of reducing non-cardiac tissue damage (e.g., substantially preventing tissue damage, inducing tissue protection) resulting from ischemia and/or hypoxia. The method comprises administering to a mammal, including a human patient, in need of such treatment an amount of a glycogen phosphorylase inhibitor effective at reducing non-cardiac tissue damage.

One group of glycogen phosphorylase inhibitors includes compounds of the Formula I

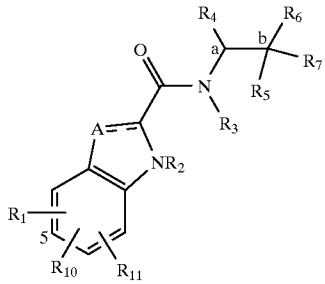

Formula I and the pharmaceutically acceptable salts and prodrugs thereof wherein the dotted line (—) is an optional bond;

A is —C(H)=, —C(($C_1$–$C_4$)alkyl)= or —C(halo)= when the dotted line (—) is a bond, or A is methylene or —CH(($C_1$–$C_4$)alkyl)- when the dotted line (—) is not a bond;

$R_1$, $R_{10}$ or $R_{11}$, are each independently H, halo, 4-, 6- or 7-nitro, cyano, ($C_1$–$C_4$)alkyl, ($C_1$–$C_4$)alkoxy, fluoromethyl, difluoromethyl or trifluoromethyl;

$R_2$ is H;

$R_3$ is H or ($C_1$–$C_5$)alkyl;

$R_4$ is H, methyl, ethyl, n-propyl, hydroxy($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, phenyl($C_1$–$C_4$)alkoxy ($C_1$–$C_4$)alkyl, thien-2- or -3-yl($C_1$–$C_4$)alkyl or fur-2- or -3-yl($C_1$–$C_4$)alkyl wherein said $R_4$ rings are mono-, di- or tri-substituted independently on carbon with H, halo, ($C_1$–$C_4$)alkyl, ($C_1$–$C_4$)alkoxy, trifluoromethyl, hydroxy, amino or cyano; or $R_4$ is pyrid-2-, -3- or -4-yl($C_1$–$C_4$)alkyl, thiazol-2-, -4- or -5-yl($C_1$–$C_4$)alkyl, imidazol -1-, -2-, -4- or -5-yl ($C_1$–$C_4$)alkyl, pyrrol-2- or -3-yl($C_1$–$C_4$)alkyl, oxazol-2-, -4- or -5-yl-($C_1$–$C_4$)alkyl, pyrazol-3-, -4- or -5-yl ($C_1$–$C_4$)alkyl, isoxazol-3-, -4- or -5-yl ($C_1$–$C_4$)alkyl, isothiazol-3-, -4- or -5-yl($C_1$–$C_4$)alkyl, pyridazin-3- or -4-yl-($C_1$–$C_4$)alkyl, pyrimidin-2-, -4-, -5- or -6-yl ($C_1$–$C_4$)alkyl, pyrazin-2- or -3-yl($C_1$–$C_4$)alkyl or 1,3,5-traiazin-2-yl($C_1$–$C_4$)alkyl, wherein said preceding $R_4$ heterocycles are optionally mono- or di-substituted independently with halo, trifluoromethyl, ($C_1$–$C_4$) alkyl, ($C_1$–$C_4$)alkoxy, amino or hydroxy and said mono- or di-substituents are bonded to carbon;

$R_5$ is H, hydroxy, fluoro, ($C_1$–$C_5$)alkyl, ($C_1$–$C_5$)alkoxy, ($C_1$–$C_6$)alkanoyl, amino($C_1$–$C_4$)alkoxy, mono-N- or di-N,N-($C_1$–$C_4$)alkylamino($C_1$–$C_4$)alkoxy, carboxy ($C_1$–$C_4$)alkoxy, ($C_1$–$C_5$)alkoxy-carbonyl($C_1$–$C_4$) alkoxy, benzyloxycarbonyl($C_1$–$C_4$)alkoxy, or carbonyloxy wherein said carbonyloxy is carbon-carbon linked with phenyl, thiazolyl, imidazolyl, 1H-indolyl, furyl, pyrrolyl, oxazolyl, pyrazolyl, isoxazolyl, isothiazolyl, pyridazinyl, pyrimidinyl, pyrazinyl or 1,3,5-triazinyl and wherein said preceding $R_5$ rings are optionally mono-substituted with halo, ($C_1$–$C_4$)alkyl, ($C_1$–$C_4$) alkoxy, hydroxy, amino or trifluoromethyl and said mono-substituents are bonded to carbon;

$R_7$ is H, fluoro or ($C_1$–$C_5$)alkyl; or $R_5$ and $R_7$ can be taken together to be oxo;

$R_6$ is carboxy, ($C_1$–$C_8$)alkoxycarbonyl, C(O)$NR_8R_9$ or C(O)$R_{12}$, wherein $R_8$ is H, ($C_1$–$C_3$)alkyl, hydroxy or ($C_1$–$C_3$)alkoxy; and $R_9$ is H, $(C_1-C_8)$alkyl, hydroxy, $(C_1-C_8)$alkoxy, methylene-perfluorinated$(C_1-C_8)$alkyl, phenyl, pyridyl, thienyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, pyridazinyl, pyrimidinyl, pyrazinyl, piperazinyl or 1,3,5-triazinyl wherein said preceding $R_9$ rings are carbon-nitrogen linked; or $R_9$ is mono-, di- or tri-substituted $(C_1-C_5)$alkyl, wherein said substituents are independently H, hydroxy, amino, mono-N- or di-N,N-$(C_1-C_5)$alkylamino; or $R_9$ is mono- or di-substituted $(C_1-C_5)$alkyl, wherein said substituents are independently phenyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl or 1,3,5-triazinyl wherein the nonaromatic nitrogen-containing $R_9$ rings are optionally mono-substituted on nitrogen with $(C_1-C_6)$ alkyl, benzyl, benzoyl or $(C_1-C_6)$alkoxycarbonyl and wherein the $R_9$ rings are optionally mono-substituted on carbon with halo, $(C_1-C_4)$alkyl, $(C_1-C_4)$alkoxy, hydroxy, amino, or mono-N- and di-N,N $(C_1-C_5)$ alkylamino provided that no quaternized nitrogen is included and there are no nitrogen-oxygen, nitrogen-nitrogen or nitrogen-halo bonds;

$R_{12}$ is piperazin-1-yl, 4-$(C_1-C_4)$alkylpiperazin-1-yl, 4-formylpiperazin-1-yl, morpholino, thiomorpholino, 1-oxothiomorpholino, 1,1-dioxo-thiomorpholino, thiazolidin-3-yl, 1-oxo-thiazolidin-3-yl, 1,1-dioxo-thiazolidin-3-yl, 2-$(C_1-C_6)$alkoxycarbonylpyrrolidin-1-yl, oxazolidin-3-yl or 2(R)-hydroxymethylpyrrolidin-1-yl; or $R_{12}$ is 3- and/or 4-mono- or di-substituted oxazetidin-2-yl, 2-, 4-, and/or 5mono- or di-substituted oxazolidin-3-yl, 2-, 4-, and/or 5- mono- or di- substituted thiazolidin-3-yl, 2-, 4-, and/or 5- mono- or di- substituted 1-oxothiazolidin-3-yl, 2-, 4-, and/or 5- mono- or di-substituted 1,1-dioxothiazolidin-3-yl, 3- and/or 4-, mono- or di-substituted pyrrolidin-1-yl, 3-, 4- and/or 5-, mono-, di- or tri-substituted piperidin-1-yl, 3-, 4-, and/or 5- mono-, di-, or tri-substituted piperazin-1-yl, 3-substituted azetidin-1-yl, 4- and/or 5-, mono- or di-substituted 1,2-oxazinan-2-yl, 3-and/or 4-mono- or di-substituted pyrazolidin-1-yl, 4- and/or 5-, mono- or di-substituted isoxazolidin-2-yl, 4- and/or 5-, mono- and/or di-substituted isothiazolidin-2-yl wherein said $R_{12}$ substituents are independently H, halo, $(C_1-C_5)$-alkyl, hydroxy, amino, mono-N- or di-N,N-$(C_1-C_5)$ alkylamino, formyl, oxo, hydroxyimino, $(C_1-C_5)$ alkoxy, carboxy, carbamoyl, mono-N-or di-N,N-$(C_1-C_4)$alkylcarbamoyl, $(C_1-C_4)$alkoxyimino, $(C_1-C_4)$alkoxymethoxy, $(C_1-C_6)$alkoxycarbonyl, carboxy$(C_1-C_5)$alkyl or hydroxy$(C_1-C_5)$alkyl;

with the proviso that if $R_4$ is H, methyl, ethyl or n-propyl $R_5$ is OH;

with the proviso that if $R_5$ and $R_7$ are H, then $R_4$ is not H, methyl, ethyl, n-propyl, hydroxy$(C_1-C_3)$alkyl or $(C_1-C_3)$alkoxy$(C_1-C_3)$alkyl and $R_6$ is C(O)NR$_8$R$_9$, C(O)R$_{12}$ or $(C_1-C_4)$alkoxycarbonyl.

A first group of preferred compounds of Formula I consists of those compounds wherein $R_1$ is 5-H, 5-halo, 5-methyl or 5-cyano;

$R_{10}$ and $R_{11}$ are each independently H or halo;

A is —C(H)=;

$R_2$ and $R_3$ are H;

$R_4$ is phenyl$(C_1-C_2)$alkyl wherein said phenyl groups are mono-, di- or tri-substituted independently with H or halo or mono- or di- substituted independently with H, halo, $(C_1-C_4)$alkyl, $(C_1-C_4)$alkoxy, trifluoromethyl, hydroxy, amino or cyano; or $R_4$ is thien-2- or -3-yl$(C_1-C_2)$alkyl, pyrid-2-, -3- or -4-yl $(C_1-C_2)$alkyl, thiazol-2-, -4- or -5-yl$(C_1-C_2)$alkyl, imidazol -1-, -2-, -4- or -5-yl$(C_1-C_2)$alkyl, fur-2- or -3-yl $(C_1-C_2)$alkyl, pyrrol-2- or -3-yl$(C_1-C_2)$alkyl, oxazol-2-, -4- or -5-yl-$(C_1-C_2)$alkyl, pyrazol-3-, -4- or -5-yl $(C_1-C_2)$alkyl, isoxazol-3-, -4- or -5-yl$(C_1-C_2)$alkyl wherein said preceding $R_4$ heterocycles are optionally mono- or di-substituted independently with halo, trifluoromethyl, $(C_1-C_4)$alkyl, $(C_1-C_4)$alkoxy, amino or hydroxy and said mono- or di-substituents are bonded to carbon;

$R_5$ is hydroxy;

$R_6$ is C(O)NR$_8$R$_9$ or C(O)R$_{12}$; and $R_7$ is H.

Within the above first group of preferred compounds of Formula I is a first group of especially preferred compounds wherein the carbon atom a has (S) stereochemistry;

the carbon atom b has (R) stereochemistry;

$R_4$ is phenyl$(C_1-C_2)$alkyl, thien-2-yl-$(C_1-C_2)$alkyl, thien-3-yl-$(C_1-C_2)$alkyl, fur-2-yl-$(C_1-C_2)$alkyl or fur-3-yl-$(C_1-C_2)$alkyl wherein said rings are mono- or di-substituted independently with H or fluoro;

$R_6$ is C(O)NR$_8$R$_9$;

$R_8$ is $(C_1-C_3)$alkyl, hydroxy or $(C_1-C_3)$alkoxy; and $R_9$ is H, $(C_1-C_8)$alkyl, hydroxy, hydroxy$(C_1-C_6)$alkyl, $(C_1-C_8)$alkoxy, pyridyl, morpholinyl, piperazinyl, pyrrolidinyl, piperidinyl, imidazolyl or thiazolyl or $(C_1-C_4)$alkyl mono-substituted with pyridyl, morpholinyl, piperazinyl, pyrrolidinyl, piperidinyl, imidazolyl or thiazolyl.

Within the above first group of especially preferred compounds are the particularly preferred compounds 5-Chloro-1H-indole-2-carboxylic acid [(1S)-((R)-hydroxy-dimethylcarbamoyl-methyl)-2-phenyl-ethyl]-amide, 5,6-Dichloro-1H-indole-2-carboxylic acid {(1S)-[(R)-hydroxy-(methoxy-methylcarbamoyl)-methyl]-2-phenyl-ethyl}-amide, 5-Chloro-1H-indole-2-carboxylic acid {(1S)-[(R)-hydroxy-(methoxy-methylcarbamoyl)-methyl]-2-phenyl-ethyl}-amide, 5-Chloro-1H-indole-2-carboxylic acid ((1S)-{(R)-hydroxy-[(2-hydroxy-ethyl)methyl-carbamoyl]-methyl}-2-phenyl-ethyl)-amide, 5-Chloro-1H-indole-2-carboxylic acid {(1S)-[(R)-hydroxy-(methyl-pyridin-2-yl-carbamoyl)-methyl]-2-phenyl-ethyl}-amide or 5-Chloro-1H-indole-2-carboxylic acid ((1S)-{(R)-hydroxy-[methyl-(2-pyridin-2yl-ethyl)-carbamoyl]-methyl}-2-phenyl-ethyl)-amide.

Within the above first group of especially preferred compounds are the compounds wherein a. $R_1$ is 5-chloro;

$R_{10}$ and $R_{11}$ are H;

$R_4$ is benzyl;

$R_8$ is methyl; and $R_9$ is methyl;

b. $R_1$ is 5-chloro;
   $R_{11}$ is H;
   $R_{10}$ is 6-chloro;
   $R_4$ is benzyl;
   $R_8$ is methyl; and
   $R_9$ is methoxy;
c. $R_1$ is 5-chloro;
   $R_{10}$ and $R_{11}$ are H;
   $R_4$ is benzyl;
   $R_8$ is methyl; and
   $R_9$ is methoxy;
d. $R_1$ is 5-chloro;
   $R_{10}$ and $R_{11}$ are H;
   $R_4$ is benzyl;
   $R_8$ is methyl; and
   $R_9$ is 2-(hydroxy)ethyl;
e. $R_1$ is 5-chloro;
   $R_{10}$ and $R_{11}$ are H;
   $R_4$ is benzyl;
   $R_8$ is methyl; and
   $R_9$ is pyridin-2-yl; and
f. $R_1$ is 5-chloro;
   $R_{10}$ and $R_{11}$ are H;
   $R_4$ is benzyl;
   $R_8$ is methyl; and
   $R_9$ is 2-(pyridin-2-yl)ethyl.

Within the above first group of preferred compounds of Formula I is a second group of especially preferred compounds wherein the carbon atom a is (S) stereochemistry;
the carbon atom b is (R) stereochemistry;
$R_4$ is phenyl($C_1$–$C_2$)alkyl, thien-2-yl-($C_1$–$C_2$)alkyl, thien-3-yl-($C_1$–$C_2$)alkyl, fur-2-yl-($C_1$–$C_2$)alkyl or fur-3-yl-($C_1$–$C_2$)alkyl wherein said rings are mono- or di- substituted independently with H or fluoro;
$R_6$ is C(O)$R_{12}$; and
$R_{12}$ is morpholino, 4-($C_1$–$C_4$)alkylpiperazin-1-yl, 3-substituted azetidin-1-yl, 3- and/or 4-, mono- or di-substituted pyrrolidin-1-yl, 4- and/or 5- mono- or di-substituted isoxazolidin-2-yl, 4- and/or 5-, mono- or di-substituted 1,2-oxazinan-2-yl wherein said substituents are each independently H, halo, hydroxy, amino, mono-N- or di-N,N-($C_1$–$C_6$)alkylamino, oxo, hydroxyimino or alkoxy.

Within the above second group of especially preferred compounds are the particularly preferred compounds 5-Chloro-1H-indole-2-carboxylic acid [(1S)-benzyl-(2R)-hydroxy-3-(4-methylpiperazin-1-yl)-3-oxo-propyl]-amide hydrochloride, 5-Chloro-1H-indole-2-carboxylic acid [(1S)-benzyl-(2R)-hydroxy-3-(3-hydroxy-azetidin-1 -yl)-3-oxo-propyl]-amide, 5-Chloro-1H-indole-2-carboxylic acid ((1S)-benzyl-(2R)-hydroxy-3isoxazolidin-2-yl-3-oxo-propyl)-amide, 5-Chloro-1H-indole-2-carboxylic acid ((1S)-benzyl-(2R)-hydroxy-3-[1,2]oxazinan-2-yl-3-oxo-propyl)-amide, 5-Chloro-1H-indole-2-carboxylic acid [(1S)-benzyl-(2R)-hydroxy-3-((3S)hydroxy-pyrrolidin-1-yl)-3-oxo-propyl]-amide, 5-Chloro-1H-indole-2-carboxylic acid [(1S)-benzyl-3-((3S,4S)-dihydroxy-pyrrolidin-1-yl)-(2R)-hydroxy-3-oxo-propyl]-amide, 5-Chloro-1H-indole-2-carboxylic acid [(1S)-benzyl-3-(cis-3,4-dihydroxy-pyrrolidin-1-yl)-(2R)-hydroxy-3-oxo-propyl]-amide or 5-Chloro-1H-indole-2-carboxylic acid ((1S)-benzyl-(2R)-hydroxy-3-morpholin-4-yl-3oxo-propyl)-amide.

Within the above second group of especially preferred compounds are the compounds wherein a. $R_1$ is 5-chloro;
   $R_{10}$ and $R_{11}$ are H;
   $R_4$ is benzyl; and
   $R_{12}$ is 4-methylpiperazin-1-yl;
b. $R_1$ is 5-chloro;
   $R_{10}$ and $R_{11}$ are H;
   $R_4$ is benzyl; and
   $R_{12}$ is 3-hydroxyazetidin-1-yl;
c. $R_1$ is 5-chloro;
   $R_{10}$ and $R_{11}$ are H;
   $R_4$ is benzyl; and
   $R_{12}$ is isoxazolidin-2-yl;
d. $R_1$ is 5-chloro;
   $R_{10}$ and $R_{11}$ are H;
   $R_4$ is benzyl; and
   $R_{12}$ is (1,2)-oxazinan-2-yl;
e. $R_1$ is 5-chloro;
   $R_{10}$ and $R_{11}$ are H;
   $R_4$ is benzyl; and
   $R_{12}$ is 3(S)-hydroxypyrrolidin-1-yl;
f. $R_1$ is 5-chloro;
   $R_{10}$ and $R_{11}$ are H;
   $R_4$ is benzyl; and
   $R_{12}$ is (3S,4S)-dihydroxypyrrolidin-1-yl;
g. $R_1$ is 5-chloro;
   $R_{10}$ and $R_{11}$ are H;
   $R_4$ is benzyl; and
   $R_{12}$ is cis-3,4-dihydroxypyrrolidin-1-yl; and
h. $R_1$ is 5-chloro;
   $R_{10}$ and $R_{11}$ are H;
   $R_4$ is benzyl; and
   $R_{12}$ is morpholino.

A second group of preferred compounds of Formula I consists of those compounds wherein $R_1$ is H, halo, methyl or cyano;
$R_{10}$ and $R_{11}$ are each independently H or halo;
A is —C(H)═;
$R_2$ and $R_3$ are H;
$R_4$ is phenyl($C_1$–$C_2$)alkyl wherein said phenyl groups are mono-, di- or tri-substituted independently with H or halo or mono- or di- substituted independently with H, halo, ($C_1$–$C_4$)alkyl, ($C_1$–$C_4$)alkoxy, trifluoromethyl, hydroxy, amino or cyano; or $R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol -1-, -2-, -4- or -5-yl($C_1$–$C_2$)alkyl, fur-2- or -3-yl ($C_1$–$C_2$)alkyl, pyrrol-2- or -3-yl($C_1$–$C_2$)alkyl, oxazol-2-, -4- or -5-yl-($C_1$–$C_2$)alkyl, pyrazol-3-, -4- or -5-yl ($C_1$–$C_2$)alkyl, isoxazol-3-, -4- or -5-yl($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;

$R_5$ is hydroxy;
$R_6$ is carboxy or ($C_1$–$C_8$)alkoxycarbonyl; and
$R_7$ is H, fluoro or ($C_1$–$C_6$)alkyl.

Within the second group of preferred compounds of Formula I is a group of especially preferred compounds wherein the carbon atom a is (S) stereochemistry;

the carbon atom b is (R) stereochemistry;

$R_4$ is phenyl($C_1$–$C_2$)alkyl, thien-2-yl-($C_1$–$C_2$)alkyl, thien-3-yl-($C_1$–$C_2$)alkyl, fur-2-yl-($C_1$–$C_2$)alkyl or fur-3-yl-($C_1$–$C_2$)alkyl wherein said rings are mono- or di-substituted independently with H or fluoro;

$R_{10}$ and $R_{11}$ are H;

$R_6$ is carboxy; and $R_7$ is H.

Preferred within the immediately preceding group is a compound wherein $R_1$ is 5-chloro;

$R_{10}$ and $R_{11}$ are H; and $R_4$ is benzyl.

A third group of preferred compounds of Formula I consists of those compounds wherein $R_1$ is H, halo, methyl or cyano;

$R_{10}$ and $R_{11}$ are each independently H or halo;

A is —C(H)=;

$R_2$ and $R_3$ are H;

$R_4$ is phenyl($C_1$–$C_2$)alkyl wherein said phenyl groups are mono-, di- or tri-substituted independently with H or halo or mono- or di- substituted independently with H, halo, ($C_1$–$C_4$)alkyl, ($C_1$–$C_4$)alkoxy, trifluoromethyl, hydroxy, amino or cyano; or $R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol -1-, -2-, -4- or -5-yl($C_1$–$C_2$)alkyl, fur-2- or -3-yl ($C_1$–$C_2$alkyl, pyrrol-2- or -3-yl($C_1$–$C_2$)alkyl, oxazol-2-, -4- or -5-yl-($C_1$–$C_2$)alkyl, pyrazol-3-, -4- or -5-yl ($C_1$–$C_2$)alkyl, isoxazol-3-, -4- or -5-yl($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;

$R_5$ is fluoro, ($C_1$–$C_4$)alkyl, ($C_1$–$C_5$)alkoxy, amino($C_1$–$C_4$) alkoxy, mono-N- or di-N,N-($C_1$–$C_4$)alkylamino ($C_1$–$C_4$)alkoxy, carboxy($C_1$–$C_4$)alkoxy, ($C_1$–$C_5$) alkoxy-carbonyl($C_1$–$C_4$)alkoxy, benzyloxycarbonyl ($C_1$–$C_4$)alkoxy;

$R_6$ is carboxy or ($C_1$–$C_8$)alkoxycarbonyl; and $R_7$ is H, fluoro or ($C_1$–$C_6$)alkyl.

A fourth group of preferred compounds of Formula I consists of those compounds wherein $R_1$ is H, halo, methyl or cyano;

$R_{10}$ and $R_{11}$ are each independently H or halo;

A is —C(H)=;

$R_2$ and $R_3$ are H;

$R_4$ is phenyl($C_1$–$C_2$)alkyl wherein said phenyl groups are mono-, di- or tri-substituted independently with H or halo or mono- or di- substituted independently with H, halo, ($C_1$–$C_4$)alkyl, ($C_1$–$C_4$)alkoxy, trifluoromethyl, hydroxy, amino or cyano; or $R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol -1-, -2-, -4- or -5-yl($C_1$–$C_2$)alkyl, fur-2- or -3-yl ($C_1$–$C_2$)alkyl pyrrol-2- or -3-yl($C_1$–$C_2$)alkyl, oxazol-2-, -4- or -5-yl-($C_1$–$C_2$)alkyl, pyrazol-3-, -4- or -5-yl ($C_1$–$C_2$)alkyl, isoxazol-3-, -4- or -5-yl($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;

$R_5$ is fluoro, ($C_1$–$C_4$)alkyl, ($C_1$–$C_5$)alkoxy, amino($C_1$–$C_4$) alkoxy, mono-N- or di-N,N-($C_1$–$C_4$)alkylamono ($C_1$–$C_4$)alkoxy, carboxy($C_1$–$C_4$)alkoxy, ($C_1$–$C_5$) alkoxy-carbonyl($C_1$–$C_4$)alkoxy, benzyloxycarbonyl ($C_1$–$C_4$)alkoxy;

$R_6$ is C(O)$NR_8R_9$ or C(O)$R_{12}$; and $R_7$ is H, fluoro or ($C_1$–$C_6$)alkyl.

A second group of glycogen phosphorylase inhibitors includes compounds of the Formula IA

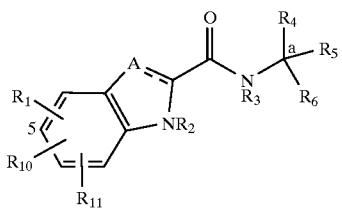

Formula IA and the pharmaceutically acceptable salts and prodrugs thereof wherein the dotted line (—) is an optional bond;

A is —C(H)=, —C((($C_1$–$C_4$)alkyl)=, —C(halo)= or —N=, when the dotted line (—) is a bond, or A is methylene or —CH(($C_1$–$C_4$)alkyl)-, when the dotted line (—) is not a bond;

$R_1$, $R_{10}$ or $R_{11}$ are each independently H, halo, cyano, 4-, 6-, or 7-nitro, ($C_1$–$C_4$)alkyl, ($C_1$–$C_4$)alkoxy, fluoromethyl, difluoromethyl or trifluoromethyl;

$R_2$ is H;

$R_3$ is H or ($C_1$–$C_5$)alkyl;

$R_4$ is H, methyl, ethyl, n-propyl, hydroxy($C_1$–$C_3$)alkyl, ($C_1$–$C_3$)alkoxy($C_1C_3$)alkyl, phenyl($C_1$–$C_4$)alkyl, phenylhydroxy($C_1$–$C_4$)alkyl, (phenyl)((($C_1$–$C_4$)-alkoxy)($C_1$–$C_4$)alkyl, thien-2- or -3-yl($C_1$–$C_4$)alkyl or fur-2- or -3-yl($C_1$–$C_4$)alkyl wherein said $R_4$ rings are mono-, di- or tri-substituted independently on carbon with H, halo, ($C_1$–$C_4$)alkyl, ($C_1$–$C_4$)alkoxy, trifluoromethyl, hydroxy, amino, cyano or 4,5-dihydro-1H-imidazol-2-yl;or $R_4$ is pyrid-2-, -3- or -4-yl($C_1$–$C_4$)alkyl, thiazol-2-, -4- or -5-yl($C_1$–$C_4$)alkyl, imidazol-2-, -4- or -5-yl($C_1$–$C_4$) alkyl, pyrrol-2- or -3-yl($C_1$–$C_4$)alkyl, oxazol-2-, -4- or -5-yl($C_1$–$C_4$)alkyl, pyrazol-3-, -4- or -5-yl($C_1{}_{-C4}$)alkyl, isoxazol-3-, -4- or -5-yl($C_1$–$C_4$)alkyl, isothiazol-3-, -4- or -5-yl($C_1$–$C_4$)alkyl, pyridazin-3- or -4-yl($C_1$–$C_4$) alkyl, pyrimidin-2-, -4-, -5- or -6-yl($C_1$–$C_4$)alkyl, pyrazin-2- or -3-yl($C_1$–$C_4$)alkyl, 1,3,5-triazin-2-yl ($C_1$–$C_4$)alkyl or indol-2-($C_1$–$C_4$)alkyl, wherein said preceding $R_4$ heterocycles are optionally mono- or di-substituted independently with halo, trifluoromethyl, ($C_1$–$C_4$)alkyl, ($C_1$–$C_4$)alkoxy, amino, hydroxy or cyano and said substituents are bonded to carbon; or $R_4$ is $R_{15}$-carbonyloxymethyl, wherein said $R_{15}$ is phenyl, thiazolyl, imidazolyl, 1H-indolyl, furyl, pyrrolyl, oxazolyl, pyrazolyl, isoxazolyl, isothiazolyl, pyridyl, pyridazinyl, pyrimidinyl, pyrazinyl or 1,3,5-triazinyl and wherein said preceding $R_{15}$ rings are optionally mono- or di-substituted independently with halo, amino, hydroxy, ($C_1$–$C_4$)alkyl, ($C_1$–$C_4$)alkoxy or trifluoromethyl and said mono- or di-substituents are bonded to carbon;

$R_5$ is H;

$R_6$ is carboxy, $(C_1-C_8)$alkoxycarbonyl, benzyloxycarbonyl, $C(O)NR_8R_9$ or $C(O)R_{12}$ wherein $R_8$ is H, $(C_1-C_6)$alkyl, cyclo$(C_3-C_6)$alkyl, cyclo$(C_3-C_6)$alkyl$(C_1-C_5)$alkyl, hydroxy or $(C_1-C_8)$alkoxy; and $R_9$ is H, cyclo$(C_3-C_8)$alkyl, cyclo$(C_3-C_8)$alkyl$(C_1-C_5)$alkyl, cyclo$(C_4-C_7)$alkenyl, cyclo$(C_3-C_7)$alkyl$(C_1-C_5)$alkoxy, cyclo$(C_3-C_7)$alkyloxy, hydroxy, methylene-perfluorinated$(C_1-C_8)$alkyl, phenyl, or a heterocycle wherein said heterocycle is pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl, 1,3,5-triazinyl, benzothiazolyl, benzoxazolyl, benzimidazolyl, thiochromanyl or tetrahydrobenzothiazolyl wherein said heterocycle rings are carbon-nitrogen linked; or $R_9$ is $(C_1-C_6)$alkyl or $(C_1-C_8)$alkoxy wherein said $(C_1-C_6)$alkyl or $(C_1-C_8)$alkoxy is optionally monosubstituted with cyclo$(C_4-C_7)$alken-1-yl, phenyl, thienyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, thiomorpholinyl, 1-oxothiomorpholinyl, 1,1-dioxothiomorpholinyl, pyridazinyl, pyrimidinyl, pyrazinyl, piperazinyl, 1,3,5-triazinyl or indolyl and wherein said $(C_1-C_6)$alkyl or $(C_1-C_8)$alkoxy are optionally additionally independently mono- or di-substituted with halo, hydroxy, $(C_1-C_5)$alkoxy, amino, mono-N- or di-N,N-$(C_1-C_5)$alkylamino, cyano, carboxy, or $(C_1C_4)$alkoxycarbonyl; and wherein the $R_9$ rings are optionally mono- or di-substituted independently on carbon with halo, $(C_1-C_4)$alkyl, $(C_1-C_4)$alkoxy, hydroxy, hydroxy$(C_1-C_4)$alkyl, amino$(C_1-C_4)$alkyl, mono-N- or di-N,N-$(C_1-C_4)$alkylamino$(C_1-C_4)$alkyl, $(C_1-C4)$alkoxy$(C_1-C_4)$alkyl, amino, mono-N- or di-N,N-$(C_1-C_4)$alkylamino, cyano, carboxy, $(C_1-C_5)$alkoxycarbonyl, carbamoyl, formyl or trifluoromethyl and said $R_9$ rings may optionally be additionally mono- or di-substituted independently with $(C_1-C_5)$alkyl or halo;

with the proviso that no quaternized nitrogen on any $R_9$ heterocycle is included;

$R_{12}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan2-yl, pyrazolidin-1-yl, isoxazolidin-2-yl, isothiazolidin-2-yl, 1,2-oxazetidin-2-yl, oxazolidin-3-yl, 3,4-dihydroisoquinolin-2-yl, 1,3-dihydroisoindol-2-yl, 3,4-dihydro-2H-quinol-1-yl, 2,3-dihydro-benzo[1,4]oxazin-4-yl, 2,3-dihydro-benzo[1,4]-thiazine-4-yl, 3,4-dihydro-2H-quinoxalin-1-yl, 3,4-dihydro-benzo[c][1,2]oxazin-1-yl, 1,4-dihydro-benzo[d][1,2]oxazin-3-yl, 3,4-dihydro-benzo[e][1,2]-oxazin-2-yl, 3H-benzo[d]isoxazol-2-yl, 3H-benzo[c]isoxazol-1-yl or azepan-1-yl, wherein said $R_{12}$ rings are optionally mono-, di- or tri-substituted independently with halo, $(C_1-C_5)$alkyl, $(C_1-C_5)$alkoxy, hydroxy, amino, mono-N- or di-N,N-$(C_1-C_5)$alkylamino, formyl, carboxy, carbamoyl, mono-N- or di-N,N-$(C_1-C_5)$alkylcarbamoyl, $(C_1-C_6)$alkoxy$(C_1-C_3)$alkoxy, $(C_1-C_5)$alkoxycarbonyl, benzyloxycarbonyl, $(C_1-C_5)$alkoxycarbonyl$(C_1-C_5)$alkyl, $(C_1-C_4)$alkoxycarbonylamino, carboxy$(C_1-C_5)$alkyl, carbamoyl$(C_1-C_5)$alkyl, mono-N- or di-N,N-$(C_1-C_5)$alkylcarbamoyl$(C_1-C_5)$alkyl, hydroxy$(C_1-C_5)$alkyl, $(C_1-C_4)$alkoxy$(C_1-C_4)$alkyl, amino$(C_1-C_4)$alkyl, mono-N- or di-N,N-$(C_1-C_4)$alkylamino$(C_1-C_4)$alkyl, oxo, hydroxyimino or $(C_1-C_6)$alkoxyimino and wherein no more than two substituents are selected from oxo, hydroxyimino or $(C_1-C_6)$alkoxyimino and oxo, hydroxyimino or $(C_1-C_6)$alkoxyimino are on non-aromatic carbon; and wherein said $R_{12}$ rings are optionally additionally mono- or di-substituted independently with $(C_1-C_5)$alkyl or halo;

with the proviso that when $R_6$ is $(C_1-C_5)$alkoxycarbonyl or benzyloxycarbonyl then $R_1$ is 5-halo, 5-$(C_1-C_4)$alkyl or 5-cyano and $R_4$ is (phenyl)(hydroxy)$(C_1-C_4)$alkyl, (phenyl)$((C_1-C_4)$alkoxy)$(C_1-C_4)$alkyl, hydroxymethyl or Ar$(C_1-C_2)$alkyl, wherein Ar is thien-2- or -3-yl, fur-2- or -3-yl or phenyl wherein said Ar is optionally mono- or di-substituted independently with halo; with the provisos that when $R_4$ is benzyl and $R_5$ is methyl, $R_{12}$ is not 4-hydroxy-piperidin-1-yl or when $R_4$ is benzyl and $R_5$ is methyl $R_6$ is not $C(O)N(CH_3)_2$;

with the proviso that when $R_1$ and $R_{10}$ and $R_{11}$ are H, $R_4$ is not imidazol-4-ylmethyl, 2-phenylethyl or 2-hydroxy-2-phenylethyl;

with the proviso that when $R_8$ is H and $R_9$ is $(C_1-C_6)$alkyl, $R_9$ is not substituted with carboxy or $(C_1-C_4)$alkoxycarbonyl on the carbon which is attached to the nitrogen atom N of $NHR_9$; and with the proviso that when $R_6$ is carboxy and $R_1$, $R_{10}$, $R_{11}$ and $R_5$ are all H, then $R_4$ is not benzyl, H, (phenyl)(hydroxy)methyl, methyl, ethyl or n-propyl.

A first group of preferred compounds of Formula IA consists of those compounds wherein $R_1$ is 5-H, 5-halo, 5-methyl, 5-cyano or 5-trifluoromethyl;

$R_{10}$ and $R_{11}$ are each independently H or halo;

A is —C(H)=;

$R_2$ and $R_3$ are H;

$R_4$ is H, methyl, phenyl$(C_1-C_2)$alkyl, wherein said phenyl groups are mono- or di-substituted independently with H, halo, $(C_1-C_4)$alkyl, $(C_1-C_4)$alkoxy, trifluoromethyl, hydroxy, amino or cyano and wherein said $R_4$ groups are optionally additionally mono-substituted with halo; or $R_4$ is thien-2- or -3-yl$(C_1-C_2)$alkyl, pyrid-2-, -3- or -4-yl$(C_1-C_2)$alkyl, thiazol-2-, -4- or -5-yl$(C_1-C_2)$alkyl, imidazol-2-, -4- or -5-yl$(C_1-C_2)$alkyl, fur-2- or -3-yl$(C_1-C_2)$alkyl, pyrrol-2- or -3-yl$(C_1-C_2)$alkyl, oxazol-2-, -4- or -5-yl$(C_1-C_2)$alkyl, pyrazol-3-, -4- or -5-yl$(C_1-C_2)$alkyl, isoxazol-3-, -4- or -5-yl$(C_1-C_2)$alkyl, isothiazol-3-, -4- or -5-yl$(C_1C_2)$alkyl, pyridazin-3- or -4-yl$(C_1-C_2)$alkyl, pyrimidin-2-, -4-, -5- or -6-yl$(C_1-C_2)$alkyl, pyrazin-2- or -3-yl$(C_1-C_2)$alkyl or 1,3,5-triazin-2-yl$(C_1-C_2)$alkyl wherein said preceding $R_4$ heterocycles are optionally mono- or di-substituted independently with halo, trifluoromethyl, $(C_1-C_4)$alkyl, $(C_1-C_4)$alkoxy, amino or hydroxy and said mono- or di-substituents are bonded to carbon;

$R_5$ is H; and $R_6$ is $C(O)NR_8R_9$ or $C(O)R_{12}$.

Within the above first group of preferred compounds of Formula I is a first group of especially preferred compounds wherein $R_4$ is H, phenyl($C_1$–$C_2$)alkyl, thien-2- or -3-yl($C_1$–$C_2$)alkyl, fur-2- or -3-yl($C_1$–$C_2$)alkyl wherein said $R_4$ rings are mono- or di-substituted independently with H or fluoro;

$R_6$ is C(O)$R_{12}$; and $R_{12}$ is morpholino, thiomorpholino, 1-oxothiomorpholino, 1,1dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan2-yl, isoxazolidin-2-yl, isothiazolidin-2-yl, 1,2-oxazetidin-2-yl, oxazolidin-3-yl, 1,3dihydroisoindol-2-yl or azepan-1-yl, wherein said $R_{12}$ rings are optionally mono- or di-substituted independently with halo, ($C_1$–$C_5$)alkyl, ($C_1$–$C_5$)alkoxy, hydroxy, amino, mono-N- or di-N,N-($C_1C_5$)alkylamino, formyl, carboxy, carbamoyl, mono-N- or di-N,N-($C_1$–$C_5$)alkylcarbamoyl, ($C_1$–$C_5$)alkoxycarbonyl, hydroxy($C_1$–$C_5$)alkyl, amino($C_1$–$C_4$)alkyl, mono-N- or di-N,N($C_1$–$C_4$)alkylamino ($C_1$–$C_4$)alkyl, oxo, hydroxyimino or ($C_1$–$C_6$)alkoxyimino with the proviso that only the $R_{12}$ heterocycles thiazolidin-3-yl, pyrrolidin-1-yl, piperidin-1-yl, piperazin-1-yl, piperazin-4-yl, azetidin-1-yl, 1,2-oxazinan-2-yl, isoxazolidin-2-yl, or oxazolidin-3-yl are optionally mono- or di-substituted with oxo, hydroxyimino, or ($C_1$–$C_6$)alkoxyimino; and wherein said $R_{12}$ rings are optionally additionally mono- or di-substituted independently with ($C_1$–$C_5$)alkyl.

Within the above group of especially preferred compounds are the compounds

5-Chloro-1H-indole-2-carboxylic acid [(1S)-benzyl-2-(3-hydroxyimino-pyrrolidin-1-yl)-2 -oxo-ethyl]-amide, 5-Chloro-1H-indole-2-carboxylic acid [2-(cis-3,4-dihydroxy-pyrrolidin-1-yl)-2-oxo-ethyl]-amide, 5-Chloro-1H-indole-2-carboxylic acid [2-((3S,4S)-dihydroxy-pyrrolidin-1-yl)-2oxo-ethyl]-amide, 5-Chloro-1H-indole-2-carboxylic acid [(1S)-benzyl-2-(cis-3,4-dihydroxy pyrrolidin-1-yl)-2-oxo-ethyl]-amide, 5-Chloro-1H-indole-2-carboxylic acid [2-(1,1-dioxo-thiazolidin-3-yl)-2-oxo-ethyl]-amide, 5-Chloro-1H-indole-2-carboxylic acid (2-oxo-2-thiazolidin-3-yl-ethyl)-amide, 5-Chloro-1H-indole-2-carboxylic acid [(1S)-(4-fluoro-benzyl)-2-(4-hydroxy-piperidin-1-yl)-2-oxo-ethyl]-amide, 5-Chloro-1H-indole-2-carboxylic acid [(1S)-benzyl-2-((3RS)-hydroxy-piperidin-1-yl)-2-oxo-ethyl]-amide, 5-Chloro-1H-indole-2-carboxylic acid [2-oxo-2-((1 RS)-oxo-1-thiazolidin-3-yl)ethyl]-amide, 5-Chloro-1H-indole-2-carboxylic acid [(1S)-(2-fluoro-benzyl)-2-(4-hydroxy-piperidin-1-yl)-2-oxo-ethyl]-amide, 5-Chloro-1H-indole-2-carboxylic acid [(1 S)-benzyl-2-((3S,4S)-dihydroxy-pyrrolidin-1-yl)-2-oxo-ethyl]-amide, 5-Chloro-1H-indole-2-carboxylic acid [(1S)-benzyl-2-(3-hydroxy-azetidin-1-yl)2-oxo-ethyl]-amide, 5-Chloro-1H-indole-2-carboxylic acid [(1S)-benzyl-2-(3-hydroxyimino-azetidin-1-yl)-2-oxo-ethyl]-amide, 5-Chloro-1H-indole-2-carboxylic acid [(1S)-benzyl-2-(4-hydroxyimino-piperidin-1-yl)-2-oxo-ethyl]-amide, or 5-Chloro-1H-indole-2-carboxylic acid [1-benzyl-2-(3-hydroxypyrrolidin-1-yl)-2-oxo-ethyl]amide.

Within the above group of especially preferred compounds is a first group of particularly preferred compounds wherein $R_4$ is H; and $R_{12}$ is thiazolidin-3-yl, 1-oxo-thiazolidin-3-yl, 1,1-dioxothiazolidin-3-yl or oxazolidin-3-yl or said $R_{12}$ substituents optionally mono- or di-substituted independently with carboxy, ($C_1$–$C_5$)alkoxycarbonyl, hydroxy($C_1$–$C_3$)alkyl, amino($C_1$–$C_3$)alkyl, mono-N- or di-N,N-($C_1$–$C_3$) alkylamino($C_1$–$C_3$)alkyl or $R_{12}$ is mono- or di-substituted pyrrolidin-1-yl wherein said substituents are independently carboxy, ($C_1$–$C_5$) alkoxycarbonyl, ($C_1$–$C_5$)alkoxy, hydroxy, hydroxy ($C_1$–$C_3$)alkyl, amino, amino($C_1$–$C_3$)alkyl, mono-N- or di-N,N-($C_1$–$C_3$)alkylamino($C_1$–$C_3$)alkyl or mono-N- or di-N,N-($C_1$–$C_4$)alkylamino; and the $R_{12}$ rings are optionally additionally independently di-substituted with ($C_1$–$C_5$)alkyl.

Preferred compounds within the immediately preceding group of particularly preferred compounds are compounds wherein a. $R_1$ is 5-chloro;
$R_{10}$ and $R_{11}$ are H; and
$R_{12}$ is cis-3,4-dihydroxy-pyrrolidin-1-yl;

b. $R_1$ is 5-chloro;
$R_{10}$ and $R_{11}$ are H; and
$R_{12}$ is (3S,4S)-dihydroxy-pyrrolidin-1-yl;

c. $R_1$ is 5-chloro;
$R_{10}$ and $R_{11}$ are H; and
$R_{12}$ is 1,1-dioxo-thiazolidin-3-yl;

d. $R_1$ is 5-chloro;
$R_{10}$ and $R_{11}$ are H; and
$R_{12}$ is 1-oxo-thiazolidin-3-yl; and e. $R_1$ is 5-chloro;
$R_{10}$ and $R_{11}$ are H; and
$R_{12}$ is 1-oxo-thiazolidin-3-yl.

Within the above group of especially preferred compounds is a second group of particularly preferred compounds wherein $R_4$ is phenylmethyl, thien-2- or -3-ylmethyl wherein said $R_4$ rings are optionally mono- or di-substituted with fluoro; and $R_{12}$ is thiazolidin-3-yl, 1-oxo-thiazolidin-3-yl, 1,1-dioxothiazolidin-3-yl or oxazolidin-3-yl or said $R_{12}$ substituents optionally mono- or di-substituted independently with carboxy or ($C_1$–$C_5$)alkoxycarbonyl, hydroxy ($C_1$–$C_3$)alkyl, amino($C_1$–$C_3$)alkyl or mono-N- or di-N,N-($C_1$–$C_3$)alkylamino($C_1$–$C_3$)alkyl or $R_{12}$ is mono- or di-substituted azetidin-1-yl or mono- or di-substituted pyrrolidin-1-yl or mono- or di-substituted piperidin-1-yl wherein said substituents are independently carboxy, ($C_1$–$C_5$)alkoxycarbonyl, hydroxy($C_1$–$C_3$)alkyl, amino($C_1$–$C_3$)alkyl,, mono-N- or di-N,N-($C_1$–$C_3$)alkylamino($C_1$–$C_3$)alkyl, hydroxy, ($C_1$–$C_5$)alkoxy, amino, mono-N- or di-N,N-($C_1$–$C_5$) alkylamino, oxo, hydroxyimino or ($C_1$–$C_5$) alkoxyimino; and the $R_{12}$ rings are optionally additionally mono- or di-substituted independently with ($C_1$–$C_5$)alkyl.

Preferred compounds within the immediately preceding group of particularly preferred compounds are compounds wherein a. $R_1$ is 5-chloro;
$R_{10}$ and $R_{11}$ are H;
$R_4$ is 4-fluorobenzyl;

$R_{12}$ is 4-hydroxypiperidin-1-yl; and
the stereochemistry of carbon (a) is (S);

b. $R_1$ is 5-chloro;
$R_{10}$ and $R_{11}$ are H;
$R_4$ is benzyl;
$R_{12}$ is 3-hydroxypiperidin-1-yl; and
the stereochemistry of carbon (a) is (S);

c. $R_1$ is 5-chloro;
$R_{10}$ and $R_{11}$ are H;
$R_4$ is benzyl;
$R_{12}$ is cis-3,4-dihydroxy-pyrrolidin-1-yl; and
the stereochemistry of carbon (a) is S;

d. $R_1$ is 5-chloro;
$R_{10}$ and $R_{11}$ are H; $R_4$ is benzyl;
$R_{12}$ is 3-hydroxyimino-pyrrolidin-1-yl; and
the stereochemistry of carbon (a) is (S);

e. $R_1$ is 5-chloro;
$R_{10}$ and $R_{11}$ are H;
$R_4$ is 2-fluorobenzyl;
$R_{12}$ is 4-hydroxypiperidin-1-yl; and
the stereochemistry of carbon (a) is (S);

f. $R_1$ is 5-chloro;
$R_{10}$ and $R_{11}$ are H;
$R_4$ is benzyl;
$R_{12}$ is (3S,4S)-dihydroxy-pyrrolidin-1-yl; and the stereochemistry of carbon (a) is (S);

g. $R_1$ is 5-chloro;
$R_{10}$ and $R_{11}$ are H;
$R_4$ is benzyl;
$R_{12}$ is 3-hydroxy-azetidin-1-yl; and
the stereochemistry of carbon (a) is (S);

h. $R_1$ is 5-chloro;
$R_{10}$ and $R_{11}$ are H;
$R_4$ is benzyl;
$R_{12}$ is 3-hydroxyimino-azetidin-1-yl; and
the stereochemistry of carbon (a) is (S); and i. $R_1$ is 5-chloro;
$R_{10}$ and $R_{11}$ are H;
$R_4$ is benzyl;
$R_{12}$ is 4-hydroxyimino-piperidin-1-yl; and
the stereochemistry of carbon (a) is (S).

A second group of especially preferred compounds within the first group of preferred compounds are the compounds wherein $R_4$ is H, phenyl($C_1$–$C_2$)alkyl, thien-2- or -3-yl($C_1$–$C_2$) alkyl, fur-2- or -3-yl($C_1$–$C_2$)alkyl wherein said $R_4$ rings are mono- or di-substituted independently with H or fluoro;

$R_6$ is C(O)N$R_8R_9$; and $R_8$ is H, ($C_1$–$C_5$)alkyl, hydroxy or ($C_1$–$C_4$)alkoxy; and $R_9$ is H, cyclo($C_4$–$C_6$)alkyl, cyclo($C_3$–$C_6$)alkyl($C_1$–$C_5$)alkyl, methylene-perfluorinated($C_1$–$C_3$)alkyl, pyridyl, pyrrolidinyl, oxazolyl, thiazolyl, imidazolyl, piperidinyl, benzothiazolyl or thiochromanyl; or $R_9$ is ($C_1$–$C_5$)alkyl wherein said ($C_1$–$C_5$)alkyl is optionally substituted with cyclo($C_4$–$C_6$)alkenyl, phenyl, thienyl, pyridyl, pyrrolidinyl, oxazolyl, thiazolyl, imidazolyl, pyrazolyl, piperidinyl, morpholinyl, thiomorpholinyl, 1-oxothiomorpholinyl, or 1,1-dioxothiomorpholinyl and wherein said ($C_1$–$C_5$)alkyl or ($C_1$–$C_4$)alkoxy is optionally additionally independently mono- or di-substituted with halo, hydroxy, ($C_1$–$C_5$)alkoxy, amino, mono-N- or di-N,N-($C_1$–$C_5$) alkylamino, cyano, carboxy, or ($C_1$–$C_4$) alkoxycarbonyl; and wherein the $R_9$ rings are optionally mono- or di-substituted independently on carbon with halo, ($C_1$–$C_4$)alkyl, ($C_1$–$C_4$)alkoxy, hydroxy, amino, mono-N- or di-N,N-($C_1C_4$)alkylamino, carbamoyl, ($C_1$–$C_5$) alkoxycarbonyl or carbamoyl.

Within the immediately preceding second group of especially preferred compounds are the compounds wherein a. $R_1$ is 5-chloro;
$R_{10}$ and $R_{11}$ are H;
$R_4$ is benzyl;
$R_8$ is methyl; and
$R_9$ is 3-(dimethylamino)propyl;

b. the stereochemistry of carbon (a) is (S);
$R_1$ is 5-chloro;
$R_{10}$ and $R_{11}$ are H;
$R_4$ is benzyl;
$R_8$ is methyl; and
$R_9$ is 3-pyridyl;

c. the stereochemistry of carbon (a) is (S);
$R_1$ is 5-chloro;
$R_{10}$ and $R_{11}$ are H;
$R_4$ is benzyl;
$R_8$ is methyl; and
$R_9$ is 2-hydroxyethyl; and d. the stereochemistry of carbon (a) is (S);
$R_1$ is 5-fluoro;
$R_{10}$ and $R_{11}$ are H;
$R_4$ is 4-fluorophenylmethyl;
$R_8$ is methyl; and
$R_9$ is 2-morpholinoethyl.

A third group of especially preferred compounds within the first group of preferred compounds are the compounds wherein $R_4$ is H, phenyl($C_1$–$C_2$)alkyl, thien-2- or -3-yl($C_1$–$C_2$) alkyl, fur-2- or -3-yl($C_1$–$C_2$)alkyl wherein said $R_4$ rings are mono- or di-substituted independently with H or fluoro;

$R_6$ is C(O)N$R_8R_9$; and $R_8$ is H, ($C_1$–$C_5$)alkyl, hydroxy or ($C_1$–$C_4$)alkoxy; and $R_9$ is ($C_1$–$C_4$)alkoxy wherein said ($C_1$–$C_4$)alkoxy is optionally substituted with cyclo($C_4$–$C_6$)alkenyl, phenyl, thienyl, pyridyl, pyrrolidinyl, oxazolyl, thiazolyl, imidazolyl, pyrazolyl, piperidinyl, morpholinyl, thiomorpholinyl, 1-oxothiomorpholinyl, or 1,1- dioxothiomorpholinyl and wherein said ($C_1$–$C_5$)alkyl or ($C_1$–$C_4$) alkoxy is optionally additionally independently mono- or di-substituted with halo, hydroxy, ($C_1$–$C_5$)alkoxy, amino, mono-N- or di-N,N-($C_1$–$C_5$)alkylamino, cyano, carboxy, or ($C_1$–$C_4$)alkoxycarbonyl; and wherein the $R_9$ rings are optionally mono- or di-substituted independently on carbon with halo, ($C_1$–$C_4$)alkyl, ($C_1$–$C_4$)alkoxy, hydroxy, amino, mono-N- or di-N,N-($C_1C_4$)alkylamino, carbamoyl, ($C_1$–$C_5$) alkoxycarbonyl or carbamoyl.

Within the immediately preceding third group of especially preferred compounds are the compounds wherein a. $R_1$ is 5-chloro;
$R_{10}$ and $R_{11}$ are H;
$R_4$ is benzyl;
$R_8$ is methyl; and
$R_9$ is 2-hydroxyethoxy;

b. the stereochemistry of carbon (a) is (S);
$R_{10}$ is 5-chloro;
$R_{10}$ and $R_{11}$ are H;
$R_4$ is 4-fluorophenylmethyl;

$R_8$ is methyl; and
$R_9$ is methoxy;
c. the stereochemistry of carbon (a) is (S);
$R_1$ is 5-chloro;
$R_{10}$ and $R_{11}$ are H;
$R_4$ is benzyl;
$R_8$ is methyl; and
$R_9$ is methoxy;

A second group of preferred compounds of Formula IA are those compounds wherein
$R_1$ is 5-halo, 5-methyl, 5-cyano or trifluoromethyl;
$R_{10}$ and $R_{11}$ are each independently H or halo;
A is —C(H)=;
$R_2$ and $R_3$ are H;
$R_4$ is H, phenyl($C_1$–$C_2$)alkyl, thien-2- or -3-yl($C_1$–$C_2$) alkyl, fur-2- or -3-yl($C_1$–$C_2$)alkyl wherein said rings are mono- or di-substituted independently with H or fluoro;
$R_5$ is H; and
$R_6$ is ($C_1$–$C_5$)alkoxycarbonyl.

A third group of preferred compounds of Formula IA are those compounds wherein
$R_1$ is 5-halo, 5-methyl, 5-cyano or trifluoromethyl;
$R_{10}$ and $R_{11}$ are each independently H or halo;
A is —C(H)=;
$R_2$ and $R_3$ are H;
$R_4$ is H, methyl or phenyl($C_1$–$C_2$)alkyl, wherein said phenyl groups are mono- or di-substituted independently with H, halo, ($C_1$–$C_4$)alkyl, ($C_1$–$C_4$)alkoxy, trifluoromethyl, hydroxy, amino or cyano and wherein said phenyl groups are additionally mono- or di-substituted independently H or halo; or
$R_4$ is thien-2- or -3-yl($C_1$–$C_2$)alkyl, pyrid-2-, -3- or -4-yl ($C_1$–$C_2$)alkyl, thiazol-2-4- or -5-yl($C_1$–$C_2$)alkyl, imidazol-2-, -4- or -5-yl($C_1$–$C_2$)alkyl, fur-2- or -3-yl ($C_1$–$C_2$)alkyl, pyrrol-2- or -3-yl($C_1$–$C_2$)alkyl, oxazol-2-, -4- or -5-yl($C_1$–$C_2$)alkyl, pyrazol-3-, -4- or -5-yl ($C_1$–$C_2$)alkyl, isoxazol-3-, -4- or -5-yl($C_1$–$C_2$)alkyl, isothiazol-3-, -4- or -5-yl($C_1C_2$)alkyl, pyridazin-3- or -4-yl($C_1$–$C_2$)alkyl, pyrimidin-2-, -4-, -5- or -6-yl ($C_1$–$C_2$)alkyl, pyrazin-2- or -3-yl($C_{1-C2}$)alkyl or 1,3,5-triazin-2-yl($C_1$–$C_2$)alkyl wherein said preceding $R_4$ heterocycles are optionally mono- or di-substituted independently with halo, trifluoromethyl, ($C_1$–$C_4$) alkyl, ($C_1$–$C_4$)alkoxy, amino or hydroxy and said mono- or di-substituents are bonded to carbon;
$R_5$ is H; and
$R_6$ is carboxy.

Within the third group of preferred compounds is a first group of especially preferred compounds wherein
$R_{10}$ and $R_{11}$ are H; and
$R_4$ is H.

Particularly preferred within the immediately preceding especially preferred group is a compound wherein
$R_1$ is 5-chloro.

A preferred aspect of this invention is a method of reducing brain damage resulting from cerebral ischemia.

Yet another preferred aspect of this invention is a method of reducing liver damage resulting from hepatic ischemia.

Yet another preferred aspect of this invention is a method of reducing kidney damage resulting from renal ischemia.

Yet another preferred aspect of this invention is a method of reducing lung damage resulting from pulmonary ischemia.

Yet another preferred aspect of this invention is a method of reducing gastric damage resulting from gastric ischemia.

Yet another preferred aspect of this invention is a method of reducing intestinal damage resulting from intestinal ischemia.

Yet another preferred aspect of this invention is a method of reducing skeletal muscle damage resulting from skeletal muscle ischemia.

Yet another preferred aspect of this invention is a method of reducing spleen damage resulting from splenic ischemia.

Yet another preferred aspect of this invention is a method of reducing pancreas damage resulting from pancreatic ischemia.

Yet another preferred aspect of this invention is a method of reducing retinal damage resulting from retinal ischemia.

Yet another preferred aspect of this invention is a method of reducing spinal cord or nerve damage resulting from spinal cord or nerve ischemia.

Yet another preferred aspect of this invention is a method of reducing vascular damage resulting from ischemia.

The term "reduction" is intended to include partial prevention or prevention which, although greater than that which would result from taking no drug or from taking placebo, is less than 100% in addition to substantially total prevention.

The term "damage resulting from ischemia" as employed herein refers to conditions associated with reduced blood flow or reduced oxygenation to non-cardiac tissue, for example due to a clot or obstruction of blood vessels which supply blood to the subject tissue and which result, inter alia, in lowered oxygen transport to such tissue, impaired tissue performance, tissue dysfunction and necrosis. In addition, the damage may also be due to tissue hypoxia independent of ischemia.

Those skilled in the art will recognize that this invention also includes improvement of tissue performance (e.g., the ability to sustain normal muscle function is enhanced during ischemia). For example, a human could walk a further distance before having to stop from skeletal muscle pain.

The term glycogen phosphorylase inhibitor refers to any substance or agent or any combination of substances and/or agents which reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose1-phosphate and a glycogen macromolecule which is one glucosyl residue shorter than the original glycogen macromolecule (forward direction of glycogenolysis).

The term "treating" as used herein includes preventative (e.g., prophylactic) and palliative treatment.

By halo is meant chloro, bromo, iodo, or fluoro.

By alkyl is meant straight chain or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, hexyl and isohexyl.

By alkoxy is meant straight chain or branched saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, hexoxy and isohexoxy.

The expression "pharmaceutically-acceptable anionic salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluene-sulfonate.

The expression "pharmaceutically-acceptable cationic salt" refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol).

The expression "prodrug" refers to any compound that is a drug precursor, which, following administration, releases the drug via any chemical or physiological process (e.g., a prodrug on being brought to the physiological pH is converted to the desired drug form). Exemplary prodrugs upon cleavage release the corresponding free acid, and such hydrolyzable ester-forming residues of the compounds of this invention include but are not limited to carboxylic acid substituents.

As used herein, the expressions "reaction-inert solvent" and "inert solvent" refers to a solvent which does not interact with starting materials, reagents, intermediates or products in a manner which adversely affects the yield of the desired product.

The chemist of ordinary skill will recognize that certain compounds of this invention will contain one or more atoms which may be in a particular stereochemical or geometric configuration, giving rise to stereoisomers and configurational isomers. All such isomers and mixtures thereof are included in this invention. Hydrates of the compounds of this invention are also included.

The chemist of ordinary skill will recognize that certain combinations of heteroatom-containing substituents listed in this invention define compounds which will be less stable under physiological conditions (e.g. those containing acetal or animal linkages). Accordingly, such compounds are less preferred.

The term "$R_x$ ring" wherein x is an integer, for example "$R_9$ ring", "$R_{12}$ ring" or "$R_4$ ring" as used herein in reference to substitution on the ring refers to moieties wherein the ring is $R_x$ and also wherein the ring is contained within $R_x$.

As used herein the term mono-N- or di-N,N- ($C_1$–$C_x$) alkyl . . . refers to the ($C_1C_x$) alkyl moiety taken independently when it is di-N,N-($C_1$–$C_x$) alkyl . . . ; (x refers to an integer).

DETAILED DESCRIPTION OF THE INVENTION

Any glycogen phosphorylase inhibitor may be used as a compound (active agent) of this invention. Such inhibition is readily determined by those skilled in the art according to standard assays (for example, M. A. Pesce, et al. (1977) Clinical Chemistry 23:1711–1717). A variety of glycogen phosphorylase inhibitors are described above, however, other glycogen phosphorylase inhibitors will be known to those skilled in the art (e.g., WO 95/24391-A1).

In general the compounds of Formula I and IA can be made by processes which include processes known in the chemical arts, particularly in light of the description contained herein. Certain processes for the manufacture of Formula I and IA compounds are provided as further features of the invention and are illustrated by the following reaction schemes.

SCHEME I

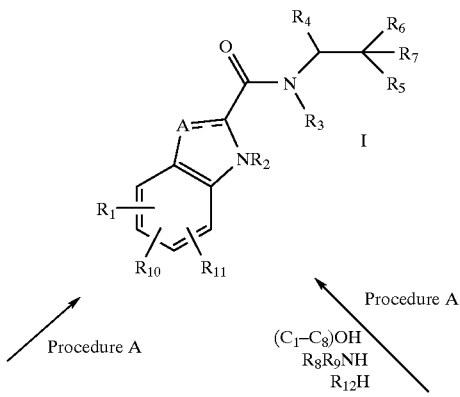

-continued
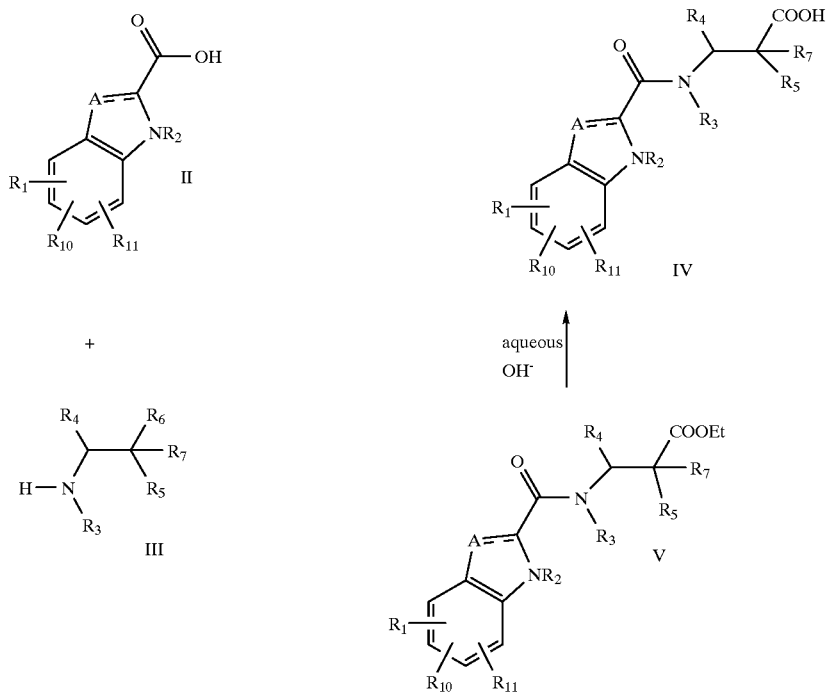
SCHEME II
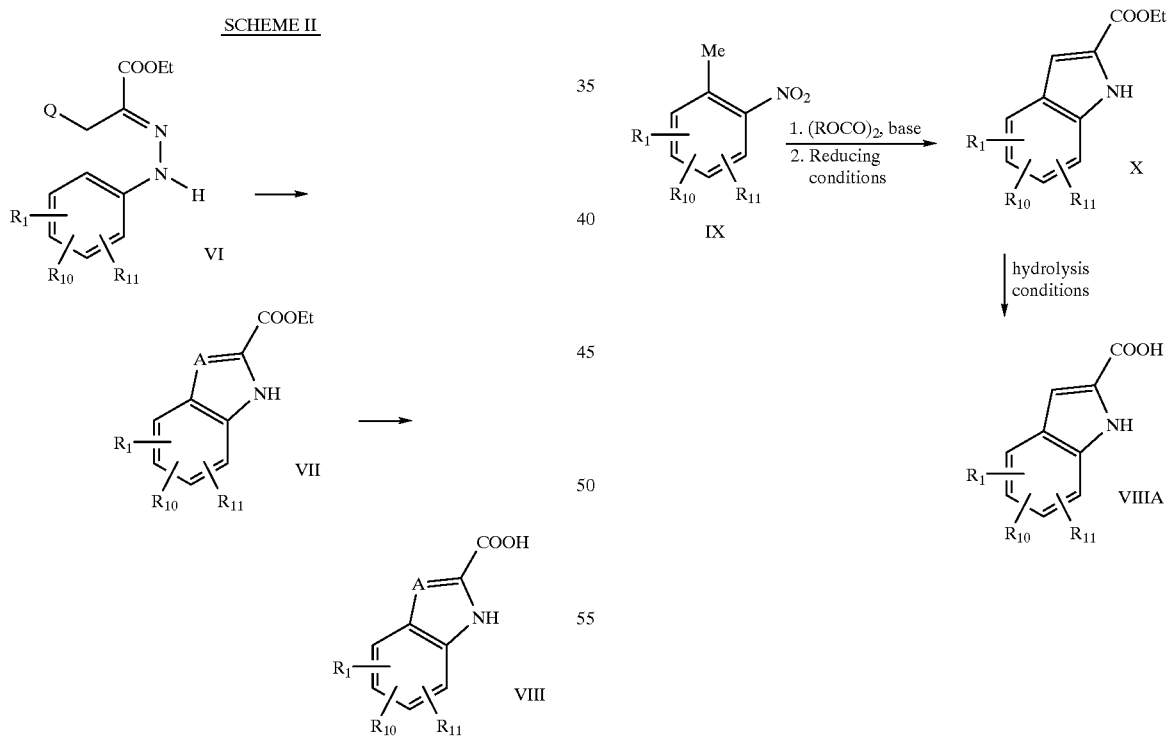

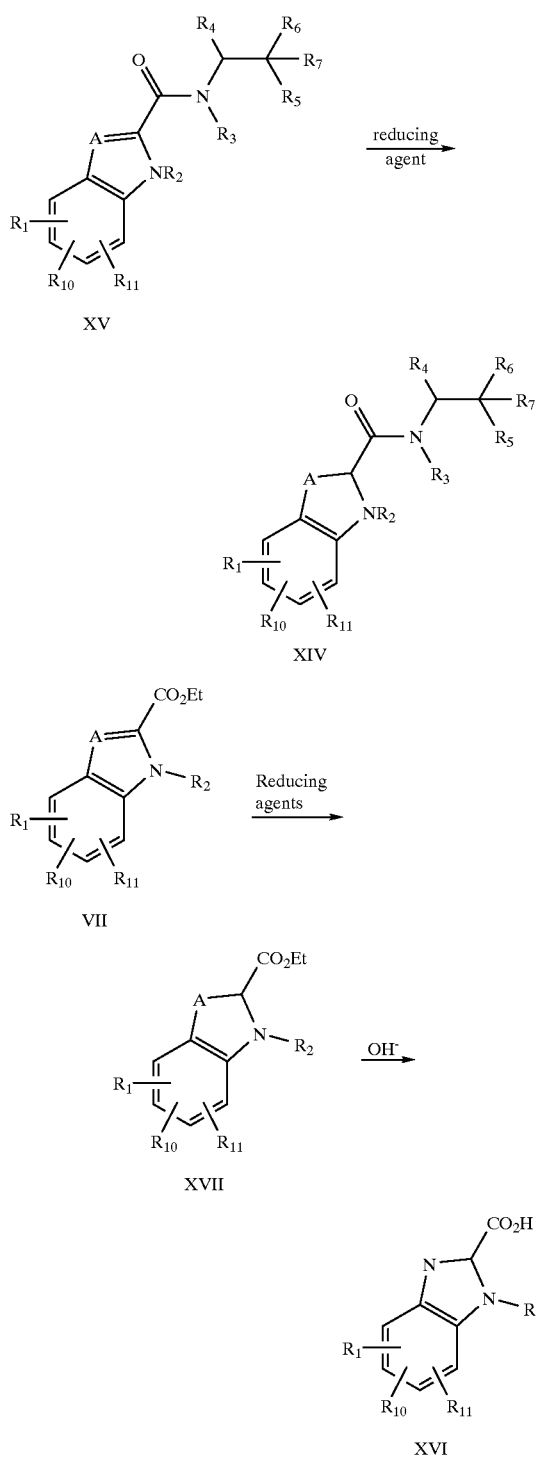
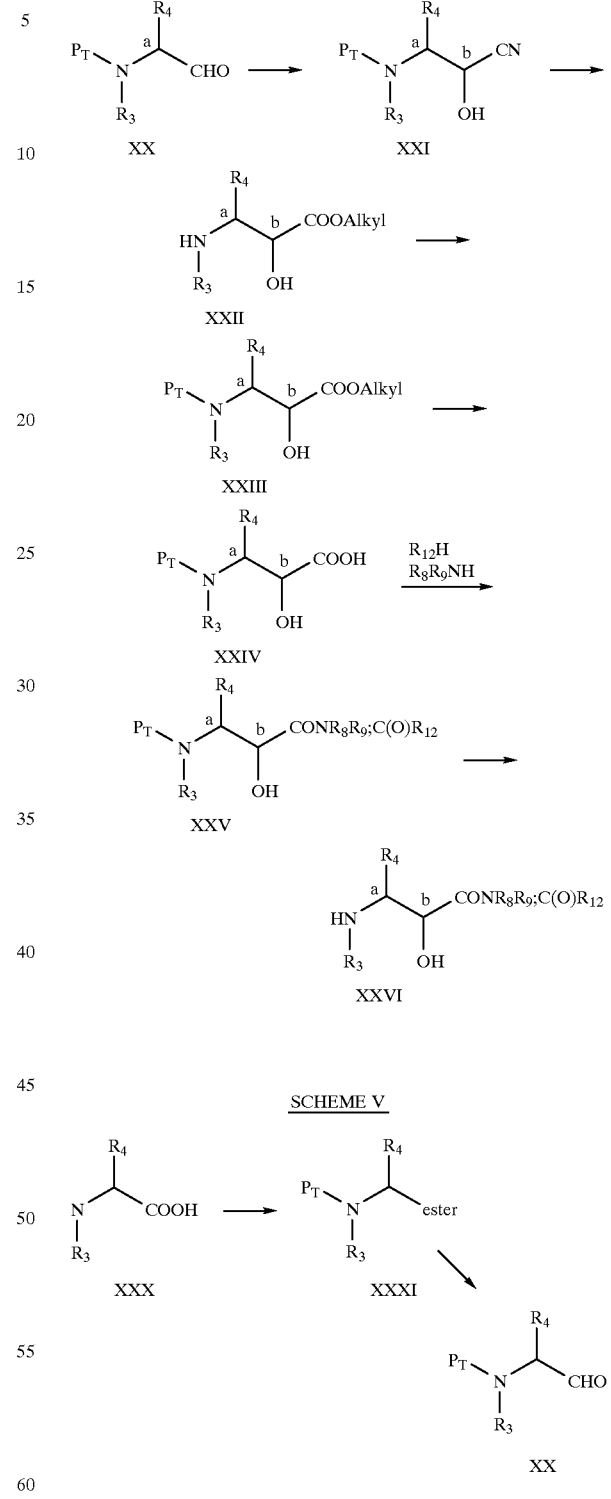

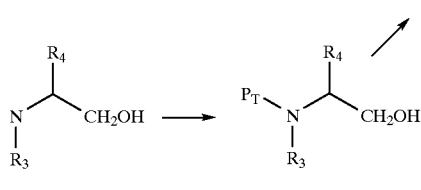
XXXII → XXXIII
SCHEME VI
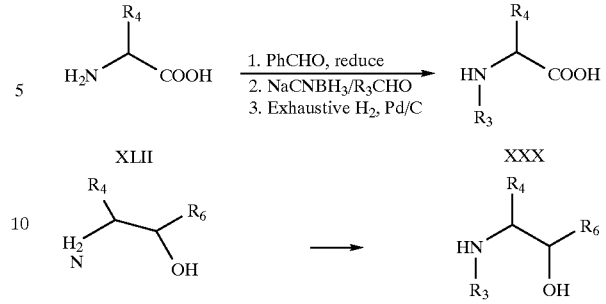
XLII → XXX
XLIV → XLV
IIIA → III
SCHEME VII
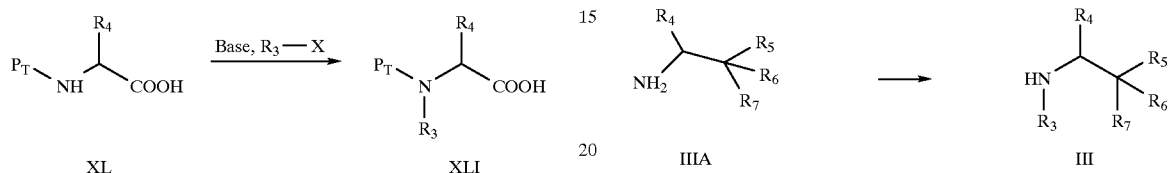
L → LI → LII
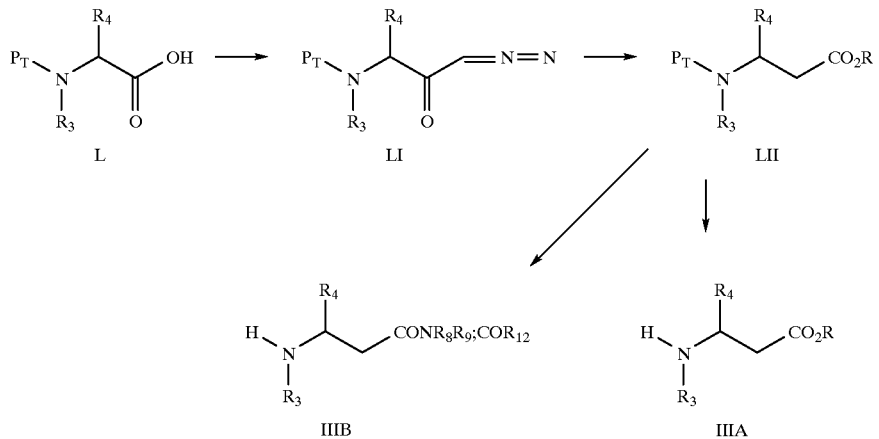
IIIB    IIIA SCHEME VIII
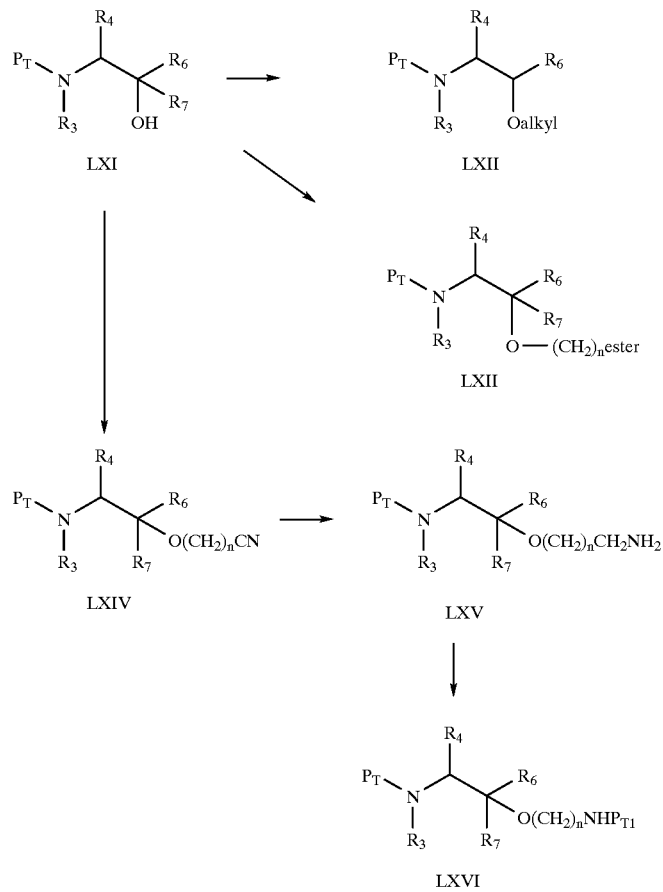
SCHEME IX
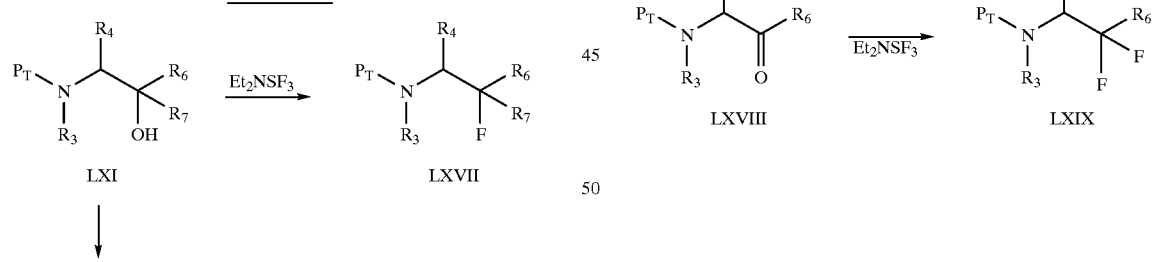

SCHEME X

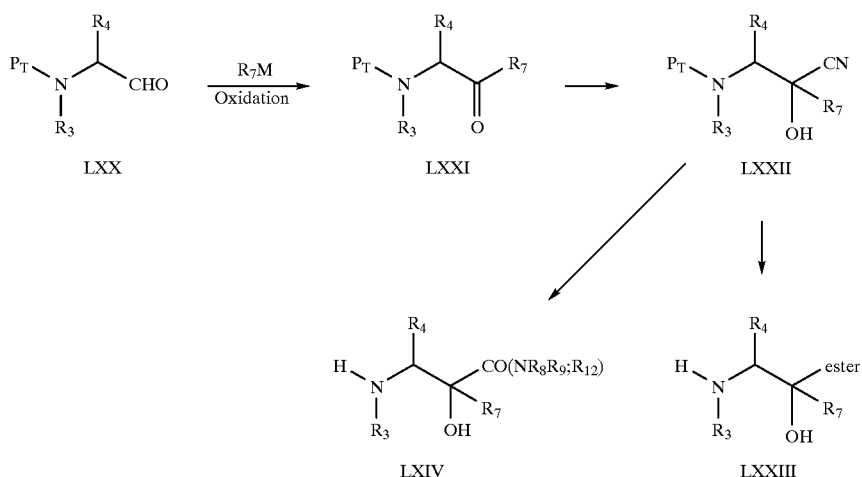

According to Reaction Scheme I the Formula I compounds, wherein $R_1$, $R_{10}$, $R_{11}$, A, $R_2$, $R_3$, $R_4$, $R_5$, $R_6$ and $R_7$ are as defined above may be prepared by either of two general processes. In the first process the desired Formula I compound may be prepared by coupling the appropriate Formula I indole-2-carboxylic acid or indoline-2-carboxylic acid with the appropriate Formula III amine (i.e., acylating the amine). In the second process the desired Formula I compound may be prepared by coupling the appropriate Formula IV compound (i.e., a Formula I compound wherein $R_6$ is carboxy) with the appropriate alcohol or formula $R_8R_9NH$ or $R_{12}H$ amine or alcohol, wherein $R_8$, $R_9$ and $R_{12}$ are as defined above (i.e., acylating the amine or alcohol).

Typically, the Formula II compound is combined with the Formula III compound (or Formula IV compound is combined with the appropriate amine (e.g., $R_{12}H$ or $R_8R_9NH$)) or alcohol in the presence of a suitable coupling agent. A suitable coupling agent is one which transforms a carboxylic acid into a reactive species which forms an amide or ester linkage on reaction with an amine or alcohol, respectively.

The coupling agent may be a reagent which effects this condensation in a one pot process when mixed together with the carboxylic acid and amine or alcohol. If the acid is to be condensed with an alcohol it is preferable to employ a large excess of the alcohol as the reaction solvent, with or without 1.0 to 1.5 equivalent added dimethylaminopyridine. Exemplary coupling reagents are 1-(3-dimethylaminopropyl)3-ethylcarbodiimide hydrochloride-hydroxybenzotriazole (DEC/HBT), carbonyldiimidazole, dicyclohexylcarbodiimide/hydroxybenzotriazole (HBT), 2-ethoxy1-ethoxycarbonyl-1,2-dihydroquinoline (EEDQ), carbonyldiimidazole/HBT, and diethylphosphorylcyanide. The coupling is performed in an inert solvent, preferably an aprotic solvent at a temperature of about -20° C. to about 50° C. for about 1 to about 48 hours. Exemplary solvents include acetonitrile, dichloromethane, dimethylformamide and chloroform.

The coupling agent may also be that agent which converts the carboxylic acid to an activated intermediate which is isolated and/or formed in a first step and allowed to react with the amine or alcohol in a second step. Examples of such coupling agents and activated intermediates are thionyl chloride or oxalyl chloride to form the acid chloride, cyanuric fluoride to form an acid fluoride or an alkyl chloroformate such as isobutyl or isopropenyl chloroformate (with a tertiary amine base) to form a mixed anhydride of the carboxylic acid. If the coupling agent is oxalyl chloride it is advantageous to employ a small amount of dimethylformamide as cosolvent with another solvent (such as dichloromethane) to catalyze the formation of the acid chloride. Use of these coupling agents and appropriate selection of solvents and temperatures are known to those skilled in the art or can be readily determined from the literature. These and other exemplary conditions useful for coupling carboxylic acids are described in Houben-Weyl, Vol XV, part II, E. Wunsch, Ed., G. Theime Verlag, 1974, Stuttgart, and M. Bodansky, Principles of Peptide Synthesis, Springer-Verlag Berlin 1984, and The Peptides. Analysis, Synthesis and Biology (ed. E. Gross and J. Meienhofer), vols 1–5 (Academic Press NY 1979-1983).

The Formula IV compounds wherein $R_1$, $R_{10}$, $R_{11}$, A, $R_2$, $R_3$, $R_4$, $R_5$, and $R_7$ are as defined above may be prepared from the corresponding Formula V ester (i.e., Formula I compounds wherein $R_6$ is $(C_1$–$C_5)$alkoxycarbonyl or benzyloxycarbonyl) by hydrolysis with aqueous alkali at a temperature of about -20° C. to about 100° C., typically at about 20° C., for about 30 minutes to about 24 hours.

Alternatively, Formula IV compounds are prepared by activation of a Formula II indole carboxylic acid with a coupling agent (as described above) which gives an activated intermediate (such as an acid chloride, acid fluoride, or mixed anhydride) which is then allowed to react with a compound of Formula III wherein $R_3$, $R_4$, $R_5$, and $R_7$ are as described above and $R_6$ is carboxy, in a suitable solvent in the presence of a suitable base. Suitable solvents include water or methanol or a mixture thereof, together with a cosolvent such as dichloromethane, tetrahydrofuran, or dioxane. Suitable bases include sodium, potassium or lithium hydroxides, sodium or potassium bicarbonate, sodium or potassium carbonate, or potassium carbonate together with tetrabutyl ammonium bromide (1 equivalent) in sufficient quantity to consume the acid liberated in the reaction (generally that quantity sufficient to maintain the pH of the reaction at greater than 8). The base may be added incrementally together with the activated intermediate to effect proper pH control of the reaction. The reaction is conducted generally between −20° C. and 50° C. Isolation procedures are tailored by one skilled in the art to remove impurities, but typically consist of removal of water-miscible cosolvents by evaporation, extraction of impurities at high pH with an organic solvent, acidification to low pH (1-2) and filtration or extraction of the desired product with a suitable solvent such as ethyl acetate or dichloromethane.

The Formula V compound may be prepared by coupling the appropriate Formula III compound wherein $R_6$ is alkoxycarbonyl and the appropriate Formula II compound in an analogous procedure to that described above (e.g., Procedure A).

Alternatively, Formula I compounds which contain sulfur atoms in the sulfoxide or sulfone oxidation state may be prepared from the corresponding Formula I compounds having the sulfur atom in the unoxidized form, by treatment with a suitable oxidizing agent, such as with m-chloroperoxybenzoic acid in dichloromethane at a temperature of about 0° C. to about 25° C. for about 1 to about 48 hours using about 1 to about 1.3 equivalent for conversion to the sulfoxide oxidation state and greater than about 2 equivalents for conversion to the sulfone oxidation state.

Alternatively, the Formula I compounds that are mono- or di-alkylated on $R_5$ aminoalkoxy may be prepared from the corresponding Formula I compound wherein $R_5$ is aminoalkoxy by monoalkylation or dialkylation on the $R_5$ amine to prepare the desired Formula I compound. Such a mono- or di-alkylation may be conducted by treatment of the $R_5$ aminoalkoxy compound with 1 equivalent of the appropriate carbonyl compound (for monoalkylation) or greater than 2 equivalents of the appropriate carbonyl compound (for dialkylation) and a suitable reducing agent in a suitable solvent. Suitable reducing conditions include sodium cyanoborohydride or sodium borohydride in methanol or ethanol, or hydrogen/hydrogenation catalyst (such as palladium on carbon) in a polar solvent such as water, methanol, or ethanol at about 0° C. to 60° C. for 1 to 48 hours.

Alternatively, the Formula I compounds, wherein $R_5$ is alkanoyloxy (RCOO—), are prepared by O-acylation of the appropriate Formula I compound with an appropriate acid chloride or other activated acid derivative in the presence, if necessary, of a suitable base, (e.g., tertiary amine base such as trialkylamine or pyridine), preferably in an aprotic solvent such as tetrahydrofuran or dichloromethane, at a temperature of about 0° C. to about 50° C., for about 0.5 to about 48 hours.

Alternatively, the Formula I compounds wherein $R_5$ and $R_7$ are taken together to be oxo are prepared by oxidizing a corresponding Formula I compound, for example, wherein $R_5$ is hydroxy and $R_7$ is H, with a suitable oxidizing agent. Exemplary oxidizing agents include the Dess-Martin reagent in dichloromethane, a carbodiimide and dimethylsulfoxide and acid catalyst (Pfitzner-Moffatt conditions or modifications thereof, such as employing a water-soluble carbodiimide) or Swern-type reactions (e.g., oxalyl chloride/DMSO/triethylamine). The Formula I compounds having other oxidation sensitive functionality may benefit from appropriate protection and deprotection of such functionality.

Some of the preparation methods described herein may require protection of remote functionality (i.e., primary amine, secondary amine, carboxyl in Formula I precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

For example, in Reaction Scheme I certain Formula I compounds contain primary amine, secondary amine or carboxylic acid functionality in the part of the molecule defined by R5 or $R_6$ which may interfere with the intended coupling reaction of Reaction Scheme I if the Formula III intermediate, or $R_{12}H$ or $R_8R_9NH$ amine is left unprotected. Accordingly, the primary or secondary amine functionality may be protected, where it is present in the $R_5$ or $R_6$ moieties of the Formula III intermediate or amine ($R_8R_9NH$ or $R_{12}H$) by an appropriate protecting group during the coupling reaction of Reaction Scheme I. The product of such coupling reaction is a Formula I compound containing the protecting group. This protecting group is removed in a subsequent step to provide the Formula I compound. Suitable protecting groups for amine and carboxylic acid protection include those protecting groups commonly used in peptide synthesis (such as N-t-butoxycarbonyl, N-carbobenzyloxy, and 9-fluorenylmethylenoxycarbonyl for amines and lower alkyl or benzyl esters for carboxylic acids) which are not chemically reactive under the coupling conditions described above (and immediately preceding the Examples herein as Procedure A) and can be removed without chemically altering other functionality in the Formula I compound.

The starting indole-2-carboxylic acids and indoline-2-carboxylic acids used in Reaction Scheme I, when not commercially available or known in the prior art (such art is extensively published), are available by conventional synthetic methods. For example, according to Reaction Scheme II the Formula VII indole ester may be prepared from the Formula VI compound (wherein Q is selected to achieve the desired A as defined above) via a Fischer Indole synthesis (see *The Fischer Indole Synthesis* Robinson, B. (Wiley, N.Y., 1982)) followed by saponification of the resulting Formula VII indole ester to yield the corresponding Formula VIII acid. The starting aryl hydrazone may be prepared by condensation of a readily available hydrazine with the appropriate carbonyl derivative or via the Japp-Klingeman reaction (see *Organic Reactions*, Phillips, R. R., 1959, 10, 143).

Alternatively, the Formula VIIIA indole 2-carboxylic acid may be prepared by condensation of a Formula IX ortho methyl nitro compound with an oxalate ester to yield the Formula X indole ester followed by reduction of the nitro group and subsequent hydrolysis.

This three step process is known as the Reissert indole synthesis (Reissert, Chemische Berichte 1897, 30, 1030). Conditions for accomplishing this sequence, and references thereto, are described in the literature (Kermack, et al., J. Chem . Soc. 1921, 119, 1602; Cannon et al., J. Med. Chem. 1981, 24, 238; Julian, et al in Heterocyclic Compounds, vol 3 (Wiley, New York, N.Y., 1962, R.C. Elderfield, ed.) p 18). An example of the specific implementation of this sequence is Examples 10A10C herein.

3-Halo-5-chloro-1H-indole-2-carboxylic acids may also be prepared by halogenation of 5-chloro-1H-indole-2-carboxylic acids.

Alternatively, (to Reaction Scheme II) the Formula XIV substituted indolines may be prepared by reduction of the corresponding Formula XV indoles with a reducing agent such as magnesium in methanol at a temperature of about 25° C. to about 65° C. for about 1 to about 48 hours (Reaction Scheme III).

Formula XVI indoline carboxylic acids are prepared by saponification of the corresponding Formula XVII ester (Reaction Scheme III). The Formula XVII compound is prepared by reduction of the corresponding Formula VII indole ester with a reducing agent such as magnesium in methanol as described for the conversion of the Formula XV compound to the Formula XIV compound above.

The following paragraphs describe how to prepare the various amines which are used in the above Reaction Schemes.

According to Reaction Scheme IV the Formula XXII compounds (the Formula III amines of Reaction Scheme I wherein $R_5$ is OH, $R_7$ is H and $R_6$ is an ester) or Formula XXVI compounds ($R_6$ is $C(O)NR_8R_9$ or $C(O)R_{12}$) are prepared starting from a Formula XX N-protected (denoted by $P_T$) aldehyde. The Formula XX aldehyde or the sodium bisulfite adduct of a Formula XX aldehyde is treated with potassium or sodium cyanide in aqueous solution with a cosolvent such as dioxane or ethyl acetate at a temperature of about 0° C. to about 50° C. to provide a Formula XXI cyanohydrin. The Formula XXI cyanohydrin is treated with an alcohol (e.g., ($C_1$–$C_6$)alkanol such as methanol) and a strong acid catalyst such as hydrogen chloride at a temperature of about 0° C. to about 50° C., followed by addition of water, if necessary. The protecting group ($P_T$) is then removed, if still present, by an appropriate deprotection method yielding a Formula XXII compound. For example, if the Formula XX N-protecting group $P_T$ is tert-butoxycarbonyl (t-Boc), the Formula XXIII compound is directly formed from the Formula XXI compound, and addition of water is not necessary. The Formula XXII compound may be protected on nitrogen with an appropriate protecting group to form a Formula XXIII compound followed by hydrolysis of the ester with aqueous alkali at a temperature of about 0° C. to about 50° C. in a reaction-inert solvent resulting in the corresponding Formula XXIV hydroxy acid. The Formula XXIV compound is coupled (in an analogous procedure to the coupling process described in Reaction Scheme I) with an appropriate $R_8R_9NH$ or $HR_{12}$ amine to form a Formula XXV compound, which is then deprotected resulting in the Formula XXVI compound (i.e., Formula IIII compound wherein $R_5$ is OH, $R_7$ is H and $R_6$ is $C(O)R_{12}$ or $C(O)NR_8R_9$. An example of the conversion of a Formula XXI cyanohydrin to the corresponding Formula XXII methyl ester with removal of the t-boc protecting group is provided in PCT publication WO/9325574, Example 1a. Other examples wherein a cyanohydrin is converted to Formula XXIII lower alkyl esters may be found in U.S. Pat. No. 4,814,342, and EPO publication O438233.

Certain Formula I compounds are stereoisomeric by virtue of the stereochemical configuration at the carbons labeled a and b. One skilled in the art may prepare Formula XXII and XXVI intermediates with the desired stereochemistry according to Reaction Scheme IV. For example, the Formula XX aldehyde is available in either enantiomeric form (stereochemistry at a) by literature procedures outlined below (see Reaction Scheme V). The Formula XXI cyanohydrin may be prepared from the Formula XX compound by treatment with sodium or potassium cyanide as described above while maintaining the stereochemistry at carbon a resulting in a mixture of stereoisomers at carbon b.

The skilled chemist may employ crystallization at this stage to separate isomers or purify one isomer.

For example, the preparation of the Formula XXI compound wherein $P_T$ is Boc, $R_3$ is H, $R_4$ is benzyl and the stereochemistry of carbons a and b is (S) and (R) respectively, employing this route together with purification by recrystallization is described in Biochemistry 1992, 31, 8125–8141.

Alternatively, isomer separation may be effected by chromatography or recrystallization techniques after conversion of a compound of formula XXI (mixture of isomers) to a compound of formula XXII, XXIII, XXIV, XXV, XXVI, V, IV, or I by the procedures and/or sequences described herein. Formula XXI intermediates of a specific stereochemistry at carbons a and b are converted to Formula XXII intermediates with retention of this stereochemistry by treatment with an alcohol and a strong acid catalyst, followed by addition of water, if necessary, as described above.

Alternatively, the desired isomer of the Formula XXI compound may also be obtained by derivatization of the Formula XXI intermediate and chromatographic separation of the diastereomeric derivatives (for example with trimethylsilyl chloride (TMS) or t-butyldimethylsilyl chloride (TBDMS) to give O-TMS or O-TBDMS derivatives). For example, Example 24D (contained herein) describes the separation of Formula XXI diastereomeric derivatives. A silyl derivative of a Formula XXI intermediate having a single stereoisomeric form at carbons a and b is converted with retention of stereochemistry to a Formula XXII intermediate (if the silyl group is not removed in this step it is removed subsequently by an appropriate method, such as treatment with tetrabutylammonium fluoride in tetrahydrofuran), by the method described above for the conversion of the Formula XXI compound to the Formula XXII compound (see Example 24C contained herein for conversion of a silyl derivative of Formula XXI compound to a single isomer of Formula XXII with loss of the silyl group).

According to Reaction Scheme V the Formula XX aldehydes (starting materials for Reaction Scheme IV) are prepared from the corresponding Formula XXX amino acids. The Formula XXX amino acid is protected on nitrogen with a protecting group ($P_T$) (such as Boc). The protected compound is esterified with an alcohol and converted to an ester, preferably the methyl or ethyl ester of the Formula XXXI compound. This may be accomplished by treating the Formula XXX compound with methyl or ethyl iodide in the presence of a suitable base (e.g., $K_2CO_3$) in a polar solvent such as dimethylformamide. The Formula XXXI compound is reduced, for example, with diisobutylaluminum hydride in hexane or toluene, or a mixture thereof, at a temperature of about −78° C. to about −50° C. followed by quenching with methanol at −78° C. as described in J. Med. Chem., 1985, 28, 1779–1790 to form the Formula XX aldehyde. Alternatively (not depicted in Reaction Scheme V), analogous N-methoxymethylamides corresponding to the Formula XXXI compound, wherein the alcohol substituent of the ester is replaced by N(OMe)Me, are formed from a Formula XXX compound, N,O-dimethylhydroxylamine and a suitable coupling agent (e.g., 1(3-dimethylaminopropyl)3-ethylcarbodiimide hydrochloride (DEC) as in Procedure A. The resulting compound is reduced, for example, with lithium aluminum hydride in a reaction-inert solvent such as ether or tetrahydrofuran at a temperature of about 0° C. to about 25° C. to form the Formula XX aldehyde. This two-step method is general for the conversion of N-protected a-amino acids to Formula XX aldehydes (Fehrentz and Castro, Synthesis 1983, 676–678).

Alternatively Formula XX aldehydes may be prepared by oxidation of Formula XXXIII protected aminoalcohols, for example, with pyridine-$SO_3$ at a temperature of about –10° C. to about 40° C. in a reaction-inert solvent, preferably dimethylsulfoxide. Formula XXXIII protected aminoalcohols, if not commercially available, may be prepared by protection of Formula XXXII aminoalcohols. The Formula XXXII aminoalcohols are prepared by reduction of Formula XXX amino acids. This reduction is accomplished by treatment of Formula XXX compounds with lithium aluminum hydride according to the procedure described by Dickman et al., Organic Syntheses; Wiley: New York, 1990; Collect. Vol. VII, p 530, or with sulfuric acid-sodium borohydride by the procedure of Abiko and Masamune, Tetrahedron Lett. 1992 333, 5517–5518, or with sodium borohydride-iodine according to the procedure of McKennon and Meyers, J. Org. Chem. 1993, 58, 3568–3571, who also reviewed other suitable procedures for converting Formula XXX amino acids to Formula XXXII amino alcohols.

According to Reaction Scheme VI the Formula XXX compounds utilized in Reaction Scheme V may be prepared as follows. The Formula XLI amino acids may be prepared by N-alkylation of the Formula XL protected ($P_7$) amino acids by treatment with an appropriate base and alkylating agent. Specific procedures for this alkylation are described by Benoiton, Can. J. Chem 1977, 55, 906–910, and Hansen, J. Org. Chem. 1985, 50 945–950. For example, when $R_3$ is methyl, sodium hydride and methyl iodide in tetrahydrofuran are utilized. Deprotection of the Formula XLI compound yields the desired Formula XXX compound.

Alternatively, a Formula XLII amino acid may be N-alkylated by a three-step sequence involving reductive benzylation (such as with benzaldehyde, Pd/C-catalyzed hydrogenation) to give the mono-N-benzyl derivative and reductive amination with the appropriate acyl compound (for example with formaldehyde and sodium cyanoborohydride to introduce $R_3$ as methyl) to give the N-Benzyl, N-$R_3$-substituted amino acid. The N-benzyl protecting group is conveniently removed (for example by hydrogenation with an appropriate catalyst) to yield the Formula XXX compound. Specific conditions for this three step alkylation procedure are described by Reinhold et al., J. Med. Chem., 1968, 11, 258–260.

The immediately preceding preparation may also be used to introduce an $R_3$ moiety into the Formula XLIV intermediate to form the Formula XLV intermediate (which is a Formula III intermediate wherein $R_7$ is OH). The immediately preceding preparation may also be used to introduce an $R_3$ moiety into a Formula IIIa intermediate (which is a Formula III intermediate wherein $R_3$ is H).

The amino acids used in the schemes herein (e.g., XL, XLII), if not commercially available, or reported in the literature, may be prepared by a variety of methods known to those skilled in the art. For example, the Strecker synthesis or variations thereof may be used. Accordingly, an aldehyde ($R_4$CHO), sodium or potassium cyanide and ammonium chloride react to form the corresponding aminonitrile. The aminonitrile is hydrolyzed with mineral acid to form the desired Formula XLII $R_4C(NH_2)COOH$ amino acid. Alternatively, the Bucherer-Berg method may be used wherein a hydantoin is formed by heating an aldehyde ($R_4$CHO) with ammonium carbonate and potassium cyanide followed by hydrolysis (for example, with barium hydroxide in refluxing dioxane) with acid or base to form the desired Formula XLII $R_4C(NH_2)COOH$ amino acid.

Other methods for synthesis of a-amino acids are also reported in the literature which would permit one skilled in the art to prepare the desired Formula XLII $R_4C(NH_2)COOH$ intermediate necessary for the synthesis of Formula I compounds.

Suitable methods for the synthesis or resolution of Formula XLII compounds are found in reviews by Duthaler (Tetrahedron 1994, 50, 1539–1650), or by Williams (R. M. Williams, Synthesis of optically active amino acids. Pergamon: Oxford, U.K., 1989).

A specific method for the synthesis of a Formula XLII intermediate in either enantiomeric form from the corresponding $R_4X$ (X=Cl, Br, or I) intermediate is the procedure of Pirrung and Krishnamurthy (J. Org. Chem. 1993, 58, 957–958), or by the procedure of O'Donnell, et al. (J. Am. Chem. Soc. 1989,111, 2353–2355). The required $R_4X$ intermediates are readily prepared by many methods familiar to the chemist skilled in the art. For example, those compounds when $R_4X$ is $ArCH_2X$ may be prepared by radical halogenation of the compound $ArCH_3$ or by formulation of the arene Ar-H and conversion of the alcohol to the bromide.

Another specific method for the synthesis of Formula XLII intermediates in either enantiomeric form is that of Corey and Link (J. Am. Chem. Soc. 1992, 114, 1906–1908). Thus, an intermediate of formula $R_4COCCl_3$ is reduced enantiospecifically to intermediate $R_4CH(OH)CCl_3$, which is converted on treatment with azide and base to an intermediate $R_4CH(N_3)COOH$, which is reduced by catalytic hydrogenation to the desired Formula XLII compound. The requisite trichloromethyl ketone $R_4COCCl_3$ is obtained by reaction of the aldehyde $R_4CHO$ with trichloromethide anion followed by oxidation (Gallina and Giordano, Synthesis 1989, 466–468).

Formula III intermediate amines (used in Reaction Scheme I), wherein $R_5$ and $R_7$ are H may be prepared according to Reaction Scheme VII. A Formula L amino acid (suitably protected ($P_7$) is activated by conversion to the acid chloride, fluoride or mixed anhydride (e.g., with isobutyl chloroformate and triethylamine in an inert solvent such as tetrahydrofuran or dioxane at about –0° C. to about –40° C.) and the activated intermediate treated with diazomethane to give the Formula LI diazoketone. The Formula LI diazoketone is treated with an alcohol (ROH) (e.g., ($C_1$–$C_6$)alkanol such as methanol), and a suitable catalyst such as heat, silver oxide or silver benzoate to prepare the Formula LII ester. The Formula LII ester is deprotected to form the Formula IIIA compound (via Wolff rearrangement). Alternatively the Formula LII ester is hydrolyzed, with for example alkali, and coupled with the appropriate $R_{12}H$ or $HNR_8R_9$ amine to prepare the Formula IIIB compound as described previously.

According to Reaction Scheme VIII the Formula III intermediate amines wherein $R_5$ is an oxygen linked substituent (e.g., alkoxy) (used in Reaction Scheme I) may be prepared as follows. The Formula LXI compound is alkylated on oxygen by treatment with an appropriate alkylating agent (e.g., alkyliodide, alkylbromide, alkylchloride or alkyltosylate) and sufficient base to form the alkoxide (sodium or potassium hydride) in a suitable polar aprotic solvent (e.g., dimethylformamide or tetrahydrofuran) at a temperature of about 0° C. to about 150° C. resulting in a Formula LXII compound. The Formula LXII compound is deprotected to afford the desired amine intermediate.

The Formula III intermediate amines wherein $R_5$ is ($C_1$–$C_6$) alkoxycarbonylalkoxy (used in Reaction Scheme I) may be prepared as follows. The Formula LXI compound is alkylated with a halo-alkanoate ester to form a Formula LXIII compound which is then deprotected to form the desired amine. The corresponding acid may be prepared by hydrolysis of the ester using aqueous alkali in an appropriate solvent. Those Formula III amines wherein $R_6$ contains an ester and $R_5$ contains a carboxy may be prepared from the Formula LXIII amine (as prepared above in this paragraph), wherein $R_5$ contains the carboxylic acid functionality protected as the t-butyl ester by treatment with anhydrous acid to provide the corresponding acid at $R_5$ without hydrolyzing the ester at the $R_6$ position. The Formula LXVI compounds (Formula III intermediate amines wherein $R_5$ is protected aminoalkoxy) may be prepared from the Formula LXI compound. The Formula LXI compound is alkylated with a halo-alkane-nitrile to form the Formula LXIV compound. The Formula LXIV compound is reduced to the primary amine by treatment with hydrogen and an appropriate catalyst (e.g., rhodium-on-carbon) in the presence of ammonia in preferably a polar, protic solvent such as water, methanol or ethanol to give the Formula LXV primary amine. The Formula LXV compound is protected on nitrogen with a protecting group ($P_{T1}$), which is orthogonal to the other protecting group ($P_T$), followed by deprotection of the $P_T$ protecting group to yield the desired Formula III compound. The protected Formula III compound is coupled with the appropriate Formula II compound and the resulting protected Formula I compound is deprotected.

The Formula LXIII and LXIV compounds wherein n is two are preferably prepared by treatment of the Formula LXI compound with an excess of acrylate ester or acrylonitrile, respectively, in the presence of a suitable base, such as potassium or sodium hydroxide, in a suitable solvent, preferably a polar protic solvent.

According to Reaction Scheme IX the Formula LXVII and Formula LXIX compounds (Formula III compounds wherein $R_5$ is F or $R_5$ and $R_7$ are both F) may be prepared from the Formula LXI compound. The Formula LXI compound is treated with a suitable fluorinating agent such as diethylaminosulfur trifluoride in a reaction-inert solvent such as an aprotic solvent, preferably dichloromethane, to form the Formula LXVII compound. The Formula LXVII compound is conveniently deprotected.

The Formula LXI compound is oxidized to the Formula LXVIII compound utilizing the conditions described above for the preparation of the Formula I compounds wherein $R_5$ and $R_7$ together form oxo. The Formula LXVIII compound is difluorinated under suitable conditions (e.g., diethylaminosulfur trifluoride in dichloromethane).

According to Reaction Scheme X the Formula LXXIII compound or Formula LXIV compound wherein $R_7$ is alkyl (i.e., Formula III compound wherein $R_7$ is alkyl) are prepared from the Formula LXX compound (also see Reaction Scheme V for analogous amine preparation). The Formula LXX compound is treated with an organometallic reagent $R_7M$ and the resulting secondary alcohol oxidized as in the directly preceding paragraph to form the Formula LXXI compound. The Formula LXXI compound is converted via the Formula LXXII cyanohydrin to the Formula LXXIII compound using the same conditions that are used to convert the Formula XXI compound to the Formula XXII compound in Reaction Scheme IV.

Alternatively, the Formula LXXII compound is converted to the Formula LXIV compound as described for the conversion of the cyano intermediate to the amide in Reaction Scheme V.

A compound of the formula $R_8NH_2$ or $R_9NH_2$ is monoalkylated with a carbonyl compound corresponding to $R_8$ or $R_9$, respectively, under appropriate reductive amination conditions, to give a formula $R_8R_9NH$ amine. To avoid dialkylation, it may be preferable to protect the amines ($R_8NH_2$ or $R_9NH_2$) with a suitable protecting group $P_T$ to give $R_8(P_T)NH$ or $R_9(P_T)NH$, for example by reaction with benzaldehyde and a reducing agent. The protected amines are monoalkylated with a carbonyl compound corresponding to $R_9$ or $R_8$ respectively, under suitable reductive amination conditions, to give $R_8R_9N(P_T)$. The protecting group ($P_T$) is removed (e.g. by exhaustive catalytic hydrogenation when $P_T$ is benzyl) to give a compound of formula $R_8R_9NH$. Appropriate reductive amination conditions are available from the literature to one skilled in the art. These conditions include those reported by Borch et al. (J. Am. Chem. Soc. 1971, 2897–2904) and those reviewed by Emerson (Organic Reactions, Wiley: New York, 1948 (14), 174), Hutchins et al. (Org. Prep. Proced. Int 1979 (11), 20, and Lane et al. (Synthesis 1975, 135). Reductive amination conditions favoring N-monoalkylation include those reported by Morales, et al. (Synthetic Communications 1984, 1213–1220) and Verardo et al. (Synthesis 1992 121–125). The $R_8NH_2$ or $R_9NH_2$ amines may also be monoalkylated with $R_9X$ or $R_8X$, respectively, where X is chloride, bromide, tosylate or mesylate. Alternatively, an intermediate of formula $R_8(P_T)NH$ or $R_9(P_T)NH$ may be alkylated with $R_9X$ or $R_8X$, and the protecting group removed to give a compound of formula $R_8R_9NH$.

Additional methods may be used to prepare formula $R_8R_9NH$ amines wherein $R_8$—NH or $R_9$—NH are oxygen-nitrogen linked. Thus a readily available compound of formula ($C_1$–$C_4$)alkoxycarbonyl-NHOH or $NH_2CONHOH$ is dialkylated on nitrogen and oxygen by treatment with base and excess suitable alkylating agent (R—X) to give the corresponding ($C_1$–$C_4$)alkoxycarbonyl-N(R)OR which is then hydrolyzed to give a compound of formula $R_8R_9NH$ (wherein $R_8$=$R_9$ =R). Suitable conditions, base, and alkylating agent include those described by Goel and Krolls (Org. Prep. Proced. Int. 1987, 19, 75–78) and Major and Fleck (J. Am. Chem. Soc. 1928, 50, 1479). Alternatively, a formula $NH_2CONH(OH)$ amine may be sequentially alkylated, first on oxygen to give $NH_2CONH(OR')$, then on nitrogen to give $NH_2CON(R")(OR')$, by successive treatment with the alkylating agents R'X and R"X, respectively, in the presence of a suitable base. Suitable base and alkylating agents include those described by Kreutzkamp and Messinger (Chem. Ber. 100, 3463–3465 (1967) and Danen et al (J. Am. Chem. Soc. 1973, 95, 5716–5724). Hydrolysis of these alkylated hydroxyurea derivatives yields the amines R'ONH$_2$ and R'ONHR", which correspond to certain formula R$_8$R$_9$NH amines. The chemist skilled in the art can adapt the procedures described in this paragraph to other alkylating agents R, R' and R"—X to prepare other amines of formula R$_8$R$_9$NH wherein R$_8$—N or R$_9$—N are oxygen-nitrogen linked. Uno et al (SynLett 1991, 559–560) describe the BF$_3$-catalyzed addition of an organometallic reagent R-Li to an O-alkyl oxime of formula R'CH=N—OR", to give compounds of formula R'RCH—NH(OR"). This route may also be used to give compounds of formula R$_8$R$_9$NH wherein one of R$_8$—NH or R$_9$—NH are oxygen-nitrogen linked.

Prodrugs of this invention where a carboxyl group in a carboxylic acid of Formula I is replaced by an ester may be prepared by combining the carboxylic acid with the appropriate alkyl halide in the presence of a base such as potassium carbonate in an inert solvent such as dimethylformamide at a temperature of about 0° C. to 100° C. for about 1 to about 24 hours. Alternatively the acid is combined with appropriate alcohol as solvent in the presence of a catalytic amount of acid such as concentrated sulfuric acid at a temperature of about 20° C. to 120° C., preferably at reflux, for about 1 hour to about 24 hours. Another method is the reaction of the acid with a stoichiometric amount of the alcohol in the presence of a catalytic amount of acid in an inert solvent such as tetrahydrofuran, with concomitant removal of the water being produced by physical (e.g. Dean-Stark trap) or chemical (e.g. molecular sieves) means.

Prodrugs of this invention where an alcohol function has been derivatized as an ether may be prepared by combining the alcohol with the appropriate alkyl bromide or iodide in the presence of a base such as potassium carbonate in an inert solvent such as dimethylformamide at a temperature of about 0° C. to 100° C. for about 1 to about 24 hours. Alkanoylaminomethyl ethers may be obtained by reaction of the alcohol with a bis-(alkanoylamino)methane in the presence of a catalytic amount of acid in an inert solvent such as tetrahydrofuran, according to a method described in U.S. Pat. No. 4,997, 984. Alternatively, these compounds may be prepared by the methods described by Hoffman et al. in J. Org. Chem. 1994, 59, 3530.

The dialkylphosphate esters may be prepared by reaction of the alcohol with a dialkyl chlorophosphate in the presence of a base in an inert solvent such as tetrahydrofuran. The dihydrogen phosphates may be prepared by reaction of the alcohol with a diaryl or dibenzyl chlorophosphate as described above, followed by hydrolysis or hydrogenation in the presence of a noble metal catalyst, respectively.

Glycosides are prepared by reaction of the alcohol and a carbohydrate in an inert solvent such as toluene in the presence of acid. Typically the water formed in the reaction is removed as it is being formed as described above. An alternate procedure is the reaction of the alcohol with a suitably protected glycosyl halide in the presence of base followed by deprotection.

N-(1-hydroxyalkyl) amides, N-(1-hydroxy-1-(alkoxycarbonyl)methyl) amides or compounds where R$_2$ has been replaced by C(OH)C(O)OY may be prepared by the reaction of the parent amide or indole with the appropriate aldehyde under neutral or basic conditions (e.g. sodium ethoxide in ethanol) at temperatures between 25 and 70° C. N-alkoxymethyl indoles or N-1-(alkoxy)alkyl indoles can be obtained by reaction of the N-unsubstituted indole with the necessary alkyl halide in the presence of a base in an inert solvent. 1-(N,N-dialkylaminomethyl) indole, 1-(1-(N,N-dialkylamino)ethyl) indole and N,N-dialkylaminomethyl amides (e.g. R$_3$=CH$_2$N(CH$_3$)$_2$) may be prepared by the reaction of the parent N—H compound with the appropriate aldehyde and amine in an alcoholic solvent at 25 to 70° C.

Cyclic prodrugs (e.g., the prodrugs of this invention where R$_2$ and R$_3$ are a common carbon) may be prepared by reaction of the parent compound (drug) with an aldehyde or ketone or its dimethyl acetal in an inert solvent in the presence of a catalytic amount of acid with concomitant water or methanol removal. Alternatively, these compounds may be prepared by reaction of the amino alcohol or hydroxy amide with a gem-dibromo alkane in the presence of base (e.g. potassium carbonate) in an inert solvent (e.g. dimethylformamide).

The Formula IA compounds may be prepared as described below.

The scheme numbers and formula numbers mentioned after this point of the text refer to scheme numbers and formula numbers appearing after this point in the text.

SCHEME XI
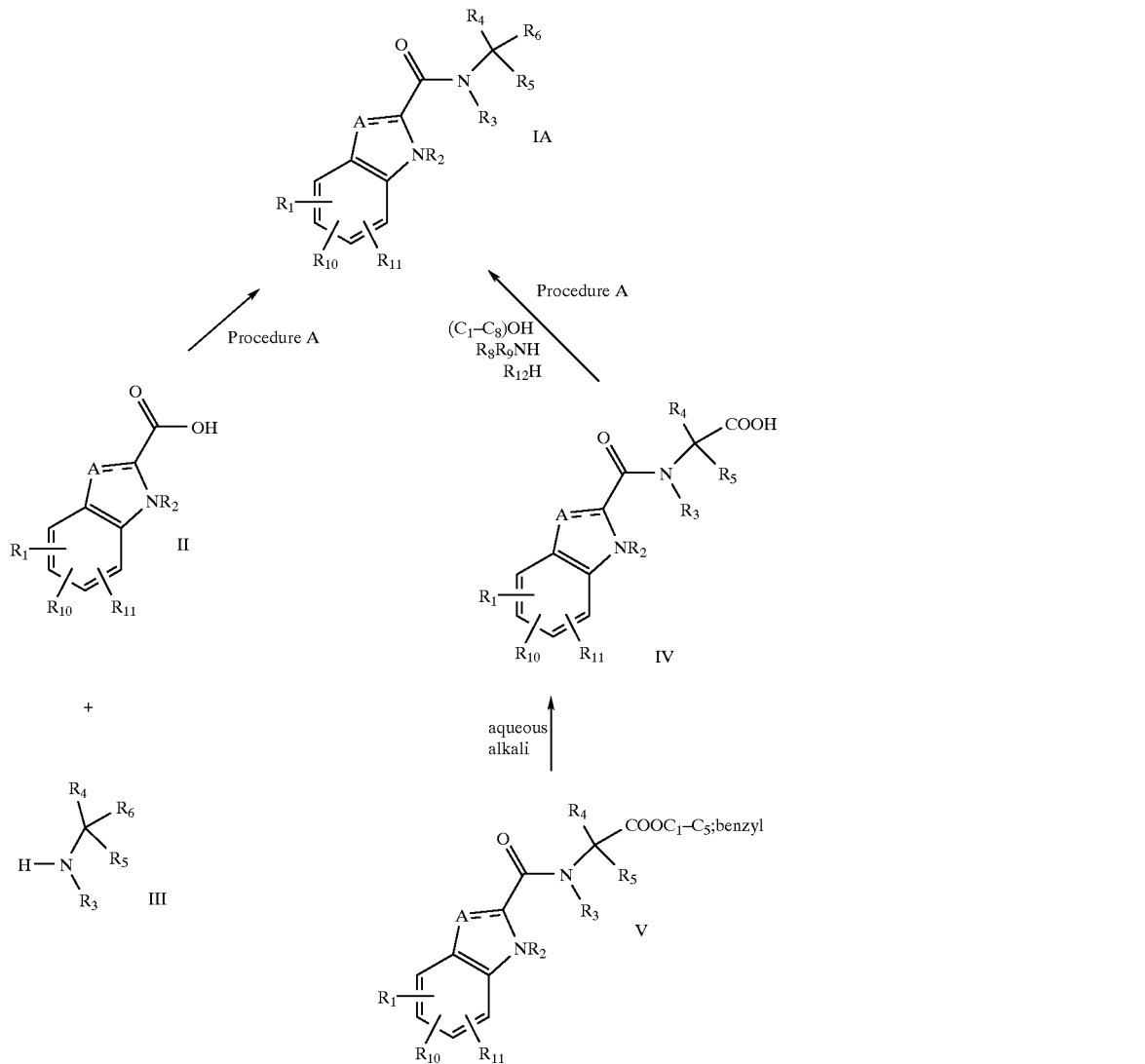
SCHEME XII
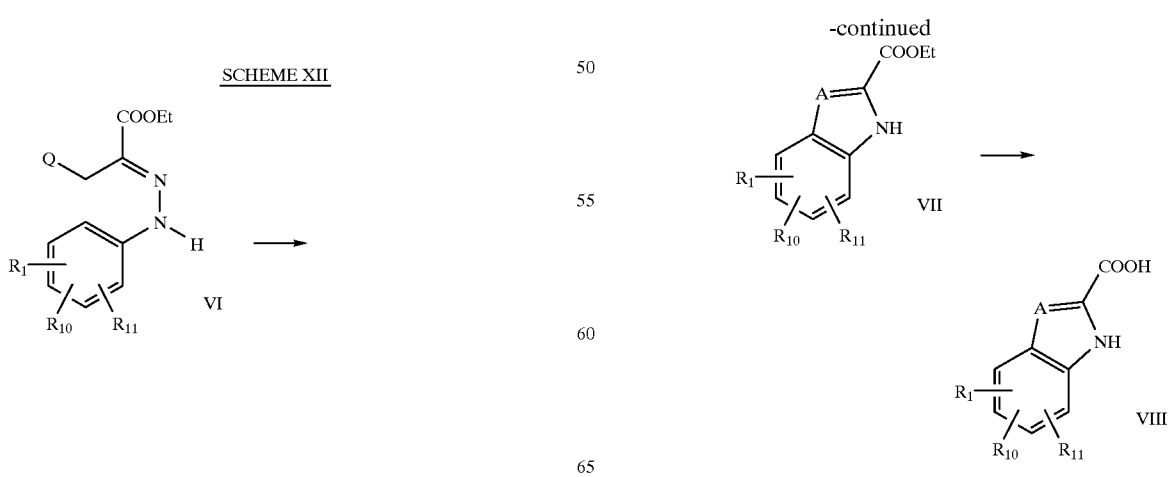

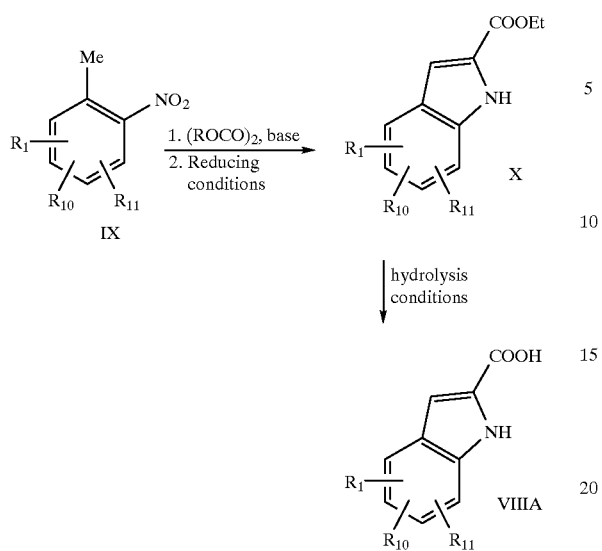
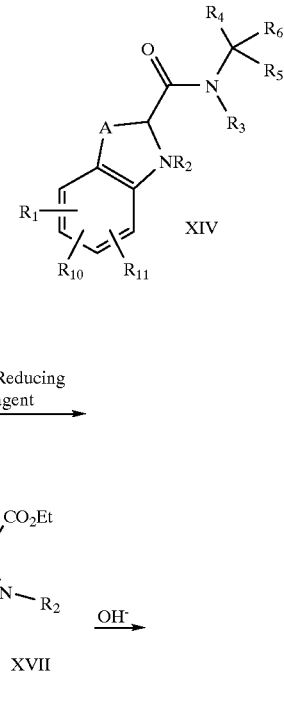
SCHEME XIII
SCHEME XIV
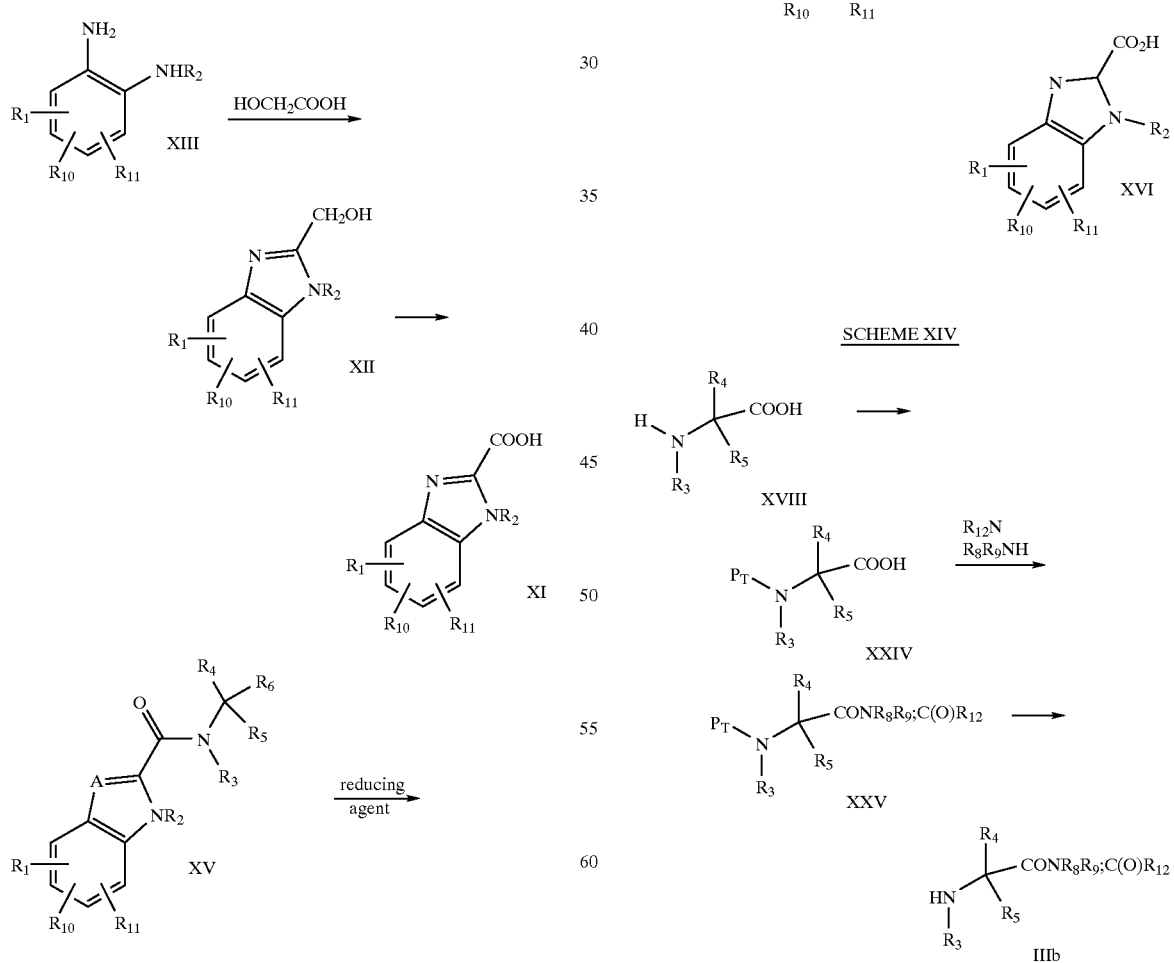

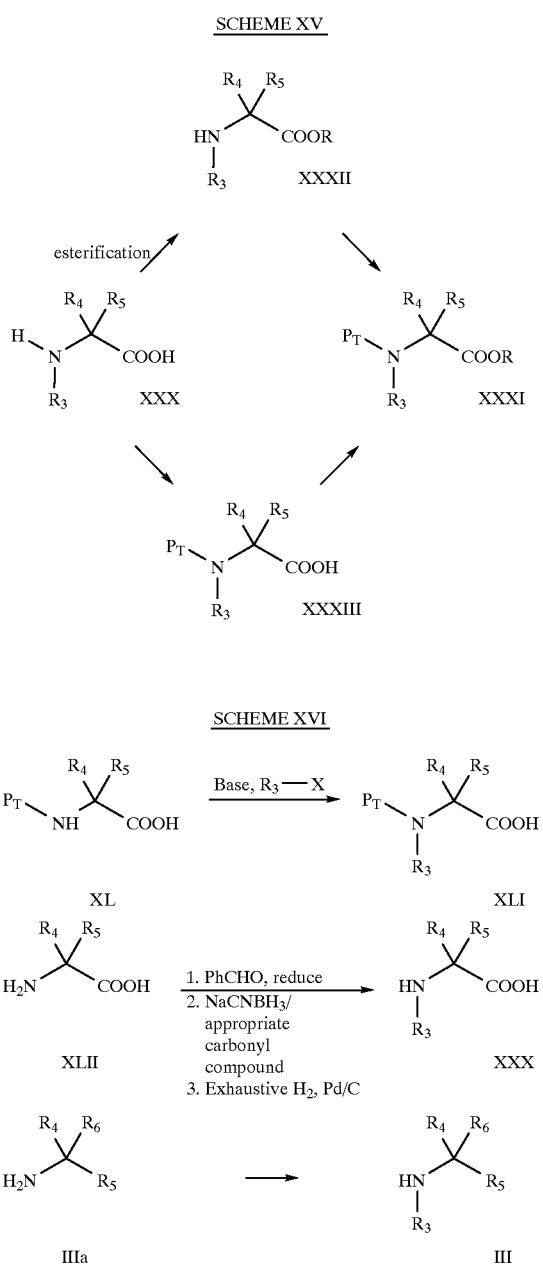

According to Reaction Scheme XI the Formula IA compounds, wherein $R_1$, $R_{10}$, $R_{11}$, A, $R_2$, $R_3$, $R_4$, $R_5$ and $R_6$ are as defined above may be prepared by either of two general processes. In the first process the desired Formula IA compound may be prepared by coupling the appropriate Formula II indole-2-carboxylic acid, indoline-2-carboxylic acid or benzimidazole-2-carboxylic acid with the appropriate Formula III amine (i.e., acylating the amine). In the second process the desired Formula IA compound may be prepared by coupling the appropriate Formula IV compound (i.e., a Formula IA compound wherein $R_6$ is carboxy) with the appropriate alcohol or formula $R_8R_9NH$ or $R_{12}H$ amine, wherein $R_8$, $R_9$ and $R_{12}$ are as defined above (i.e., acylating the amine or alcohol). The first process (coupling Formula II compounds with Formula III compounds is typically preferred when $R_4$ is not H and $R_5$ is H.

Typically, the Formula II compound is combined with the Formula III compound (or Formula IV compound is combined with the appropriate amine (e.g., $R_{12}H$ or $R_8R_9NH$)) or alcohol in the presence of a suitable coupling agent. A suitable coupling agent is one which transforms a carboxylic acid into a reactive species which forms an amide or ester linkage on reaction with an amine or alcohol, respectively.

The coupling agent may be a reagent which effects this condensation in a one pot process when mixed together with the carboxylic acid and amine or alcohol. If the acid is to be condensed with an alcohol it is preferable to employ a large excess of the alcohol as the reaction solvent, with or without 1.0 to 1.5 equivalent added dimethylaminopyridine. Exemplary coupling reagents are 1-(3-dimethylaminopropyl)3-ethylcarbodiimide hydrochloride-hydroxybenzotriazole (DEC/HBT), carbonyldiimidazole, dicyclohexylcarbodiimide/hydroxybenzotriazole (HBT), 2-ethoxy1-ethoxycarbonyl-1,2-dihydroquinoline (EEDQ), carbonyldiimidazole/HBT, propanephosphonic anhydride (propanphosphonic acid anhydride, PPA) and diethylphosphorylcyanide. The coupling is performed in an inert solvent, preferably an aprotic solvent at a temperature of about −20° C. to about 50° C. for about 1 to about 48 hours, in the optional presence of a tertiary amine base such as triethylamine. Exemplary solvents include acetonitrile, dichloromethane, ethyl acetate, dimethylformamide and chloroform or mixtures thereof.

The coupling agent may also be that agent which converts the carboxylic acid to an activated intermediate which is isolated and/or formed in a first step and allowed to react with the amine or alcohol in a second step. Examples of such coupling agents and activated intermediates are thionyl chloride or oxalyl chloride to form the acid chloride, cyanuric fluoride to form an acid fluoride or an alkyl chloroformate such as isobutyl or isopropenyl chloroformate (with a tertiary amine base) to form a mixed anhydride of the carboxylic acid. If the coupling agent is oxalyl chloride it is advantageous to employ a small amount of dimethylformamide as cosolvent with another solvent (such as dichloromethane) to catalyze the formation of the acid chloride. This acid chloride may be coupled by mixing with the Formula III intermediate in an appropriate solvent together with an appropriate base. Appropriate solvent/base combinations are for example, dichloromethane, dimethylformamide or acetonitrile or mixtures thereof in the presence of a tertiary amine base e.g., triethylamine. Other appropriate solvent/base combinations include water or a ($C_1$–$C_5$) alcohol or a mixture thereof together with a cosolvent such as dichloromethane, tetrahydrofuran or dioxane and a base such as sodium or potassium carbonate, sodium potassium of lithium hydroxide or sodium bicarbonate in sufficient quantity to consume the acid liberated in the reaction. Use of a phase transfer catalyst (typically 1 to 10 mole %) such as a quaternary ammonium halide (e.g. tetrabutylammonium bromide or methyl trioctylammonium chloride) is advantageous when a mixture of only partially miscible cosolvents is employed (e.g. dichloromethane-water or dichloromethane-methanol). Use of these coupling agents and appropriate selection of solvents and temperatures are known to those skilled in the art or can be readily determined from the literature. These and other exemplary conditions useful for coupling carboxylic acids are described in Houben-Weyl, Vol XV, part II, E. Wunsch, Ed., G. Theime Verlag, 1974, Stuttgart, and M. Bodansky, Principles of Peptide Synthesis, Springer-Verlag Berlin 1984, and The Peptides. Analysis, Synthesis and Biology (ed. E. Gross and J. Meienhofer), vols 1–5 (Academic Press NY 1979–1983).

The Formula IV compounds wherein $R_1$, $R_{10}$, $R_{11}$, A, $R_2$, $R_3$, $R_4$ and $R_5$ are as defined above may be prepared from the corresponding Formula V ester (i.e., Formula IA compounds wherein $R_6$ is $(C_1–C_5)$alkoxycarbonyl or benzyloxycarbonyl) by hydrolysis with aqueous alkali at a temperature of about −20° C. to about 100° C., typically at about 20° C., for about 30 minutes to about 24 hours.

Alternatively, Formula IV compounds are prepared by activation of a Formula II indole carboxylic acid with a coupling agent (as described above) which gives an activated intermediate (such as an acid chloride, acid fluoride, or mixed anhydride) which is then allowed to react with a compound of Formula III wherein $R_3$, $R_4$ and $R_5$, are as described above and $R_6$ is carboxy, in a suitable solvent in the presence of a suitable base. Suitable solvents include water, or methanol or a mixture thereof, together with a cosolvent such as dichloromethane, tetrahydrofuran, or dioxane. Suitable bases include sodium, potassium or lithium hydroxides, sodium or potassium bicarbonate, sodium or potassium carbonate, or potassium carbonate together with tetrabutyl ammonium bromide (1 equivalent) in sufficient quantity to consume the acid liberated in the reaction (generally that quantity sufficient to maintain the pH of the reaction at greater than 8). The base may be added incrementally together with the activated intermediate to effect proper pH control of the reaction. The reaction is conducted generally between −20° C. and 50° C. Isolation procedures are tailored by one skilled in the art to remove impurities, but typically consist of removal of water-miscible cosolvents by evaporation, extraction of impurities at high pH with an organic solvent, acidification to low pH (1–2) and filtration, or extraction of the desired product with a suitable solvent such as ethyl acetate or dichloromethane.

The Formula V compound may be prepared by coupling the appropriate Formula III compound wherein $R_6$ is alkoxycarbonyl and the appropriate Formula II compound in an analogous procedure to that described above.

Alternatively, Formula IA compounds which contain sulfur atoms in the sulfoxide or sulfone oxidation state may be prepared from the corresponding Formula IA compounds having the sulfur atom in the unoxidized form, by treatment with a suitable oxidizing agent, such as m-chloroperoxybenzoic acid in dichloromethane at a temperature of about 0° C. to about 25° C. for about 1 to about 48 hours using about 1 to about 1.3 equivalent for conversion to the sulfoxide oxidation state and greater than about 2 equivalents for conversion to the sulfone oxidation state.

Some of the preparation methods described herein may require protection of remote functionality (i.e., primary amine, secondary amine, carboxyl in Formula IA precursors). The need for such protection will vary depending on the nature of the remote functionality and the conditions of the preparation methods. The need for such protection is readily determined by one skilled in the art. The use of such protection/deprotection methods is also within the skill in the art. For a general description of protecting groups and their use, see T. W. Greene, *Protective Groups in Organic Synthesis*, John Wiley & Sons, New York, 1991.

For example, in Reaction Scheme XI certain Formula IA compounds contain primary amine, secondary amine or carboxylic acid functionality in the part of the molecule defined by $R_6$ which may interfere with the intended coupling reaction of Reaction Scheme XI, if the Formula III intermediate or $R_{12}H$ or $R_8R_9NH$ amine is left unprotected. Accordingly, the primary amine, secondary amine or carboxylic acid functionality may be protected, where it is present in the $R_6$ moieties of the Formula III intermediate $R_8R_9NH$ or $R_{12}H$ amine by an appropriate protecting group during the coupling reaction of Reaction Scheme XI. The product of such coupling reaction in such a case is a Formula IA compound containing the protecting group. This protecting group is removed in a subsequent step to provide the Formula IA compound. Suitable protecting groups for amine and carboxylic acid protection include those protecting groups commonly used in peptide synthesis (such as N-t-butoxycarbonyl, N-carbobenzyloxy, and 9-fluorenylmethylenoxycarbonyl for amines and lower alkyl or benzyl esters for carboxylic acids) which are not chemically reactive under the coupling conditions described above (and immediately preceding the Examples herein as Procedure A) and can be removed without chemically altering other functionality in the Formula IA compound.

The starting indole-2-carboxylic acids and indoline-2-carboxylic acids used in Reaction Scheme XI, when not commercially available or known in the prior art (such art is extensively published), are available by conventional synthetic methods. For example, according to Reaction Scheme XII the Formula VII indole ester (wherein A is not nitrogen) may be prepared from the Formula VI compound (wherein Q is selected to achieve the desired A as defined above, except for N) via a Fischer Indole synthesis (see *The Fischer Indole Synthesis* Robinson, B. (Wiley, New York, 1982)) followed by saponification of the resulting Formula VII indole ester to yield the corresponding Formula VIII acid. The starting aryl hydrazone may be prepared by condensation of a readily available hydrazine with the appropriate carbonyl derivative or via the Japp-Klingeman reaction (see *Organic Reactions*, Phillips, R. R., 1959, 10, 143).

Alternatively, the Formula VIIIA indole 2-carboxylic acid may be prepared by condensation of a Formula IX ortho methyl nitro compound with an oxalate ester to yield the Formula X indole ester followed by reduction of the nitro group and subsequent hydrolysis.

This three step process is known as the Reissert indole synthesis (Reissert, Chemische Berichte 1897, 30, 1030). Conditions for accomplishing this sequence, and references thereto, are described in the literature (Kermack, et al., J. Chem. Soc. 1921, 119, 1602; Cannon et al., J. Med. Chem. 1981, 24, 238; Julian, et al in Heterocyclic Compounds, vol 3 (Wiley, New York, N.Y., 1962, R. C. Elderfield, ed.) p 18). An example of the specific implementation of this sequence is Examples 10A–10C herein.

3-Halo-5-chloro-1H-indole-2-carboxylic acids may also be prepared by halogenation of 5-chloro-1H-indole-2-carboxylic acids.

According to Reaction Scheme XIII the Formula XI benzimidazole-2-carboxylic acid intermediates may be prepared by condensation of a Formula XIII ortho-diamino compound with glycolic acid, followed by oxidation of the resulting Formula XII benzimidazole-2-methanol (Bistrzycki, A. and Przeworski, G. Ber. 1912, 45, 3483). Alternatively, (to Reaction Scheme XII) the Formula XIV substituted indolines may be prepared by reduction of the corresponding Formula XV indoles with a reducing agent such as magnesium in methanol at a temperature of about 25° C. to about 65° C. for about 1 to about 48 hours (Reaction Scheme III).

Formula XVI indoline carboxylic acids are prepared by saponification of the corresponding Formula XVII ester (Reaction Scheme XIII). The Formula XVII ester is prepared by reduction of the corresponding Formula VII indole ester with a reducing agent such as magnesium in methanol as described for the conversion of the Formula XV compound to the Formula XIV compound above.

The following paragraphs describe ways to prepare the various amines which are used in the above Reaction Schemes.

According to Reaction Scheme XIV a Formula XXIII alpha-amino acid may be protected on nitrogen with an appropriate protecting group ($P_t$) (e.g., t-Boc) to form a Formula XXIV compound. One skilled in the art can readily select an appropriate protecting group and a method for its introduction. For example, two common protecting groups are t-Boc (introduced by treating the amino acid with di-t-butyldicarbonate in a preferably protic suitable solvent or solvent mixture at high pH) and CBZ (introduced by treating the amino acid with benzylchloroformate in a suitable, preferably protic solvent or solvent mixture and base). The Formula XXIV compound is coupled (in an analogous procedure to the coupling process described in Reaction Scheme XI) with an appropriate $R_8R_9NH$ or $HR_{12}$ amine to form a Formula XXV compound, which is then deprotected resulting in the Formula IIIb compound (i.e., Formula III compound wherein $R_6$ is $C(O)R_{12}$ or $C(O)NR_8R_9$). If the protecting group is t-Boc by treatment of the Formula XXV compound with an acid in a suitable, preferably aprotic, solvent. Acids for this deprotection include HCl, $MeSO_3H$ or trifluoroacetic acid.

According to Reaction Scheme XV a Formula XXXI compound (N-protected Formula III amine where $R_6$ is ($C_1$–$C_8$)alkoxycarbonyl or benzyloxycarbonyl) may be prepared from the corresponding Formula XXX unprotected amino acid via N-protection (yielding a Formula XXXIII protected amino acid) followed by esterification. For example, the Formula XXXIII compound may be esterified with the appropriate alcohol and an acid catalyst such as hydrogen chloride or thionyl chloride, or in the case of tert-butanol by treatment of the amino acid with isobutylene and an acid catalyst such as concentrated sulfuric acid or by treatment with an alkyl halide (e.g., methyl iodide) and base (e.g., potassium carbonate). Alternatively, the esterification may precede the protection step.

According to Reaction Scheme XVI the Formula XXX compounds wherein $R_3$ is not H utilized in Reaction Scheme V may be prepared as follows. The Formula XLI amino acids may be prepared by N-alkylation of the Formula XL protected ($P_T$) amino acids by treatment with an appropriate base and alkylating agent. Specific procedures for this alkylation are described by Benoiton, Can. J. Chem 1977, 55, 906–910, and Hansen, J. Org. Chem. 1985, 50 945–950. For example, when $R_3$ is methyl, and $P_T$ is Boc, sodium hydride and methyl iodide in tetrahydrofuran are utilized. Deprotection of the Formula XLI compound yields the desired Formula XXX compound.

Alternatively, a Formula XLII amino acid may be N-alkylated by a three-step sequence involving reductive benzylation (such as with benzaldehyde, Pd/C-catalyzed hydrogenation) to give the mono-N-benzyl derivative and reductive amination with the appropriate carbonyl compound (for example with formaldehyde and sodium cyanoborohydride to introduce $R_3$ as methyl) to give the N-Benzyl, N-$R_3$-substituted amino acid. The N-benzyl protecting group is conveniently removed (for example by hydrogenation with an appropriate catalyst) to yield the Formula XXX compound. Specific conditions for this three step alkylation procedure are described by Reinhold et al., J. Med. Chem., 1968,11, 258–260.

The immediately preceding preparation may also be used to introduce an $R_3$ moiety into a Formula IIIa intermediate (which is a Formula III intermediate wherein $R_3$ is H).

The amino acids used in the schemes herein (e.g., XL, XLII), if not commercially available, or reported in the literature, may be prepared by a variety of methods known to those skilled in the art. For example, the Strecker synthesis or variations thereof may be used. Accordingly, an aldehyde ($R_4CHO$), sodium or potassium cyanide and ammonium chloride react to form the corresponding aminonitrile. The aminonitrile is hydrolyzed with mineral acid to form the desired Formula XLII $R_4C(NH_2)COOH$ amino acid. Alternatively, the Bucherer-Berg method may be used wherein a hydantoin is formed by heating an aldehyde ($R_4CHO$) with ammonium carbonate and potassium cyanide followed by hydrolysis (for example, with barium hydroxide in refluxing dioxane) with acid or base to form the desired Formula XLII $R_4C(NH_2)COOH$ amino acid.

Other methods for synthesis of a-amino acids are also reported in the literature which would permit one skilled in the art to prepare the desired Formula XLII $R_4C(NH_2)COOH$ intermediate necessary for the synthesis of Formula I compounds.

Suitable methods for the synthesis and/or resolution of Formula XLII compounds are found in reviews by Duthaler (Tetrahedron 1994, 50, 1539–1650), or by Williams (R. M. Williams, Synthesis of optically active amino acids. Pergamon: Oxford, U.K., 1989).

A specific method for the synthesis of a Formula XLII intermediate in either enantiomeric form from the corresponding $R_4X$ (X=Cl, Br, or I ) intermediate is the procedure of Pirrung and Krishnamurthy (J. Org. Chem. 1993, 58, 957–958), or by the procedure of O'Donnell, et al. (J. Am. Chem. Soc. 1989, 111, 2353–2355). The required $R_4X$ intermediates are readily prepared by many methods familiar to the chemist skilled in the art. For example, those compounds when $R_4X$ is $ArCH_2X$ may be prepared by radical halogenation of the compound $ArCH_3$ or by formulation of the arene Ar—H and conversion of the alcohol to the bromide.

Another specific method for the synthesis of Formula XLII intermediates in either enantiomeric form is that of Corey and Link (J. Am. Chem. Soc. 1992, 114, 1906–1908). Thus, an intermediate of formula $R_4COCCl_3$ is reduced enantiospecifically to intermediate $R_4CH(OH)CCl_3$, which is converted on treatment with azide and base to an intermediate $R_4CH(N_3)COOH$, which is reduced by catalytic hydrogenation to the desired Formula XLII compound. The requisite trichloromethyl ketone $R_4COCCl_3$ is obtained by reaction of the aldehyde $R_4CHO$ with trichloromethide anion followed by oxidation (Gallina and Giordano, Synthesis 1989, 466–468).

A compound of the formula $R_8NH_2$ or $R_9NH_2$ is monoalkylated with a carbonyl compound corresponding to $R_8$ or $R_9$, respectively, under appropriate reductive amination conditions, to give a formula $R_8R_9NH$ amine. To avoid dialkylation, it may be preferable to protect the amines ($R_8NH_2$ or $R_9NH_2$) with a suitable protecting group $P_T$ to give $R_8(P_T)NH$ or $R_9(P_T)NH$, for example by reaction with benzaldehyde and a reducing agent. The protected amines are monoalkylated with a carbonyl compound corresponding to $R_9$ or $R_8$ respectively, under suitable reductive amination conditions, to give $R_8R_9N(P_T)$. The protecting group ($P_T$) is removed (e.g. by exhaustive catalytic hydrogenation when $P_T$ is benzyl) to give a compound of formula $R_8R_9NH$. Appropriate reductive amination conditions are available from the literature to one skilled in the art. These conditions include those reported by Borch et al. (J. Am. Chem. Soc. 1971, 2897–2904) and those reviewed by Emerson (Organic Reactions, Wiley: New York, 1948 (14), 174), Hutchins et al. (Org. Prep. Proced. Int 1979 (11), 20, and Lane et al. (Synthesis 1975, 135). Reductive amination conditions favoring N-monoalkylation include those reported by Morales, et al. (Synthetic Communications 1984, 1213–1220) and Verardo et al. (Synthesis 1992 121–125). The $R_8NH_2$ or $R_9NH_2$ amines may also be monoalkylated with $R_9X$ or $R_8X$, respectively, where X is chloride, bromide, tosylate or mesylate. Alternatively, an intermediate of formula $R_8(P_7)NH$ or $R_9(P_7)NH$ may be alkylated with $R_9X$ or $R_8X$, and the protecting group removed to give a compound of formula $R_8R_9NH$.

Additional methods may be used to prepare formula $R_8R_9NH$ amines wherein $R_8$—NH or $R_9$—NH are oxygen-nitrogen linked. Thus a readily available compound of formula $(C_1-C_4)$alkoxycarbonyl-NHOH or $NH_2CONHOH$ is dialkylated on nitrogen and oxygen by treatment with base and excess suitable alkylating agent (R—X) to give the corresponding $(C_1-C_4)$alkoxycarbonyl-N(R)OR which is then hydrolyzed to give a compound of formula $R_8R_9NH$ (wherein $R_8=R_9=R$). Suitable conditions, base, and alkylating agent include those described by Goel and Krolls (Org. Prep. Proced. Int. 1987,19,75–78) and Major and Fleck (J. Am. Chem. Soc. 1928, 50, 1479). Alternatively, N-hydroxyurea ($NH_2CONH(OH)$) may be sequentially alkylated, first on oxygen to give $NH_2CONH(OR')$, then on nitrogen to give $NH_2CON(R'')(OR')$, by successive treatment with the alkylating agents R'X and R''X, respectively, in the presence of a suitable base. Suitable base and alkylating agents include those described by Kreutzkamp and Messinger (Chem. Ber. 100, 3463–3465 (1967) and Danen et al (J. Am. Chem. Soc. 1973, 95, 5716–5724). Hydrolysis of these alkylated hydroxyurea derivatives yields the amines $R'ONH_2$ and $R'ONHR''$, which correspond to certain formula $R_8R_9NH$ amines. The chemist skilled in the art can adapt the procedures described in this paragraph to other alkylating agents R, R' and R''—X to prepare other amines of formula $R_8R_9NH$ wherein $R_8$—N or $R_9$—N are oxygen-nitrogen linked. Uno et al (SynLett 1991, 559–560) describe the $BF_3$-catalyzed addition of an organometallic reagent R—Li to an O-alkyl oxime of formula R'CH=N—OR'', to give compounds of formula R'RCH—NH(OR''). This route may also be used to give compounds of formula $R_8R_9NH$ wherein one of $R_8$—NH or $R_9$—NH are oxygen-nitrogen linked.

Prodrugs of this invention where a carboxyl group in a carboxylic acid of Formula IA is replaced by an ester may be prepared by combining the carboxylic acid with the appropriate alkyl halide in the presence of a base such as potassium carbonate in an inert solvent such as dimethylformamide at a temperature of about 0 to 100° C. for about 1 to about 24 hours. Alternatively the acid is combined with appropriate alcohol as solvent in the presence of a catalytic amount of acid such as concentrated sulfuric acid at a temperature of about 20 to 120° C., preferably at reflux, for about 1 hour to about 24 hours. Another method is the reaction of the acid with a stoichiometric amount of the alcohol in the presence of a catalytic amount of acid in an inert solvent such as tetrahydrofuran, with concomitant removal of the water being produced by physical (e.g. Dean-Stark trap) or chemical (e.g. molecular sieves) means.

Prodrugs of this invention where an alcohol function has been derivatized as an ether may be prepared by combining the alcohol with the appropriate alkyl bromide or iodide in the presence of a base such as potassium carbonate in an inert solvent such as dimethylformamide at a temperature of about 0 to 100° C. for about 1 to about 24 hours. Alkanoylaminomethyl ethers may be obtained by reaction of the alcohol with a bis-(alkanoylamino)methane in the presence of a catalytic amount of acid in an inert solvent such as tetrahydrofuran, according to a method described in U.S. Pat. No. 4,997,984. Alternatively, these compounds may be prepared by the methods described by Hoffman et al. in J. Org. Chem. 1994, 59, 3530.

The dialkylphosphate esters may be prepared by reaction of the alcohol with a dialkyl chlorophosphate in the presence of a base in an inert solvent such as tetrahydrofuran. The dihydrogen phosphates may be prepared by reaction of the alcohol with a diaryl or dibenzyl chlorophosphate as described above, followed by hydrolysis or hydrogenation in the presence of a noble metal catalyst, respectively.

Glycosides are prepared by reaction of the alcohol and a carbohydrate in an inert solvent such as toluene in the presence of acid. Typically the water formed in the reaction is removed as it is being formed as described above. An alternate procedure is the reaction of the alcohol with a suitably protected glycosyl halide in the presence of base followed by deprotection.

N-(1-hydroxyalkyl) amides, N-(1-hydroxy-1-(alkoxycarbonyl)methyl) amides or compounds where $R_2$ has been replaced by C(OH)C(O)OY may be prepared by the reaction of the parent amide or indole with the appropriate aldehyde under neutral or basic conditions (e.g. sodium ethoxide in ethanol) at temperatures between 25 and 70° C. N-alkoxymethyl indoles or N-1-(alkoxy)alkyl indoles can be obtained by reaction of the N-unsubstituted indole with the necessary alkyl halide in the presence of a base in an inert solvent. 1-(N,N-dialkylaminomethyl) indole, 1-(1-(N,N-dialkylamino)ethyl) indole and N,N-dialkylaminomethyl amides (e.g. $R_3$=$CH_2N(CH_3)_2$) may be prepared by the reaction of the parent N—H compound with the appropriate aldehyde and amine in an alcoholic solvent at 25 to 70° C.

The prodrugs of this invention where $R_2$ and $R_3$ are a common carbon may be prepared by reaction of the parent compound (drug) with benzaldehyde or a ketone or its dimethyl acetal in an inert solvent in the presence of a catalytic amount of acid with concomitant water or methanol removal.

The starting materials and reagents for the above described reaction schemes (e.g., amines, substituted indole carboxylic acids, substituted indoline carboxylic acids, amino acids), although the preparation of most of which are described above, are also readily available or can be easily synthesized by those skilled in the art using conventional methods of organic synthesis. For example, many of the intermediates used herein to prepare compounds of Formula I and IA are, are related to, or are derived from amino acids found in nature, in which there is a large scientific interest and commercial need, and accordingly many such intermediates are commercially available or are reported in the literature or are easily prepared from other commonly available substances by methods which are reported in the literature.

The compounds of Formula I and IA have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of this invention.

Although many compounds of this invention are not ionizable at physiological conditions, some of the compounds of this invention are ionizable at physiological conditions. Thus, for example some of the compounds of this invention are acidic and they form a salt with a pharmaceutically acceptable cation. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, some of the compounds of this invention are basic, and they form a salt with a pharmaceutically acceptable anion. All such salts are within the scope of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate. In addition, when the compounds of this invention form hydrates or solvates they are also within the scope of the invention.

The utility of the compounds of the present invention as medical agents in the treatment of metabolic diseases (such as are detailed herein) in mammals (e.g. humans) is demonstrated by the activity of the compounds of this invention in conventional assays and the in vitro and in vivo assays described below. Such assays also provide a means whereby the activities of the compounds of this invention can be compared with the activities of other known compounds. The results of these comparisons are useful for determining dosage levels in mammals, including humans, for the treatment of such diseases.

The three different purified glycogen phosphorylase (GP) isoenzymes, wherein glycogen phosphorylase is in the activated "a" state (referred to as glycogen phosphorylase a, or the abbreviation GPa), and referred to here as human liver glycogen phosphorylase a (HLGPa), human muscle glycogen phosphorylase a (HMGPa), and human brain glycogen phosphorylase a (HBGPa), can be obtained by the following procedures.

Expression and Fermentation

The HLGP, and HMGP cDNAs are expressed from plasmid pKK233-2 (Pharmacia Biotech. Inc., Piscataway, N.J.) in *E. coli* strain XL-1 Blue (Stratagene Cloning Systems, LaJolla, Calif.). The strain is inoculated into LB medium (consisting of 10 g tryptone, 5 g yeast extract, 5 g NaCl, and 1 ml 1N NaOH per liter) plus 100 mg/L ampicillin, 100 mg/L pyridoxine and 600 mg/L $MnCl_2$ and grown at 37° C. to a cell density of $OD_{550}$=1.0. At this point, the cells are induced with 1 mM isopropyl-1-thio-β-D-galactoside (IPTG). Three hours after induction the cells are harvested by centrifugation and cell pellets are frozen at −70° C. until needed for purification.

The HBGP cDNA can be expressed by several methodologies, for example, by the method described by Crerar, et al. (J. Biol. Chem. 270:13748–13756). The method described by Crerar, et al. (J. Biol. Chem. 270:13748–13756) for the expression of HBGP is as follows: the HBGP cDNA can be expressed from plasmid pTACTAC in *E. Coli* strain 25A6. The strain is inoculated into LB medium (consisting of 10 g tryptone, 5 g yeast extract, 5 g NaCl, and 1 ml 1N NaOH per liter) plus 50 mg/L ampicillin and grown overnight, then resuspended in fresh LB medium plus 50 mg/L ampicillin, and reinoculated into a 40X volume of LB/amp media containing 250 μM isopropyl-1-thio-β-D-galactoside (IPTG), 0.5 mM pyridoxine and 3 mM mg/L and grown at 22° C. for 48–50 hours. The cells can then be harvested by centrifugation and cell pellets are frozen at −70° C. until needed for purification.

The HLGP cDNA is expressed from plasmid pBlueBac III (Invitrogen Corp., San Diego, Calif.) which is cotransfected with BaculoGold Linear Viral DNA (Pharmingen, San Diego, Calif.) into Sf9 cells. Recombinant virus is subsequently plaque-purified. For production of protein, Sf9 cells grown in serum-free medium are infected at an moi of 0.5 and at a cell density of $2 \times 10^6$ cells/ml. After growth for 72 hours at 27° C., cells are centrifuged, and the cell pellets frozen at −70° C. until needed for purification.

Purification of Glycogen Phosphorylase Expressed in *E. coli*

The *E. coli* cells in pellets described above are resuspended in 25 mM β-glycerophosphate (pH 7.0) with 0.2 mM DTT, 1 mM $MgCl_2$, plus the following protease inhibitors:

| | |
|---|---|
| 0.7 μg/mL | Pepstatin A |
| 0.5 μg/mL | Leupeptin |
| 0.2 mM | phenylmethylsulfonyl fluoride (PMSF), and |
| 0.5 mM | EDTA, | lysed by pretreatment with 200 μg/mL lysozyme and 3 μg/mL DNAase followed by sonication in 250 mL batches for 5×1.5 minutes on ice using a Branson Model 450 ultrasonic cell disrupter (Branson Sonic Power Co., Danbury Conn.). The *E. coli* cell lysates are then cleared by centrifugation at 35,000×g for one hour followed by filtration through 0.45 micron filters. GP in the soluble fraction of the lysates (estimated to be less than 1% of the total protein) is purified by monitoring the enzyme activity (as described in GPa Activity Assay section, below) from a series of chromatographic steps detailed below.

Immobilized Metal Affinity Chromatography (IMAC)

This step is based on the method of Luong et al (Luong et al. Journal of Chromatography (1992) 584, 77–84.). 500 mL of the filtered soluble fraction of cell lysates (prepared from approximately 160–250 g of original cell pellet) are loaded onto a 130 mL column of IMAC Chelating-Sepharose (Pharmacia LKB Biotechnology, Piscataway, N.J.) which has been charged with 50 mM $CuCl_2$ and 25 mM β-glycerophosphate, 250 mM NaCl and 1 mM imidazole at pH 7 equilibration buffer. The column is washed with equilibration buffer until the $A_{280}$ returns to baseline. The sample is then eluted from the column with the same buffer containing 100 mM imidazole to remove the bound GP and other bound proteins. Fractions containing the GP activity are pooled (approximately 600 mL), and ethylenediaminetetraacetic acid (EDTA), DL-dithiothreitol (DTT), phenylmethylsulfonyl fluoride (PMSF), leupeptin and pepstatin A are added to obtain 0.3 mM, 0.2 mM, 0.2 mM, 0.5 μg/mL and 0.7 μg/mL concentrations respectively. The pooled GP is desalted over a Sephadex G-25 column (Sigma Chemical Co., St. Louis, Mo.) equilibrated with 25 mM Tris-HCl (pH 7.3), 3 mM DTT buffer (Buffer A) to remove imidazole and is stored on ice until the second chromatographic step.

5'- AMP-Sepharose Chromatography

The desalted pooled GP sample (approximately 600 mL) is next mixed with 70 mL of 5'-AMP Sepharose (Pharmacia LKB Biotechnology, Piscataway, N.J.) which has been equilibrated with Buffer A (see above). The mixture is gently agitated for one hour at 22° C. then packed into a column and washed with Buffer A until the $A_{280}$ returns to baseline. GP and other proteins are eluted from the column with 25 mM Tris-HCl, 0.2 mM DTT and 10 mM adenosine 5'-monophosphate (AMP) at pH 7.3 (Buffer B). GP-containing fractions are pooled following identification by determining enzyme (described below) activity and visualizing the $M_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM β-glycerophosphate, 0.2 mM DTT, 0.3 mM EDTA, 200 mM NaCl, pH 7.0 buffer (Buffer C) and stored on ice until use.

Prior to use of the GP enzyme, the enzyme is converted from the inactive form as expressed in *E. coli* strain XL-1 Blue (designated GPb) (Stragene Cloning Systems, La Jolla, Calif.), to the active form (designated GPa) by the procedure described in Section (A) Activation of GP below.

Purification of Glycogen Phosphorylase Expressed in Sf9 Cells

The Sf9 cells in pellets described above are resuspended in 25 mM β-glycerophosphate (pH 7.0) with 0.2 mM DTT, 1 mM MgCl2, plus the following protease inhibitors:

| | |
|---|---|
| 0.7 μg/mL | Pepstatin A |
| 0.5 μg/mL | Leupeptin |
| 0.2 mM | phenylmethylsulfonyl fluoride (PMSF), and |
| 0.5 mM | EDTA, | lysed by pretreatment with 3 μg/mL DNAase followed by sonication in batches for 3×1 minutes on ice using a Branson Model 450 ultrasonic cell disrupter (Branson Sonic Power Co., Danbury Conn.). The Sf9 cell lysates are then cleared by centrifugation at 35,000×g for one hour followed by filtration through 0.45 micron filters. GP in the soluble fraction of the lysates (estimated to be 1.5% of the total protein) is purified by monitoring the enzyme activity (as described in GPa Activity Assay section, below) from a series of chromatographic steps detailed below.

Immobilized Metal Affinity Chromatography (IMAC)

Immobilized Metal Affinity Chromatography is performed as described in the section above. The pooled, desalted GP is then stored on ice until further processed.

Activation of GP

Before further chromatography, the fraction of inactive enzyme as expressed in Sf9 cells (designated GPb) is converted to the active form (designated GPa) by the following procedure described in Section (A) Activation of GP below.

Anion Exchange Chromatography

Following activation of the IMAC purified GPb to GPa by reaction with the immobilized phosphorylase kinase, the pooled GPa fractions are dialyzed against 25 mM Tris-HCl, pH 7.5, containing 0.5 mM DTT, 0.2 mM EDTA, 1.0 mM phenylmethylsulfonyl fluoride (PMSF), 1.0 μg/mL leupeptin and 1.0 μg/mL pepstatin A. The sample is then loaded onto a MonoQ Anion Exchange Chromatography column (Pharmacia Biotech. Inc., Piscataway, N.J.). The column is washed with equilibration buffer until the $A_{280}$ returns to baseline. The sample is then eluted from the column with a linear gradient of 0–0.25 M NaCl to remove the bound GP and other bound proteins. GP-containing fractions elute between 0.1–0.2 M NaCl range, as detected by monitoring the eluant for peak protein absorbance at $A_{280}$. The GP protein is then identified by visualizing the $M_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM BES, 1.0 mM DTT, 0.5 mM EDTA, 5 mM NaCl, pH 6.8 buffer and stored on ice until use.

Determination of GP Enzyme Activity

A) Activation of GP: Conversion of GPb to GPa

Prior to the determination of GP enzyme activity, the enzyme is converted from the inactive form as expressed in *E. coli* strain XL-1 Blue (designated GPb) (Stragene Cloning Systems, La Jolla, Calif.), to the active form (designated GPa) by phosphorylation of GP using phosphorylase kinase as follows. The fraction of inactive enzyme as expressed in Sf9 cells (designated GPb) is also converted to the active form (designated GPa) by the follow procedure.

GP reaction with Immobilized Phosphorylase Kinase

Phosphorylase kinase (Sigma Chemical Company, St. Louis, Mo.) is immobilized on Affi-Gel 10 (BioRad Corp., Melvile, N.Y.) as per the manufacturer's instructions. In brief, the phosphorylase kinase enzyme (10 mg) is incubated with washed Affi-Gel beads (1 mL) in 2.5 mL of 100 mM HEPES and 80 mM $CaCl_2$ at pH 7.4 for 4 hours at 4° C. The Affi-Gel beads are then washed once with the same buffer prior to blocking with 50 mM HEPES and 1 M glycine methyl ester at pH 8.0 for one hour at room temperature. Blocking buffer is removed and replaced with 50 mM HEPES (pH 7.4), 1 mM β-mercaptoethanol and 0.2% $NaN_3$ for storage. Prior to use to convert GPb to GPa, the Affi-Gel immobilized phosphorylase kinase beads are equilibrated by washing in the buffer used to perform the kinase reaction, consisting of 25 mM β-glycerophosphate, 0.3 mM DTT, and 0.3 mM EDTA at pH 7.8 (kinase assay buffer).

The partially purified, inactive GPb obtained from 5'-AMP-Sepharose chromatography above (from *E. coli*) or the mixture of GPa and GPb obtained from IMAC above (from Sf9 cells) is diluted 1:10 with the kinase assay buffer then mixed with the aforementioned phosphorylase kinase enzyme immobilized on the Affi-Gel beads. NaATP is added to 5 mM and $MgCl_2$ to 6 mM. The resulting mixture is mixed gently at 25° C. for 30 to 60 minutes. The sample is removed from the beads and the percent activation of GPb by conversion to GPa is estimated by determining GP enzyme activity in the presence and absence of 3.3 mM AMP. The percentage of total GP enzyme activity due to GPa enzyme activity (AMP-independent) is then calculated as follows:

$$\% \text{ of total HLGPa} = \frac{\text{HLGP activity} - \text{AMP}}{\text{HLGP activity} + \text{AMP}}$$

Alternately, the conversion of GPb to GPa can be monitored by isoelectric focusing, based on the shift in electrophoretic mobility that is noted following conversion of GPb to GPa. GP samples are analyzed by isoelectric focusing (IEF) utilizing the Pharmacia PfastGel System (Pharmacia Biotech. Inc., Piscataway, N.J.) using precast gels (pI range 4–6.5) and the manufacturer's recommended method. The resolved GPa and GPb bands are then visualized on the gels by silver staining (2D-silver Stain II "Daiichi Kit", Daiichi Pure Chemicals Co., LTD., Tokyo, Japan). Identification of GPa and GPb is made by comparison to E. coli derived GPa and GPb standards that are run in parallel on the same gels as the experimental samples.

B) GPa Activity Assay

The disease/condition treating/preventing activities described herein of the compounds of this invention can be indirectly determined by assessing the effect of the compounds of this invention on the activity of the activated form of glycogen phosphorylase (GPa) by one of two methods; glycogen phosphorylase a activity is measured in the forward direction by monitoring the production of glucose-1-phosphate from glycogen or by following the reverse reaction, measuring glycogen synthesis from glucose-1-phosphate by the release of inorganic phosphate. All reactions are run in triplicate in 96-well microtiter plates and the change in absorbance due to formation of the reaction product is measured at the wavelength specified below in a MCC/340 MKII Elisa Reader (Lab Systems, Finland), connected to a Titertech Microplate Stacker (ICN Biomedical Co, Huntsville, Ala.).

To measure the GPa enzyme activity in the forward direction, the production of glucose-1-phosphate from glycogen is monitored by the multienzyme coupled general method of Pesce et al. [Pesce, M. A., Bodourian, S. H., Harris, R. C. and Nicholson, J. F. (1977) Clinical Chemistry 23, 1711–1717] modified as follows: 1 to 100 μg GPa, 10 units phosphoglucomutase and 15 units glucose-6-phosphate dehydrogenase (Boehringer Mannheim Biochemicals, Indianapolis, Ind.) are diluted to 1 mL in Buffer A (described hereinafter). Buffer A is at pH 7.2 and contains 50 mM HEPES, 100 mM KCl, 2.5 mM ethyleneglycoltetraacetic acid (EGTA), 2.5 mM $MgCl_2$, 3.5 mM $KH_2PO_4$ and 0.5 mM dithiothreitol. 20 μl of this stock is added to 80 μl of Buffer A containing 0.47 mg/mL glycogen, 9.4 mM glucose, 0.63 mM of the oxidized form of nicotinamide adenine dinucleotide phosphate (NADP+). The compounds to be tested are added as 5 μL of solution in 14% dimethylsulfoxide (DMSO) prior to the addition of the enzymes. The basal rate of GPa enzyme activity in the absence of inhibitors is determined by adding 5 μL of 14% DMSO and a fully-inhibited rate of GPa enzyme activity is obtained by adding 20 μL of 50 mM of the positive control test substance, caffeine. The reaction is followed at room temperature by measuring the conversion of oxidized NADP+ to reduced NADPH at 340 nm.

To measure the GPa enzyme activity in the reverse direction, the conversion of glucose-1-phosphate into glycogen plus inorganic phosphate is measured by the general method described by Engers et al. [Engers, H. D., Shechosky, S. and Madsen, N. B. (1970) Can. J. Biochem. 48, 746–754] modified as follows: 1 to 100 μg GPa is diluted to 1 mL in Buffer B (described hereinafter). Buffer B is at pH 7.2 and contains 50 mM HEPES, 100 mM KCl, 2.5 mM EGTA, 2.5 mM $MgCl_2$ and 0.5 mM dithiothreitol. 20 μL of this stock is added to 80 μL of Buffer B with 1.25 mg/mL glycogen, 9.4 mM glucose, and 0.63 mM glucose-1-phosphate. The compounds to be tested are added as 5 μL of solution in 14% DMSO prior to the addition of the enzyme. The basal rate of GPa enzyme activity in the absence of added inhibitors is determined by adding 5 μL of 14% DMSO and a fully-inhibited rate of GPa enzyme activity is obtained by adding 20 μL of 50 mM caffeine. This mixture is incubated at room temperature for 1 hour and the inorganic phosphate released from the glucose-1-phosphate is measured by the general method of Lanzetta et al. [Lanzetta, P. A., Alvarez, L. J., Reinach, P. S. and Candia, O. A. (1979) Anal. Biochem. 100, 95–97] modified as follows: 150 μL of 10 mg/mL ammonium molybdate, 0.38 mg/mL malachite green in 1 N HCl is added to 100 μL of the enzyme mix. After a 20 minute incubation at room temperature, the absorbance is measured at 620 nm.

The above assays carried out with a range of concentrations of test compound allows the determination of an $IC_{50}$ value (concentration of test compound required for 50% inhibition) for the in vitro inhibition of GPa enzyme activity by that test compound.

The inhibiting effect on the human liver and human muscle glycogen phosphorylase a isoforms is described in Table 1 below.

TABLE 1*

| Compound Name | HLGPa $IC_{50}$ nM | HMGPa $IC_{50}$ nM |
|---|---|---|
| 5-chloro-1H-indole-2-carboxylic acid [(1S)-((R)-hydroxy-dimethylcarbamoyl-methyl-2-phenyl-ethyl]-amide | 108 | 155 |
| 5-chloro-1H-indole-2-carboxylic acid [(1S)-((R)-hydroxy-(methoxy-methyl-carbamoyl)-methyl)-2-phenyl-ethyl]-amide | 51 | 110 |
| 5-chloro-1H-indole-2-carboxylic acid [(1S)-benzyl-3-((3-hydroxy azetidin-1-yl)-(2R)-hydroxy-3-oxopropyl]-amide | 236 | 706 |
| 5-chloro-1H-indole-2-carboxylic acid [(1S)-((R)-hydroxy-[methyl-(2-hydroxyethyl)-carbamoyl]-methyl)-2-phenyl-ethyl]-amide | 152 | 20 |
| 5-chloro-1H-indole-2-carboxylic acid [(1S)-benzyl-(2R)-hydroxy-3-((3S)-hydroxy-pyrrolidin-1-yl)-3-oxopropyl]-amide | 54 | 96 |
| 5-chloro-1H-indole-2-carboxylic acid [(1S)-benzyl-(2R)-hydroxy -3-((3S,4S)-dihydroxy-pyrrolidin-1-yl)-3-oxopropyl]-amide | 73 | 90 |
| 5-chloro-1H-indole-2-carboxylic acid [(1S)-benzyl-3-(cis-3,4-dihydroxy-pyrrolidin-1-yl)-(2R)-hydroxy-3-oxopropyl]-amide | 59 | 385 |
| 5-chloro-1H-indole-2-carboxylic acid [1-benzyl-2-(3-hydroxypyrrolidin-1-yl)-2-oxo-ethyl]-amide | 45 | 85 |
| 5-chloro-1H-indole-2-carboxylic acid [(1S)-benzyl-2-(cis-3,4-dihydroxypyrrolidin-1-yl)-2-oxo-ethyl]-amide | 30 | 97 |
| 5-chloro-1H-indole-2-carboxylic acid [(1S)-(fluoro-benzyl-2-(4-hydroxy-peperidin-1-yl)-2-oxo-ethyl]-amide | 142 | 83 |
| 5-chloro-1H-indole-2-carboxylic acid (2-oxo-2-thiazolidin-3-yl-ethyl)-amide | 307 | 433 |
| 5-chloro-1H-indole-2-carboxylic acid [(1S)-benzyl-2-(3-hydroxy-azetidin-1-yl)-2-oxo-ethyl]-amide | 65 | 121 |
| 5-chloro-1H-indole-2-carboxylic acid [(1S)-benzyl-2-(3-hydroxyimino-azetidin-1-yl)-2-oxo-ethyl]-amide | 65 | 84 |
| 5-chloro-1H-indole-2-carboxylic acid [(1S)-benzyl-2-((3S,4S)-dihydroxy-pyrrolidin-1-yl)-2-oxo-ethyl]-amide | 137 | 71 |

*data are for HLGPa and HMGPa enzyme activity ($IC_{50}$) as determined by the reverse direction assay.

Cardioprotection, as indicated by a reduction in infarcted myocardium, can be induced pharmacologically using adenosine receptor agonists in isolated, retrogradely perfused rabbit hearts as an in vitro model of myocardial ischemic preconditioning (Liu et al., Cardiovasc. Res., 28:1057–1061, 1994). The in vitro test described following demonstrates that a test compound (i.e., a compound as claimed herein) can also pharmacologically induce cardioprotection, i.e., reduced myocardial infarct size, when administered to a rabbit isolated heart. The effects of the test compound are compared to ischemic preconditioning and the A1/ A3 adenosine agonist, APNEA ($N^6$-[2-(4-aminophenyl)ethyl]adenosine), that has been shown to pharmacologically induce cardioprotection in the rabbit isolated heart (Liu et al., Cardiovasc. Res., 28:1057–1061, 1994). The exact methodology is described below.

The protocol used for these experiments closely follows that described by Liu et al., Cardiovasc. Res., 28:1057–1061, 1994. Male New Zealand White rabbits (3–4 kg) are anesthetized with sodium pentobarbital (30 mg/kg, i.v.). After deep anesthesia is achieved (determined by the absence of an ocular blink reflex) the animal is intubated and ventilated with 100% $O_2$ using a positive pressure ventilator. A left thoracotomy is performed, the heart exposed, and a snare (2-0 silk) is placed loosely around a branch of the left anterior descending coronary artery, approximately ⅔ of the distance towards the apex of the heart. The heart is removed from the chest and rapidly (<30 sec) mounted on a Langendorff apparatus. The heart is retrogradely perfused via the aorta in a non-recirculating manner with a modified Krebs solution (NaCl 118.5 mM, KCl 4.7 mM, Mg $SO_4$ 1.2 mM, $KH_2PO_4$ 1.2 mM, $NaHCO_3$ 24.8 mM, $CaCl_2$ 2.5 mM, and glucose 10 mM), at a constant pressure of 80 mmHg and a temperature of 37° C. Perfusate pH is maintained at 7.4–7.5 by bubbling with 95% $O_2$/5% $CO_2$. Heart temperature is tightly controlled by using heated reservoirs for the physiological solution and water jacketing around both the perfusion tubing and the isolated heart. Heart rate and left ventricular pressures are determined via a latex balloon which is inserted in the left ventricle and connected by stainless steel tubing to a pressure transducer. The intraventricular balloon is inflated to provide a systolic pressure of 80–100 mmHg, and a diastolic pressure $\leq$10 mmHg. Perfusate flow rates are routinely determined throughout the experimental period.

The heart is allowed to equilibrate for 30 min, over which time the heart must show stable left ventricular pressures within the parameters outlined above. If the heart rate falls below 180 bpm at any time prior to the 30 min period of regional Ischemia, the heart is paced at ≈200 bpm for the remainder of the experiment. Ischemic preconditioning is induced by total cessation of cardiac perfusion (global ischemia) for 5 min, followed by reperfusion for 10 min. A 30 min regional ischemia is then provided by tightening the snare around the coronary artery branch. Following the 30 min regional ischemia, the snare is released and the heart reperfused for an additional 120 min.

Pharmacological cardioprotection is induced by infusing the test compound at predetermined concentrations, starting 30 min prior to the 30 min regional ischemia, and continuing until the end of the 120 min reperfusion period. Hearts which receive test compounds do not undergo ischemic preconditioning. The reference compound, APNEA (500 nM) is perfused through hearts (which do not receive the test compound) for a 5 min period which ends 10 min before the 30 min regional ischemia.

At the end of the 120 min reperfusion period, the coronary artery snare is tightened, and a 0.5% suspension of fluorescent zinc cadmium sulfate particles (1–10 μM) is perfused through the heart; this stains all of the myocardium, except that area at risk for infarct development (area-at-risk). The heart is removed from the Langendorff apparatus, blotted dry, weighed, wrapped in aluminum foil and stored overnight at −20° C. The next day, the heart is sliced into 2 mm transverse sections from the apex to just above the coronary artery snare. The slices are stained with 1% triphenyl tetrazolium chloride (TTC) in phosphate-buffered saline for 20 min at 37° C. Since TTC reacts with living tissue (containing NAD-dependent dehydrogenases), this stain differentiates between living (red stained) tissue, and dead tissue (unstained infarcted tissue). The infarcted area (no stain) and the area-at-risk (no fluorescent particles) are calculated for each slice of left ventricle using a precalibrated image analyzer. To normalize the ischemic injury for difference in the area-at-risk between hearts, the data is expressed as the ratio of infarct area vs. area-at-risk (%IA/AAR).

EXAMPLE 1

Male New Zealand White rabbits (3-4 kg) (control group, n=16; preconditioned group, n=7; APNEA-treated group, n=9; 5-chloro-1H-indole-2-carboxylic acid [(1S)-benzyl-2-(3-hydroxy-azetidin-1-yl)-2-oxo-ethyl]-amide, n=6 at 5 μM) were anesthetized with sodium pentobarbital (30 mg/kg, i.v.). After deep anesthesia was achieved (determined by the absence of an ocular blink reflex) the animal was intubated and ventilated with 100% $O_2$ using a positive pressure ventilator. A left thoracotomy was performed, the heart exposed, and a snare (2-0 silk) placed loosely around a branch of the left anterior descending coronary artery, approximately ⅔ of the distance towards the apex of the heart. The heart was removed from the chest and rapidly (<30 sec) mounted on a Langendorff apparatus. The heart was retrogradely perfused via the aorta in a non-recirculating manner with a modified Krebs solution (NaCl 118.5 mM, KCl 4.7 mM, Mg $SO_4$ 1.2 mM, $KH_2PO_4$ 1.2 mM, $NaHCO_3$ 24.8 mM, $CaCl_2$ 2.5 mM, and glucose 10 mM), hereinafter referred to as Krebs solution, at a constant pressure of 80 mmHg and a temperature of 37° C. Perfusate pH was maintained at 7.4–7.5 by bubbling with 95% $O_2$/5% $CO_2$. Heart temperature was tightly controlled by using heated reservoirs for the physiological solution and water jacketing around both the perfusion tubing and the isolated heart. Heart rate and left ventricular pressures were determined via a latex balloon which was inserted in the left ventricle and connected by stainless steel tubing to a pressure transducer. The intraventricular balloon was inflated to provide a systolic pressure of 80-100 mmHg, and a diastolic pressure $\leq$10 mmHg. Perfusate flow rates were routinely determined throughout the experimental period. The hearts were allowed to equilibrate for 30 minutes before further manipulation, during which time they showed stable left ventricular pressures, as outlined above.

Hearts that were preconditioned were subjected to a five minute period of global ischemia (achieved by cross-clamping the aortic line) followed by ten minutes of reperfusion, 30 minutes of regional ischemia (provided by tightening the snare around the coronary artery branch) and a 120 minute period of reperfusion (accomplished by releasing the coronary artery snare).

In hearts that were treated with the A1/A3 agonist APNEA, the drug (500 nM, in Krebs solution) was perfused through the heart via the aorta for five minutes, followed by 10 minutes of perfusion with drug-free Krebs solution. The hearts were then subjected to 30 minutes of ischemia and 120 minutes of reperfusion, as described above.

In hearts that were treated with the test compound, 5-chloro-1H-indole-2-carboxylic acid [(1S)-benzyl-2-(3-hydroxy-azetidin-1-yl)-2-oxo-ethyl]-amide (5 μM) in Krebs solution +DMSO, 1 :1000), the drug was perfused through the heart via the aorta for a period which began 30 minutes prior to the 30 minute regional ischemia and continued throughout the ischemia and reperfusion periods described above (total perfusion time: 3 hours).

Control hearts were subjected to the 30 minutes of regional ischemia and 120 minutes of reperfusion, with no other treatments.

At the end of the 120 min reperfusion period, the coronary artery snare was again tightened, and a 0.5% suspension in Krebs solution of fluorescent zinc cadmium sulfate particles (1–10 μM) perfused through the heart. The heart was then removed from the Langendorff apparatus, blotted dry, weighed, wrapped in aluminum foil and stored overnight at −20° C. The next day, each heart was sliced into 5–7 2 mm transverse sections from the apex to just above the coronary artery snare. The slices were stained with 1% triphenyl tetrazolium chloride (TTC) in phosphate-buffered saline for 20 min at 37° C. The infarcted area (no stain) and the area-at-risk (no fluorescent particles) were calculated for each slice of left ventricle using a precalibrated image analyzer. To normalize the ischemic injury for differences in the area-at-risk between hearts, the data was expressed as the ratio of infarct area vs. area-at-risk (%IA/AAR).

The results from the above in vitro test are detailed in the following Table 1. The results demonstrate that the test compound induced significant cardioprotection relative to the control group.

TABLE 1

| Treatment | n | Infarct Area/ Area-at-Risk | Standard Erro |
|---|---|---|---|
| Control | 16 | 63.9 | 4.7 |
| Preconditioned | 7 | 18.8 | 4.1 |
| APNEA (500 nM) | 9 | 19.0 | 3.6 |
| 5-chloro-1H-indole-2-carboxylic acid [(1S)-benzyl-2-(3-hydroxy-azetidin-1-yl)-2-oxo-ethyl]-amide (5 μM) | 6 | 31.4 | 6.8 |

The glycogen phosphorylase inhibitor compounds of this invention are thus useful in reducing or minimizing damage effected directly to any tissue that may be susceptible to ischemia/reperfusion injury (e.g., brain, lung, kidney, liver, gut, skeletal muscle, pancreas, spleen, vasculature, or retina tissue) as the result of an ischemic event (e.g., arterial embolism). The active compound is therefore usefully employed prophylactically to prevent, i.e. (prospectively or prophylactically) to blunt or stem, tissue ischemia (e.g., skeletal muscle ischemia) in patients who are at risk for peripheral muscle ischemia (e.g., patients with peripheral vascular disease).

The glycogen phosphorylase inhibitor compounds of this invention are particularly well suited to the treatment of diabetic patients because of the reduction in plasma glucose levels that result from inhibition of glycogen phosphorylase, in addition to the prevention of ischemic damage that diabetics are susceptible to. The compounds of this invention are also well suited for prophylactic use with non-diabetic patients who have actually suffered or who are considered at risk of suffering from ischemic events (e.g., patients undergoing surgical procedures or patients with peripheral vascular diseases).

Administration of the compounds of this invention can be via any method which delivers the glycogen phosphorylase inhibitor to the desired tissue. These methods include topical, oral routes, parenteral, intraduodenal routes, etc.

Thus, for example, in one mode of administration the glycogen phosphorylase inhibitor of this invention may be administered just prior to major surgery requiring general anesthesia (e.g., within twenty-four hours of surgery) where there is risk of ischemia e.g., gastric ischemia. In an alternative exemplary mode, the compounds may be administered subsequent to transplant surgery (e.g., within twenty-four hours after surgery) where there is risk of ischemia in a transplanted tissue. The compounds of this invention may also be administered in a chronic daily mode. In any event the amount and timing of compound(s) administered will, of course, be dependent on the subject being treated, on the severity of the affliction, on the manner of administration and on the judgment of the prescribing physician. Thus, because of patient to patient variability, the dosages given below are a guideline and the physician may titrate doses of the drug to achieve the effect that the attending physician considers appropriate for the patient. In considering the degree of glycogen phosphorylase inhibitor activity desired, the physician must balance a variety of factors such as the target tissue and severity of the disease/condition age of the patient.

An amount of the glycogen phosphorylase inhibitor of this invention that is effective for the activities of this invention is used. Typically, an effective dosage for the glycogen phosphorylase inhibitor of this invention is in the range of about 0.005 to 50 mg/kg/day, preferably 0.01 to 25 mg/kg/day and most preferably 0.1 to 15 mg/kg/day.

Generally, the compounds of this invention are administered orally, but parenteral administration (e.g., intravenous, intramuscular, subcutaneous or intramedullary) may be utilized, for example, where oral administration is inappropriate for the instant target or where the patient is unable to ingest the drug (e.g., due to age or surgical state). For certain tissues such as the eye, topical administration may also be suitable.

Glycogen phosphorylase inhibitors may be administered by a route that allows them to reach brain tissue in sufficient concentration e.g., orally, intracranially or topically. Any compound that does not readily cross the blood/brain barrier, may be determined by standard assays such as high pressure liquid chromatography analysis of brain tissue extracts.

The compounds of the present invention are generally administered in the form of a pharmaceutical composition comprising at least one glycogen phosphorylase inhibitor together with a pharmaceutically acceptable vehicle or diluent. Thus, the compounds can be administered individually or together in any conventional oral, parenteral or transdermal dosage form.

For oral administration a pharmaceutical composition can take the form of solutions, suspensions, tablets, pills, capsules, powders, and the like. Tablets containing various excipients such as sodium citrate, calcium carbonate and calcium phosphate are employed along with various disintegrants such as starch and preferably potato or tapioca starch and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type are also employed as fillers in soft and hard-filled gelatin capsules; preferred materials in this connection also include lactose or milk sugar as well as high molecular weight polyethylene glycols. When aqueous suspensions and/or elixirs are desired for oral administration, the compound of this invention can be combined with various sweetening agents, flavoring agents, coloring agents, emulsifying agents and/or suspending agents, as well as such diluents as water, ethanol, propylene glycol, glycerin and various like combinations thereof.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes. In this connection, the sterile aqueous media employed are all readily obtainable by standard techniques well-known to those skilled in the art.

Transdermal or intracranial (e.g., topical) compositions may be prepared by those skilled in the art.

Methods of preparing various pharmaceutical compositions with a certain amount of active ingredient are known, or will be apparent in light of this disclosure, to those skilled in this art. For examples of how to prepare such compositions see *Remington's Pharmaceutical Sciences*, Mack Publishing Company, Easter, Pa., 15th Edition (1975).

Pharmaceutical compositions according to the invention may contain 0.01%–95% of the compound(s) of this invention, preferably 1%–70%. In any event, the composition or formulation to be administered will contain a quantity of a compound(s) according to the invention in an amount effective to treat the signs of the subject being treated, i.e., protection from non-cardiac ischemic damage.

It should be understood that the invention is not limited to the particular embodiments described herein, but that various changes and modifications may be made without departing from the spirit and scope of this novel concept as defined by the following claims.

We claim:

1. A method of reducing non-cardiac tissue damage resulting from ischemia or hypoxia comprising administering to a mammal in need of such treatment an amount of a glycogen phosphorylase inhibitor effective at reducing non-cardiac ischemic damage.

2. A method as recited in claim 1 wherein the tissue is brain, liver, kidney, lung, gut, skeletal muscle, spleen, pancreas, nerve, spinal cord, retina tissue, the vasculature, or intestinal tissue.

3. A method as recited in claim 2 wherein said glycogen phosphorylase inhibitor is a compound of the Formula I

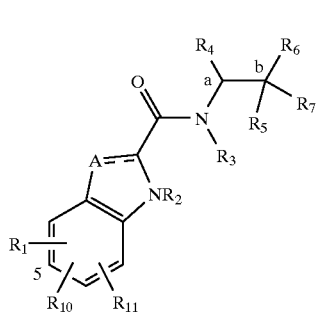

Formula I and the pharmaceutically acceptable salts and prodrugs thereof wherein the dotted line (—) is an optional bond;

A is —C(H)=, —C(($C_1$–$C_4$)alkyl)= or —C(halo)= when the dotted line (—) is a bond, or A is methylene or —CH(($C_1$–$C_4$)alkyl)- when the dotted line (—) is not a bond;

$R_1$, $R_{10}$ or $R_{11}$ are each independently H, halo, 4-, 6- or 7-nitro, cyano, ($C_1$–$C_4$)alkyl, ($C_1$–$C_4$)alkoxy, fluoromethyl, difluoromethyl or trifluoromethyl;

$R_2$ is H;

$R_3$ is H or ($C_1$–$C_5$)alkyl;

$R_4$ is H, methyl, ethyl, n-propyl, hydroxy($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, phenyl($C_1$–$C_4$)alkoxy ($C_1$–$C_4$)alkyl, thien-2- or -3-yl($C_1$–$C_4$)alkyl or fur-2- or -3-yl($C_1$–$C_4$)alkyl wherein said $R_4$ rings are mono-, di- or tri-substituted independently on carbon with H, halo, ($C_1$–$C_4$)alkyl, ($C_1$–$C_4$)alkoxy, trifluoromethyl, hydroxy, amino or cyano; or $R_4$ is pyrid-2-, -3- or -4-yl($C_1$–$C_4$)alkyl, thiazol-2-, -4- or -5-yl($C_1$–$C_4$)alkyl, imidazol -1-, -2-, -4- or -5-yl ($C_1$–$C_4$)alkyl, pyrrol-2- or -3-yl($C_1$–$C_4$)alkyl, oxazol-2-, -4- or -5-yl-($C_1$–$C_4$)alkyl, pyrazol-3-, -4- or -5-yl ($C_1$–$C_4$)alkyl, isoxazol-3-, -4- or -5-yl ($C_1$–$C_4$)alkyl, isothiazol-3-, -4- or -5-yl($C_1$–$C_4$)alkyl, pyridazin-3- or -4-yl-($C_1$–$C_4$)alkyl, pyrimidin-2-, -4-, -5- or -6-yl ($C_1$–$C_4$)alkyl, pyrazin-2- or -3-yl($C_1$–$C_4$)alkyl or 1,3, 5-triazin-2-yl($C_1$–$C_4$)alkyl, wherein said preceding $R_4$ heterocycles are optionally mono- or di-substituted independently with halo, trifluoromethyl, ($C_1$–$C_4$) alkyl, ($C_1$–$C_4$)alkoxy, amino or hydroxy and said mono- or di-substituents are bonded to carbon;

$R_5$ is H, hydroxy, fluoro, ($C_1$–$C_5$)alkyl, ($C_1$–$C_5$)alkoxy, ($C_1$–$C_6$)alkanoyl, amino($C_1$–$C_4$)alkoxy, mono-N- or di-N,N-($C_1$–$C_4$)alkylamino($C_1$–$C_4$)alkoxy, carboxy ($C_1$–$C_4$)alkoxy, ($C_1$–$C_5$)alkoxy-carbonyl($C_1$–$C_4$) alkoxy, benzyloxycarbonyl($C_1$–$C_4$)alkoxy, or carbonyloxy wherein said carbonyloxy is carbon-carbon linked with phenyl, thiazolyl, imidazolyl, 1H-indolyl, furyl, pyrrolyl, oxazolyl, pyrazolyl, isoxazolyl, isothiazolyl, pyridazinyl, pyrimidinyl, pyrazinyl or 1,3,5-triazinyl and wherein said preceding $R_5$ rings are optionally mono-substituted with halo, ($C_1$–$C_4$)alkyl, ($C_1$–$C_4$) alkoxy, hydroxy, amino or trifluoromethyl and said mono-substituents are bonded to carbon;

$R_7$ is H, fluoro or ($C_1$–$C_5$)alkyl; or $R_5$ and $R_7$ can be taken together to be oxo;

$R_6$ is carboxy, ($C_1$–$C_8$)alkoxycarbonyl, C(O)$NR_8R_9$ or C(O)$R_{12}$, wherein $R_8$ is H, ($C_1$–$C_3$)alkyl, hydroxy or ($C_1$–$C_3$)alkoxy; and $R_9$ is H, ($C_1$–$C_8$)alkyl, hydroxy, ($C_1$–$C_8$)alkoxy, methylene-perfluorinated($C_1$–$C_8$)alkyl, phenyl, pyridyl, thienyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, pyridazinyl, pyrimidinyl, pyrazinyl, piperazinyl or 1,3,5-triazinyl wherein said preceding $R_9$ rings are carbon-nitrogen linked; or $R_9$ is mono-, di- or tri-substituted ($C_1$–$C_5$)alkyl, wherein said substituents are independently H, hydroxy, amino, mono-N- or di-N,N-($C_1$–$C_5$)alkylamino; or $R_9$ is mono- or di-substituted ($C_1$–$C_5$)alkyl, wherein said substituents are independently phenyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl or 1,3,5-triazinyl wherein the nonaromatic nitrogen-containing $R_9$ rings are optionally mono-substituted on nitrogen with ($C_1$–$C_6$) alkyl, benzyl, benzoyl or ($C_1$–$C_6$)alkoxycarbonyl and wherein the $R_9$ rings are optionally mono-substituted on carbon with halo, ($C_1$–$C_4$)alkyl, ($C_1$–$C_4$)alkoxy, hydroxy, amino, or mono-N- and di-N,N ($C_1$–$C_5$) alkylamino provided that no quaternized nitrogen is included and there are no nitrogen-oxygen, nitrogen-nitrogen or nitrogen-halo bonds;

$R_{12}$ is piperazin-1-yl, 4-($C_1$–$C_4$)alkylpiperazin-1-yl, 4-formylpiperazin-1-yl, morpholino, thiomorpholino, 1-oxothiomorpholino, 1,1-dioxo-thiomorpholino, thiazolidin-3-yl, 1-oxo-thiazolidin-3-yl, 1,1-dioxothiazolidin-3-yl, 2-($C_1$–$C_6$)alkoxycarbonylpyrrolidin-1-yl, oxazolidin-3-yl or 2(R)-hydroxymethylpyrrolidin-1-yl; or $R_{12}$ is 3- and/or 4-mono- or di-substituted oxazetidin-2-yl, 2-, 4-, and/or 5-mono- or di-substituted oxazolidin-3-yl, 2-, 4-, and/or 5-mono- or di-substituted thiazolidin-3-yl, 2-, 4-, and/or 5-mono- or di-substituted 1-oxothiazolidin-3-yl, 2-, 4-, and/or 5- mono- or di-substituted 1,1-dioxothiazolidin-3-yl, 3- and/or 4-, mono- or di-substituted pyrrolidin-1-yl, 3-, 4- and/or 5-, mono-, di- or tri-substituted piperidin-1-yl, 3-, 4-, and/or 5-mono-, di-, or tri-substituted piperazin-1-yl, 3-substituted azetidin-1-yl, 4- and/or 5-, mono- or di-substituted 1,2-oxazinan-2-yl, 3-and/or 4-mono- or di-substituted pyrazolidin-1-yl, 4- and/or 5-, mono- or di-substituted isoxazolidin-2-yl, 4-and/or 5-, mono- and/or di-substituted isothiazolidin-2-yl wherein said $R_{12}$ substituents are independently H, halo, ($C_1$–$C_5$)-alkyl, hydroxy, amino, mono-N- or di-N,N-($C_1$–$C_5$) alkylamino, formyl, oxo, hydroxyimino, ($C_1$–$C_5$) alkoxy, carboxy, carbamoyl, mono-N- or di-N,N-($C_1$–$C_4$)alkylcarbamoyl, ($C_1$–$C_4$)alkoxyimino, ($C_1$–$C_4$)alkoxymethoxy, ($C_1$–$C_6$)alkoxycarbonyl, carboxy($C_1$–$C_5$)alkyl or hydroxy($C_1$–$C_5$)alkyl;

with the proviso that if $R_4$ is H, methyl, ethyl or n-propyl $R_5$ is OH;

with the proviso that if $R_5$ and $R_7$ are H, then $R_4$ is not H, methyl, ethyl, n-propyl, hydroxy($C_1$–$C_3$)alkyl or ($C_1$–$C_3$)alkoxy($C_1$–$C_3$)alkyl and $R_6$ is C(O)NR$_8$R$_9$, C(O)R$_{12}$ or ($C_1$–$C_4$)alkoxycarbonyl; or a compound of the Formula IA

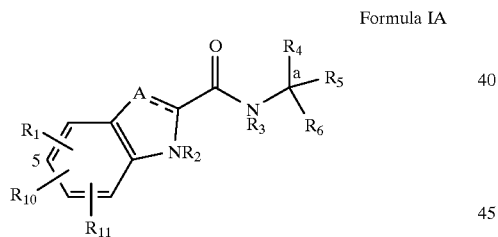

Formula IA and the pharmaceutically acceptable salts and prodrugs thereof wherein the dotted line (—) is an optional bond;

A is —C(H)=, —C(($C_1$–$C_4$)alkyl)=, —C(halo)= or —N=, when the dotted line (—) is a bond, or A is methylene or —CH(($C_1$–$C_4$)alkyl)-, when the dotted line (—) is not a bond;

$R_1$, $R_{10}$ or $R_{11}$ are each independently H, halo, cyano, 4-, 6-, or 7-nitro, ($C_1$–$C_4$)alkyl, ($C_1$–$C_4$)alkoxy, fluoromethyl, difluoromethyl or trifluoromethyl;

$R_2$ is H;

$R_3$ is H or ($C_1$–$C_5$)alkyl;

$R_4$ is H, methyl, ethyl, n-propyl, hydroxy($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, (phenyl)(($C_1$–$C_4$)-alkoxy)($C_1$–$C_4$)alkyl, thien-2- or -3-yl($C_1$–$C_4$)alkyl or fur-2- or -3-yl($C_1$–$C_4$)alkyl wherein said $R_4$ rings are mono-, di- or tri-substituted independently on carbon with H, halo, ($C_1$–$C_4$)alkyl, ($C_1$–$C_4$)alkoxy, trifluoromethyl, hydroxy, amino, cyano or 4,5-dihydro-1H-imidazol-2-yl; or $R_4$ is pyrid-2-, -3- or -4-yl($C_1$–$C_4$)alkyl, thiazol-2-, -4- or -5-yl($C_1$–$C_4$)alkyl, imidazol-2-, -4- or -5-yl($C_1$–$C_4$) alkyl, pyrrol-2- or -3-yl($C_1$–$C_4$)alkyl, oxazol-2-, -4- or -5-yl($C_1$–$C_4$)alkyl, pyrazol-3-, -4- or -5-yl($C_1$–$C_4$) alkyl, isoxazol-3-, -4- or -5-yl($C_1$–$C_4$)alkyl, isothiazol-3-, -4- or -5-yl($C_1$–$C_4$)alkyl, pyridazin-3- or -4-yl ($C_1$–$C_4$)alkyl, pyrimidin-2-, -4-, -5- or -6-yl($C_1$–$C_4$) alkyl, pyrazin-2- or -3-yl($C_1$–$C_4$)alkyl, 1,3,5-triazin-2-yl($C_1$–$C_4$)alkyl or indol-2-($C_1$–$C_4$)alkyl, wherein said preceding $R_4$ heterocycles are optionally mono- or di-substituted independently with halo, trifluoromethyl, ($C_1$–$C_4$)alkyl, ($C_1$–$C_4$)alkoxy, amino, hydroxy or cyano and said substituents are bonded to carbon; or $R_4$ is $R_{15}$-carbonyloxymethyl, wherein said $R_{15}$ is phenyl, thiazolyl, imidazolyl, 1H-indolyl, furyl, pyrrolyl, oxazolyl, pyrazolyl, isoxazolyl, isothiazolyl, pyridyl, pyridazinyl, pyrimidinyl, pyrazinyl or 1,3,5-triazinyl and wherein said preceding $R_{15}$ rings are optionally mono- or di-substituted independently with halo, amino, hydroxy, ($C_1$–$C_4$)alkyl, ($C_1$–$C_4$)alkoxy or trifluoromethyl and said mono- or di-substituents are bonded to carbon;

$R_5$ is H;

$R_6$ is carboxy, ($C_1$–$C_8$)alkoxycarbonyl, benzyloxycarbonyl, C(O)NR$_8$R$_9$ or C(O)R$_{12}$ wherein $R_8$ is H, ($C_1$–$C_6$)alkyl, cyclo($C_3$–$C_6$)alkyl, cyclo($C_3$–$C_6$)alkyl($C_1$–$C_5$)alkyl, hydroxy or ($C_1$–$C_8$)alkoxy; and $R_9$ is H, cyclo($C_3$–$C_8$)alkyl, cyclo($C_3$–$C_8$)alkyl($C_1$–$C_5$) alkyl, cyclo($C_4$–$C_7$)alkenyl, cyclo($C_3$–$C_7$)alkyl ($C_1$–$C_5$)alkoxy, cyclo($C_3$–$C_7$)alkyloxy, hydroxy, methyleneperfluorinated($C_1$–$C_8$)alkyl, phenyl, or a heterocycle wherein said heterocycle is pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, pyridinyl, piperidinyl, morpholinyl, pyridazinyl, pyrimidinyl, pyrazinyl, piperazinyl, 1,3,5-triazinyl, benzothiazolyl, benzoxazolyl, benzimidazolyl, thiochromanyl or tetrahydrobenzothiazolyl wherein said heterocycle rings are carbon-nitrogen linked; or $R_9$ is ($C_1$–$C_6$)alkyl or ($C_1$–$C_8$)alkoxy wherein said ($C_1$–$C_6$)alkyl or ($C_1$–$C_8$)alkoxy is optionally monosubstituted with cyclo($C_4$–$C_7$)alken-1-yl, phenyl, thienyl, pyridyl, furyl, pyrrolyl, pyrrolidinyl, oxazolyl, thiazolyl, imidazolyl, pyrazolyl, pyrazolinyl, pyrazolidinyl, isoxazolyl, isothiazolyl, pyranyl, piperidinyl, morpholinyl, thiomorpholinyl, 1-oxothiomorpholinyl, 1,1-dioxothiomorpholinyl, pyridazinyl, pyrimidinyl, pyrazinyl, piperazinyl, 1,3,5-triazinyl or indolyl and wherein said ($C_1$–$C_6$)alkyl or ($C_1$–$C_8$)alkoxy are optionally additionally independently mono- or di-substituted with halo, hydroxy, ($C_1$–$C_5$)alkoxy, amino, mono-N- or di-N,N-($C_1$–$C_5$) alkylamino, cyano, carboxy, or ($C_1$–$C_4$) alkoxycarbonyl; and wherein the $R_9$ rings are optionally mono- or di-substituted independently on carbon with halo, ($C_1$–$C_4$)alkyl, ($C_1$–$C_4$)alkoxy, hydroxy, hydroxy ($C_1$–$C_4$)alkyl, amino($C_1$–$C_4$)alkyl, mono-N- or di-N,N-($C_1$–$C_4$)alkylamino($C_1$–$C_4$)alkyl, ($C_1$–$C_4$)alkoxy ($C_1$–$C_4$)alkyl, amino, mono-N- or di-N,N-($C_1$–$C_4$) alkylamino, cyano, carboxy, ($C_1$–$C_5$)alkoxycarbonyl, carbamoyl, formyl or trifluoromethyl and said $R_9$ rings may optionally be additionally mono- or di-substituted independently with $(C_1-C_5)$alkyl or halo;

with the proviso that no quaternized nitrogen on any $R_9$ heterocycle is included;

$R_{12}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan2-yl, pyrazolidin-1-yl, isoxazolidin-2-yl, isothiazolidin-2-yl, 1,2-oxazetidin-2-yl, oxazolidin-3-yl, 3,4-dihydroisoquinolin-2-yl, 1,3-dihydroisoindol-2-yl, 3,4-dihydro-2H-quinol-1-2,3-dihydro-benzo[1,4]oxazin-4-yl, 2,3-dihydro-benzo[1,4]-thiazine-4-yl, 3,4-dihydro-2H-quinoxalin-1-yl, 3,4-dihydro-benzo[c][1,2]oxazin-1-yl, 1,4-dihydro-benzo[d][1,2]oxazin-3-yl, 3,4-dihydro-benzo[e][1,2]-oxazin-2-yl, 3H-benzo[d]isoxazol-2-yl, 3H-benzo[c]isoxazol-1-yl or azepan-1-yl, wherein said $R_{12}$ rings are optionally mono-, di- or tri-substituted independently with halo, $(C_1-C_5)$alkyl, $(C_1-C_5)$alkoxy, hydroxy, amino, mono-N- or di-N,N-$(C_1-C_5)$alkylamino, formyl, carboxy, carbamoyl, mono-N- or di-N,N-$(C_1-C_5)$alkylcarbamoyl, $(C_1-C_6)$alkoxy$(C_1-C_3)$alkoxy, $(C_1-C_5)$alkoxycarbonyl, benzyloxycarbonyl, $(C_1-C_5)$alkoxycarbonyl$(C_1-C_5)$alkyl, $(C_1-C_4)$alkoxycarbonylamino, carboxy$(C_1-C_5)$alkyl, carbamoyl$(C_1-C_5)$alkyl, mono-N- or di-N,N-$(C_1-C_5)$alkylcarbamoyl$(C_1-C_5)$alkyl, hydroxy$(C_1-C_5)$alkyl, $(C_1-C_4)$alkoxy$(C_1-C_4)$alkyl, amino$(C_1-C_4)$alkyl, mono-N- or di-N,N-$(C_1-C_4)$alkylamino$(C_1-C_4)$alkyl, oxo, hydroxyimino or $(C_1-C_6)$alkoxyimino and wherein no more than two substituents are selected from oxo, hydroxyimino or $(C_1-C_6)$alkoxyimino and oxo, hydroxyimino or $(C_1-C_6)$alkoxyimino are on non-aromatic carbon; and wherein said $R_{12}$ rings are optionally additionally mono- or di-substituted independently with $(C_1-C_5)$alkyl or halo;

with the proviso that when $R_6$ is $(C_1-C_5)$alkoxycarbonyl or benzyloxycarbonyl then $R_1$ is 5-halo, 5-$(C_1-C_4)$alkyl or 5-cyano and $R_4$ is (phenyl)(hydroxy)$(C_1-C_4)$alkyl, (phenyl)($(C_1-C_4)$alkoxy)$(C_1-C_4)$alkyl, hydroxymethyl or Ar$(C_1-C_2)$alkyl, wherein Ar is thien-2- or -3-yl, fur-2- or -3-yl or phenyl wherein said Ar is optionally mono- or di-substituted independently with halo; with the provisos that when $R_4$ is benzyl and $R_5$ is methyl, $R_{12}$ is not 4-hydroxy-piperidin-1-yl or when $R_4$ is benzyl and $R_5$ is methyl $R_6$ is not C(O)N(CH$_3$)$_2$;

with the proviso that when $R_1$ and $R_{10}$ and $R_{11}$ are H, $R_4$ is not imidazol-4-ylmethyl, 2-phenylethyl or 2-hydroxy-2-phenylethyl;

with the proviso that when $R_8$ is H and $R_9$ is $(C_1-C_6)$alkyl, $R_9$ is not substituted with carboxy or $(C_1-C_4)$alkoxycarbonyl on the carbon which is attached to the nitrogen atom N of NHR$_9$; and with the proviso that when $R_6$ is carboxy and $R_1$, $R_{10}$, $R_{11}$ and $R_5$ are all H, then $R_4$ is not benzyl, H, (phenyl)(hydroxy)methyl, methyl, ethyl or n-propyl.

4. A method as recited in claim 2 wherein said mammal is a human.

5. A method as recited in claim 3 wherein said tissue is brain tissue.

6. A method as recited in claim 3 wherein said tissue is liver tissue.

7. A method as recited in claim 3 wherein said tissue is kidney tissue.

8. A method as recited in claim 3 wherein said tissue is lung tissue.

9. A method as recited in claim 3 wherein said tissue is gut tissue.

10. A method as recited in claim 3 wherein said tissue is skeletal muscle tissue.

11. A method as recited in claim 3 wherein said tissue is spleen tissue.

12. A method as recited in claim 3 wherein said tissue is pancreas tissue.

13. A method as recited in claim 3 wherein said tissue is retina tissue.

14. A method as recited in claim 3 wherein the effective amount of glycogen phosphorylase inhibitor is about 0.1 mg/kg/day to about 100 mg/kg/day.

15. A method as recited in claim 14 wherein said glycogen phosphorylase inhibitor is administered prophylactically.

16. A method as recited in claim 14 wherein said glycogen phosphorylase inhibitor is administered chronically.

17. A method as recited in claim 3 wherein said glycogen phosphorylase inhibitor is 5-chloro-1H-indole-2-carboxylic acid [(1S)-((R)-hydroxy-dimethylcarbamoyl-methyl)-2-phenyl-ethyl]-amide;

5-chloro-1H-indole-2-carboxylic acid [(1S)-((R)-hydroxy-(methoxy-methyl-carbamoyl)-methyl)-2-phenyl-ethyl]-amide;

5-chloro-1H-indole-2-carboxylic acid [(1S)-benzyl-3-((3-hydroxy azetidin-1-yl)(2R)-hydroxy-3-oxopropyl]-amide;

5-chloro-1H-indole-2-carboxylic acid [(1S)-((R)-hydroxy-[methyl-(2-hydroxyethyl)-carbamoyl]-methyl)-2phenyl-ethyl]-amide;

5-chloro-1H-indole-2-carboxylic acid [(1S)-benzyl-(2R)-hydroxy-3-((3S)-hydroxy-pyrrolidin-1-yl)-3-oxopropyl]-amide;

5-chloro-1H-indole-2-carboxylic acid [(1S)-benzyl-(2R)-hydroxy -3-((3S,4S)-dihydroxy-pyrolidin-1-yl)-3-oxopropyl]-amide;

5-chloro-1H-indole-2-carboxylic acid [(1S)-benzyl-3-(cis-3,4-dihydroxy-pyrrolidin-1-yl)-(2R)-hydroxy-3-oxopropyl]-amide;

5-chloro-1H-indole-2-carboxylic acid [1-benzyl-2-(3-hydroxypyrrolidin-1-yl)-2-oxo-ethyl]-amide;

5-chloro-1H-indole-2-carboxylic acid [(1S)-benzyl-2-(cis-3,4-dihydroxypyrrolidin-1-yl)-2-oxo-ethyl]-amide;

5-chloro-1H-indole-2-carboxylic acid [(1S)-(4-fluorobenzyl-2-(4-hydroxy-piperidin-1-yl)-2-oxo-ethyl]-amide;

5-chloro-1H-indole-2-carboxylic acid (2-oxo-2-thiazolidin-3-yl-ethyl)-amide;

5-chloro-1H-indole-2-carboxylic acid [(1S)-benzyl-2-(3-hydroxy-azetidin-1-yl)-2-oxo-ethyl]-amide;

5-chloro-1H-indole-2-carboxylic acid [(1S)-benzyl-2-(3-hydroxyimino-azetidin-1-yl)-2-oxo-ethyl]-amide; or 5-chloro-1H-indole-2-carboxylic acid [(1S)-benzyl-2-((3S,4S)-dihydroxy-pyrrolidin-1-yl)-2-oxo-ethyl]-amide.

18. A method as recited in claim 17 wherein the effective amount is about 0.1 mg/kg/day to about 50 mg/kg/day.

19. A method as recited in claim 18 wherein the tissue is skeletal muscle or retina tissue.

20. A method as recited in claim 3 wherein said tissue is intestinal tissue.

21. A method as recited in claim 18 wherein the human has diabetes.

22. A method as recited in claim 3 wherein said tissue is the vasculature.

23. A method as recited in claim 3 wherein said tissue is spinal cord or nerve.

24. A method of reducing non-cardiac tissue damage resulting from tissue hypoxia independent of ischemia comprising administering to a mammal in need of such treatment an amount of a glycogen phosphorylase inhibitor effective at reducing non-cardiac hypoxic damage.

* * * * *